(12) United States Patent
Sze et al.

(10) Patent No.: US 9,273,105 B2
(45) Date of Patent: Mar. 1, 2016

(54) BIOACTIVE PROTEIN ISOLATED FROM CHINESE YAM AND USES THEREOF

(71) Applicant: THE UNIVERSITY OF HONG KONG, Hong Kong (CN)

(72) Inventors: Cho Wing Sze, Hong Kong (CN); Kam Lok Wong, Hong Kong (CN); Yan Bo Zhang, Hong Kong (CN); Ho Pan Cheung, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 14/563,535

(22) Filed: Dec. 8, 2014

(65) Prior Publication Data

US 2015/0158919 A1     Jun. 11, 2015

Related U.S. Application Data

(63) Continuation-in-part of application No. 13/588,702, filed on Aug. 17, 2012, now abandoned.

(60) Provisional application No. 61/524,477, filed on Aug. 17, 2011.

(51) Int. Cl.
*C07K 14/415* (2006.01)
*A61K 36/8945* (2006.01)
*A61K 38/16* (2006.01)

(52) U.S. Cl.
CPC ........... *C07K 14/415* (2013.01); *A61K 36/8945* (2013.01); *A61K 38/168* (2013.01)

(58) Field of Classification Search
None
See application file for complete search history.

*Primary Examiner* — Suzanne M Noakes
(74) *Attorney, Agent, or Firm* — Saliwanchik, Lloyd & Eisenschenk

(57) ABSTRACT

A protein isolated from the Chinese yam *Dioscorea opposita* that stimulates estrogen and progesterone release in vitro and in vivo but does not stimulate the proliferation of breast and ovarian cancer cells is disclosed. The protein exhibits anti-osteoporotic activity in vivo. Also provided are the procedure for isolation and purification of the protein and the N-terminal amino acid sequence of the protein.

9 Claims, 49 Drawing Sheets

Sample Preparation: The sample was washed 6 times with DI water and loaded onto the instrument for sequence analysis.
Instruments: 494 Precise Protein Sequencer/140C Analyzer from Applied Biosystems, Inc.
Sequencing Method: Edman Degradation

| Cycle Number | Amino Acid |
|---|---|
| 1 | G |
| 2 | E |
| 3 | G |
| 4 | K |
| 5 | I |
| 6 | T |
| 7 | T |
| 8 | V |
| 9 | W |
| 10 | G |
| 11 | Q |
| 12 | Y |
| 13 | S + S' |
| 14 | D |
| 15 | E |
| 16 | P |
| 17 | S + S' |
| 18 | L |
| 19 | T |
| 20 | E |
| 21 | A |

FIG. 7

BIOACTIVE PROTEIN ISOLATED FROM CHINESE YAM AND USES THEREOF

CROSS-REFERENCE TO RELATED APPLICATIONS

This application is a continuation-in-part of U.S. application Ser. No. 13/588,702, filed Aug. 17, 2012, which claims the benefit of U.S. Provisional Application Ser. No. 61/524,477, filed Aug. 17, 2011, which are hereby incorporated by reference in their entirety.

TECHNICAL FIELD

This invention relates to a bioactive protein originated from Chinese yam and uses thereof for increasing serum estrogen and progesterone levels and for treatment of osteoporosis, menopausal syndrome and the accompanying cognitive decline.

BACKGROUND OF THE INVENTION

Menopause, a normal part of the aging process, is the period during which the level of estrogen and progesterone secreted by the ovaries gradually declines. Approximately 80% of women experience mild or few symptoms. However some women have severe symptoms including: hot flushes, heavy sweating, anxiety, panic, or depression, drying and wrinkling of the skin, vaginal dryness and discomfort, urinary stress incontinence, cystitis, insomnia, irritability and osteoporosis. A report published by the World Health Organization in 1990 estimated that the total population of post-menopausal women in the world was 476 million. By 2030, the predicted population will reach 1.2 billion.

The current treatment to relieve menopausal syndrome is hormone replacement therapy (HRT), which consists of administration of supplementary exogenous estrogen or estrogen plus progestin most frequently using pills, implants under the skin or skin patches. While HRT increases the circulating estrogen level by providing exogenous estrogen to menopausal women, the appropriate dosage and the duration of treatment are difficult to determine due to individual variations in physiological conditions among menopausal women. Consequently, HRT is sometimes ineffective and prone to causing side effects including endometrioma, breast and ovarian cancer, coronary heart disease and stroke.

Osteoporosis results from an increased rate of bone resorption and relatively decreased rate of bone formation, resulting in reduced bone mass and micro-architectural deterioration of the skeleton, and an increased risk of fractures. Bone remodeling increases substantially in the years after menopause and remains elevated in older osteoporosis patients indicating that the loss of ovarian hormones during menopause is one of the major risk factors for osteoporosis. Bone status as such contributes to the increases in age-related skeletal fragility in women. It has been shown that trabecular bone mineral density, trabecular bone volume fraction, trabecular thickness and trabecular number all decrease with age. Also, a lower bone mass is primarily characterized by a smaller plate-to-rod ratio. All these changes weaken bone strength and increase the risk of osteoporotic fracture.

Weight-bearing exercises have an osteogenic effect in postmenopausal women. However, vigorous exercises are needed to engender an osteogenic effect in the elderly. Use of HRT in combination with weight bearing exercises has been shown to have a synergistic effect. This shows that the osteogenic response may be enhanced by the administered estrogen.

Selective estrogen receptor modulator (SERM) is a remedy in particular for relieving postmenopausal osteoporosis. However, there is no evidence showing that SERM would increase the endogenous estrogen level in menopausal women, and therefore, may not relieve menopausal syndromes other than osteoporosis.

Various studies have shown that proteins or other compounds isolated from different species of yam tuber have anti-oxidative, chitinase and immunomodulatory activities, including activating estrogen receptors. It is desirable to develop a cost-effective treatment for symptoms of menopausal syndrome in order to alleviate or prevent osteoporosis and/or cognitive decline resulting from low serum levels estrogen and progesterone levels.

BRIEF SUMMARY

The present invention provides a novel polypeptide originated from Chinese yam (*Dioscorea opposita*) tubers. The polypeptide increases circulating estrogen levels, up-regulates the expression of ovarian follicle stimulating hormone receptor (FSHR), elevates ovarian aromatase (ovarian CYP-19), and exhibits anti-osteoporotic activity.

In one embodiment, the present invention provides an isolated or substantially pure polypeptide originated from the rhizomes of *Dioscorea opposita*, wherein the polypeptide has a molecular weight of about 32.5 kDA (as determined by size exclusion chromatography on a SUPERDEX 75 10/300 GL column and visualized by silver staining following 15% Native PAGE and 15% SDS PAGE) and an N-terminal sequence Gly-Ile-Gly-Lys-Ile-Thr-Thr-Tyr-Trp-Gly-Gln-Tyr-Ser-Asp-Glu-Pro-Ser-Leu-Thr-Glu-Ala (SEQ ID NO: 1). The partial amino acid sequence of the polypeptide of the present invention determined by mass-spectrometry is KSFYTRSNFLEAVSAYPGFGTKREIAAY-FAHVTHGPMQLSWNYNYIDAGKELHFDGLN DPDI-VGRDPIISFKTSLWFWIRKGVQYVILDP-NQGFGATIRIINGGQECDGHNTAQMMAR VGYYQEYCAQ (SEQ ID NO: 6). In one embodiment, when the polypeptide, or a fragment or variant thereof, is administered to a female subject, serum estrogen and progesterone levels are increased.

Another aspect of the present invention provides therapeutic uses of the polypeptide and extracts comprising the polypeptide, or a bioactive fragment or variant thereof, for increasing the level of estradiol, estrogen, and/or progesterone in vivo and/or in vitro, for increasing the expression levels of aromatase and/or follicle-stimulating hormone receptor (FSHR), and for treatment of menopausal syndrome.

BRIEF DESCRIPTION OF THE DRAWINGS

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

FIG. 7 shows the N-terminal sequence of the isolated DOI protein.

BRIEF DESCRIPTION OF THE SEQUENCES

Figure 1:
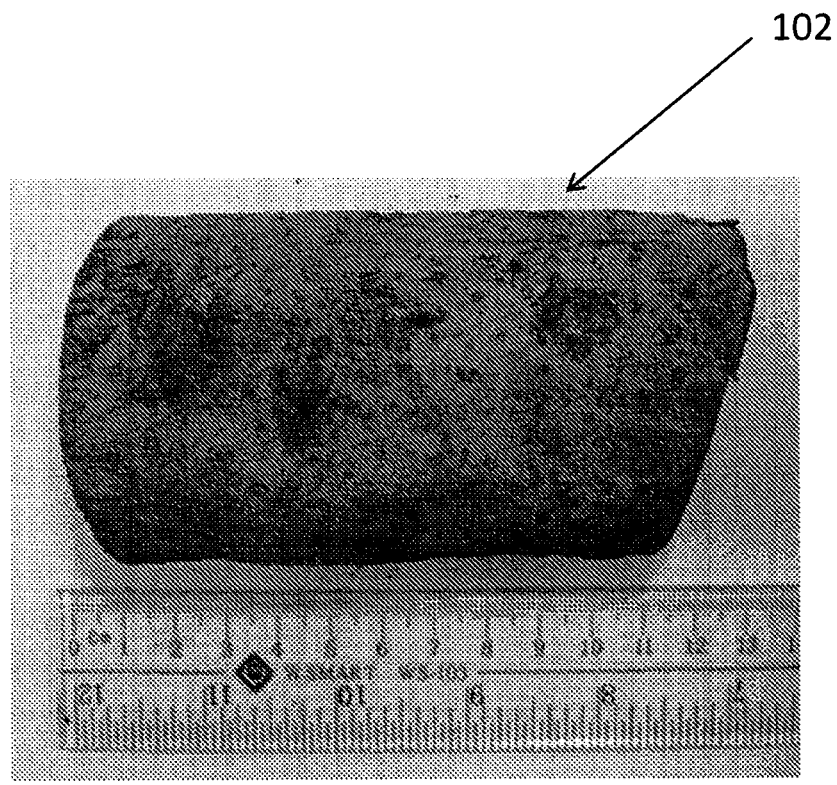
FIG. 1 is a photograph of the Chinese yam *Dioscorea opposite*.

SEQ ID NO: 1 is the N-terminal sequence of a novel protein (DOI) purified from Chinese yam tuber *Dioscorea opposita*.

SEQ ID NO: 2 is a primer sequence useful according to the present invention.

SEQ ID NO: 3 is a primer sequence useful according to the present invention.

SEQ ID NO: 4 is a primer sequence useful according to the present invention.

SEQ ID NO: 5 is a primer sequence useful according to the present invention.

SEQ ID NO: 6 is the partial amino acid sequence of the novel protein (DOI).

SEQ ID NO: 7 is a primer sequence useful according to the present invention.

SEQ ID NO: 8 is a primer sequence useful according to the present invention.

SEQ ID NO: 9 is a primer sequence useful according to the present invention.

SEQ ID NO: 10 is a primer sequence useful according to the present invention.

SEQ ID NO: 11 is a primer sequence useful according to the present invention.

SEQ ID NO: 12 is a primer sequence useful according to the present invention.

DETAILED DESCRIPTION

Throughout this specification, like numbers refer to like elements.

The present invention is directed to a novel protein (the DOI protein or peptide (DOI is also referred herein as "DO")) isolated from the Chinese yam tuber *Dioscorea opposita*. In one embodiment, the purified DOI peptide elevates circulating estrogen levels by up-regulating the expression of ovarian follicle stimulating hormone receptor (FSHR) and ovarian aromatase (ovarian CYP-19). In another embodiment, the DOI peptide reduces or prevents the decalcification of bone and osteoporosis. In another embodiment the DOI peptide increases the level of brain derived neurotrophic factor (BDNF) in the hippocampus and increases the levels of BDNF and TrkB gp145 receptor protein in the prefrontal cortex.

Proteins

In one embodiment, the present invention provides an isolated or substantially pure polypeptide having an apparent molecular weight of about 32.5 kDa, wherein the first twenty-one consecutive amino acids at the N-terminal of the polypeptide consists of SEQ ID NO: 1. In one embodiment, the polypeptide originates from *Dioscorea* sp. In one specific embodiment, the polypeptide originates from *Dioscorea opposita*.

In another embodiment, the polypeptide comprises the partial amino acid sequence of KSFYTRSNFLEAVSAYPGF-GTKREIAAYFAHVTHGPMQLSWNYNY-IDAGKELHFDGLN DPDIVGRDPIISFKTSLWF-WIRKGVQYVILDPNQGFGATIRIINGGQ-ECDGHNTAQMMAR VGYYQEYCAQ (SEQ ID NO: 6).

In one embodiment, the polypeptide of the present invention has characteristics of the DOI peptide as shown in Table 1.

In one embodiment, the polypeptide of the present invention increases the level of estradiol, estrogen, and/or progesterone in vivo and/or in vitro. In one specific embodiment, the polypeptide of the present invention increases the level of estradiol, estrogen, and/or progesterone in ovarian tissue and/or the blood (e.g. serum, plasma, whole blood). In one embodiment, the polypeptide of the present invention increases the expression aromatase and/or follicle-stimulating hormone receptor (FSHR). In one specific embodiment, the polypeptide of the present invention increases the ratio of expression level of aromatase:GAPDH and/or FSHR:GAPDH.

In one embodiment, the polypeptide of the present invention has higher activity (such as increasing the level of estradiol, estrogen, and/or progesterone) after incubation at pH about 1 than after incubation at pH 0.1 or at pH 2. In one embodiment, the polypeptide of the present invention has higher activity (such as increasing the level of estradiol, estrogen, and/or progesterone after incubation at 80° C. than after incubation at 60° C. or at 100° C.

In one embodiment, the polypeptide of the present invention has activity (such increasing the level of estradiol, estrogen, and/or progesterone) after incubation at pH 0.1. In one embodiment, the polypeptide of the present invention has activity (such as increasing the level of estradiol, estrogen, and/or progesterone) after incubation at 100° C.

In one embodiment, the polypeptide of the present invention does not increase the proliferation of breast cancer cells. In one embodiment, the polypeptide of the present invention does not increase the body weight of a subject. In one embodiment, the polypeptide of the present invention increases bone mineral density, bone volume fraction, trabecular number, and/or trabecular thickness in a subject (including a subject with low levels of estrogen and/or progesterone). In one embodiment, the polypeptide of the present invention decreases structure model index and/or trabecular separation in a subject (including a subject with low levels of estrogen and/or progesterone).

In one embodiment, the polypeptide of the present invention increases the levels of brain derived neurotrophic factor (BDNF) and/or TrkB gp145 receptor in the brain of a subject (including a subject with low levels of estrogen and/or progesterone).

In one embodiment, the present invention provides an isolated or substantially pure polypeptide having an apparent molecular weight of about 32.5 kDa, wherein the N-terminal sequence of the polypeptide has at least 85% identity with SEQ ID NO:1, wherein the polypeptide increases the level of estradiol, estrogen, and/or progesterone in vivo and/or in vitro. In another embodiment, the partial amino acid sequence of the peptide has at least 85% identity with SEQ ID NO: 6, wherein the polypeptide increases the level of estradiol, estrogen, and/or progesterone in vivo and/or in vitro.

In one embodiment, the polypeptide of the present invention has an apparent molecular weight of 27 kDa to 34 kDa, or a molecular weight therebetween, such as 28 kDa, 29 kDa, 30 kDa, 31 kDa, 31.5 kDa, 32 kDa, 32.5 kDa, 33 kDa, 33.5 kDa, or 34 kDa.

In one embodiment, the present invention provides an isolated or substantially pure polypeptide, wherein the polypeptide has at least 85% sequence identity to a peptide having an apparent molecular weight of about 32.5 kDa and the first twenty-one consecutive amino acids of the N-terminal of the peptide consists of SEQ ID NO:1, wherein the polypeptide increases the level of estradiol, estrogen, and/or progesterone in vivo and/or in vitro. In another embodiment, the present invention provides an isolated or substantially pure polypeptide, wherein the polypeptide has at least 85% sequence identity to a peptide wherein the first twenty-one consecutive amino acids of the N-terminal of the peptide consists of SEQ ID NO:1 and a partial amino acid sequence of the peptide further comprises SEQ ID NO: 6, wherein the polypeptide increases the level of estradiol, estrogen, and/or progesterone in vivo and/or in vitro.

In one embodiment, the present invention provides an isolated or substantially pure bioactive fragment or variant of a polypeptide, wherein the polypeptide has an apparent molecular weight of about 32.5 kDa and the first twenty-one consecutive amino acids of the N-terminal of the polypeptide consists of SEQ ID NO:1, wherein increases the level of estradiol, estrogen, and/or progesterone in vivo and/or in vitro. In one embodiment, the fragment or variant has at least 10%, 20%, 30%, 40%, 50%, 60%, 65%, 70%, 75%, 80%, 85%, 90%, 95%, or 97% sequence identity to the polypeptide of the present invention, and the fragment or variant increases the level of estradiol, estrogen, and/or progesterone in vivo and/or in vitro.

A "variant" refers to natural variants, including polymorphisms, variations between homologous proteins of a related species, disease-associated mutations and/or RNA editing events.

In one embodiment, the present invention provides an isolated or substantially pure bioactive fragment or variant of a polypeptide, wherein the polypeptide has a molecular weight of about 33.5 kDa as measured by mass spectrometry and a partial amino acid sequence of the polypeptide comprises SEQ ID NO: 6, wherein increases the level of estradiol, estrogen, and/or progesterone in vivo and/or in vitro. In one embodiment, the fragment or variant has at least 10%, 20%, 30%, 40%, 50%, 60%, 65%, 70%, 75%, 80%, 85%, 90%, 95%, or 97% sequence identity to the polypeptide of the present invention, and the fragment increases the level of estradiol, estrogen, and/or progesterone in vivo and/or in vitro. Such bioactive fragments and variants are considered equivalents of the polypeptide of the subject invention.

In another embodiment, the partial amino acid sequence of the peptide has at least 85% identity with SEQ ID NO: 6, wherein the polypeptide increases the level of estradiol, estrogen, and/or progesterone in vivo and/or in vitro.

In one embodiment, the present invention provides proteins and fusion constructs comprising a polypeptide of the present invention.

The polypeptides of the present invention can be naturally-occurring or can be recombinantly-produced.

In one embodiment, the present invention provides an isolated aqueous extract from a *Dioscorea* species (e.g. *Dioscorea opposita*), wherein the extract comprises a polypeptide of the present invention.

In certain embodiments, the present invention pertains to isolated or substantially pure proteins and polypeptides. The term "substantially pure," as used herein, refers to more than 99% pure.

As used herein, "isolated" refers to extracts and compounds (e.g., proteins and polypeptides) that have been removed from any environment in which they may exist in nature. For example, an isolated extract or compound would not refer to the compound or extract as it exists in plants from which the compound can be isolated. In preferred embodiments, the compounds and extracts of the present invention are at least 75% pure, preferably at least 90% pure, more preferably are more than 95% pure and most preferably are more than 99% pure (substantially pure).

Treatment of Menopausal Syndrome and Other Diseases

Another aspect of the subject invention provides therapeutic uses of the polypeptide compound and extracts comprising the polypeptide compound for increasing the level of estradiol, estrogen, and/or progesterone in vivo and/or in vitro, for increasing the expression levels of aromatase and/or follicle-stimulating hormone receptor (FSHR), and for treatment of menopausal syndrome.

In one embodiment, the present invention provides a method of increasing the level of a female reproductive hormone (such as estradiol, estrogen, and/or progesterone) in a cell, comprising administering to a cell an effective amount of a composition comprising a polypeptide compound of the invention or a salt thereof.

In one embodiment, the cell is in a subject in need of an increase in the level of a female reproductive hormone (e.g., estradiol, estrogen, and/or progesterone). In one embodiment, the cell is an ovarian cell. In one embodiment, the subject has a low serum level of a female reproductive hormone (e.g., estradiol, estrogen, and/or progesterone), when compared to the level of a normal female population with normal reproductive function. In one embodiment, the subject is a female human subject, and the normal female population consists of females at the age of 14-40 with normal reproductive function. In one embodiment, the subject is a female at menopause, perimenopause, or postmenopause period.

In one embodiment, the present invention does not increase the proliferation of breast cancer cells. In one embodiment, the present invention does not increase the body weight of a subject.

In one embodiment, the present invention can be used to treat osteoporosis of a subject. In one embodiment, the subject is a female having estradiol, estrogen, and/or progesterone levels lower than that a normal female population with reproductive function. In one embodiment, the present invention can be used to improve cognitive function of a subject. In one embodiment, the subject is a female having estradiol, estrogen, and/or progesterone levels lower than that a normal female population with normal reproductive function. In one embodiment, the present invention can be used to increase the levels of brain derived neurotrophic factor (BDNF) and/or TrkB gp145 receptor in the brain of a subject.

The term "subject" or "patient," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; domesticated animals such as dogs, cats, horses, cattle, pigs, sheep, goats, chickens; and other animals such as mice, rats, guinea pigs, and hamsters. In one embodiment, the subject or patient is a female.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "effective amount," as used herein, refers to an amount that is capable of treating or ameliorating a disease or condition or otherwise capable of producing an intended therapeutic effect.

In one embodiment, the present invention provides a method of treating osteoporosis comprising administering an aqueous extract of a *Dioscorea opposita* plant rhizome to a patient, and thereby stimulating estrogen and progesterone secretion.

In one embodiment, the present invention provides a method of treating menopausal syndrome by administering an aqueous extract of a *Dioscorea opposita* plant rhizome to a patient and stimulating estrogen and progesterone secretion.

In one embodiment, the present invention provides a method of treating osteoporosis in a patient by administering an aqueous extract of a *Dioscorea opposita* plant rhizome to the patient and up-regulating follicle stimulating hormone receptor and ovarian aromatase.

In one embodiment, the present invention provides a method of treating menopausal syndrome by administering an aqueous extract of a *Dioscorea opposita* plant rhizome to the patient and stimulating estrogen and progesterone secretion in response to the treatment.

In one embodiment, the present invention provides a method of treating reduced cognitive function in a patient having low serum estrogen and progesterone levels by administering an aqueous extract of a *Dioscorea opposita* plant rhizome to the patient and thereby raising serum estrogen and progesterone levels and improving cognitive function in response to the raised serum estrogen and progesterone levels.

In one embodiment, the present invention provides a method of improving cognitive function in a patient by administering to the patient an aqueous extract of a *Dioscorea opposita* plant rhizome and elevating brain-derived neurotrophic factor expression in the hippocampus and cortex of the patient's brain in response to the extract.

In one embodiment, the present invention provides a method of improving cognitive function in a patient by administering to the patient an aqueous extract of a *Dioscorea opposita* plant rhizome and elevating TRKB receptor in the prefrontal cortex of the patient's brain in response to the extract.

Protein Extraction Form *Dioscorea opposita*

Rhizomes 102 of *Dioscorea opposita* (FIG. 1) were peeled and homogenized in an aqueous extraction buffer (5% acetic acid+0.1% β-mercaptoethanol) in a ratio of 1:2 (w/v) for 3 hours at 4° C. The homogenate was subjected to centrifugation at 17,700 g for 30 min at 4° C. The supernatant was collected and ammonium sulfate was added to 80% of saturation. The mixture was stirred at 4° C. overnight and subjected to centrifugation at 17,700 g for 1 hr at 4° C. The supernatant was collected and ammonium sulfate was added to 80% of saturation. The mixture was stirred at 4° C. overnight and subjected to centrifugation at 17,700 g for 1 hr at 4° C. The precipitate (protein extract) was retained and resuspended in purified water. The protein extract mixture was dialyzed against doubly distilled $H_2O$ overnight and then subjected to ultra-centrifugation at 40,000 g for 2 hr at 4° C.

The supernatant was collected and subjected to fast protein liquid chromatography (FPLC).

Column Purification

A sample of the above extract was adjusted to a final concentration of 100 mM Tris (pH 8.0) and applied to a HiPrep 16/10 DEAE FF column (GE Healthcare, Inc., Princeton, N.J.) and chromatographed by FPLC. The elution buffer consisted of buffer A: 100 mM Tris (pH 8.0), and buffer B: 1M NaCl containing 100 mM Tris (pH 8.0). A gradient 0-45% Buffer B was used. The elution profile is shown as chromatogram in FIG. 2. Fraction D3 was collected and dialyzed against double distilled $H_2O$ overnight.

Figure 3:
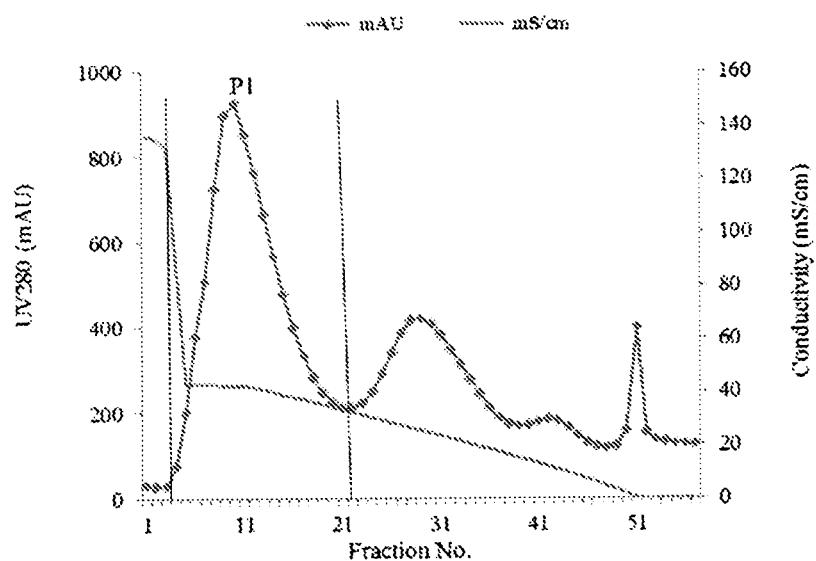
FIG. 3 is a chromatogram showing the further purification of a DOI protein fraction on a HiPrep 16/10 Phenyl FF (high sub) column.

Fraction D3 was then adjusted to 50% Buffer B and applied to a HiPrep 16/10 Phenyl FF (high sub) column (GE Healthcare, Inc., Princeton, N.J.), and chromatographed by FPLC. An elution buffer consisting of milli-Q $H_2O$, and 10 mM sodium phosphate buffer (pH 7.0) containing 1M $(NH_4)_2SO_4$, (buffer B) was used. The column was eluted with a gradient of 30-0% buffer B. The elution profile is shown in FIG. 3. Fraction P1 was collected and dialyzed against double distilled $H_2O$ overnight and then lyophilized to obtain a powdered residue.

Figure 4:
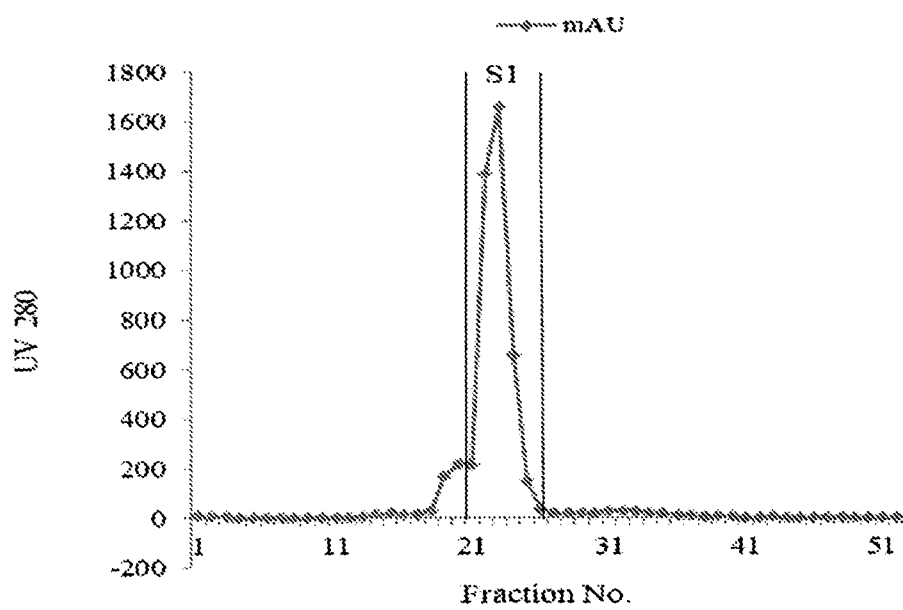
FIG. 4 is a chromatogram showing the purification of a DOI protein fraction on a Superdex 75 10/300 GL column.

The lyophilized powder from 302 was dissolved in 50 mM sodium phosphate buffer (pH 7.2) containing 150 mM NaCl, applied to a Superdex 75 10/300 GL column (GE Healthcare, Inc., Princeton, N.J.) and chromatographed by FPLC. The column was eluted with a 50 mM sodium phosphate buffer (pH 7.2) at a flow rate of 0.6 ml/min. The chromatogram is shown in FIG. 4. Fraction S2 was collected and dialyzed against double distilled $H_2O$ overnight and lyophilized to dryness. The lyophilized residue was recovered and stored at −20° C. This powdered residue is referred to as DOI peptide, and is furthered characterized to evaluate its physical, chemical and biological properties.

Chemical Characterization of DOI

Figure 5:
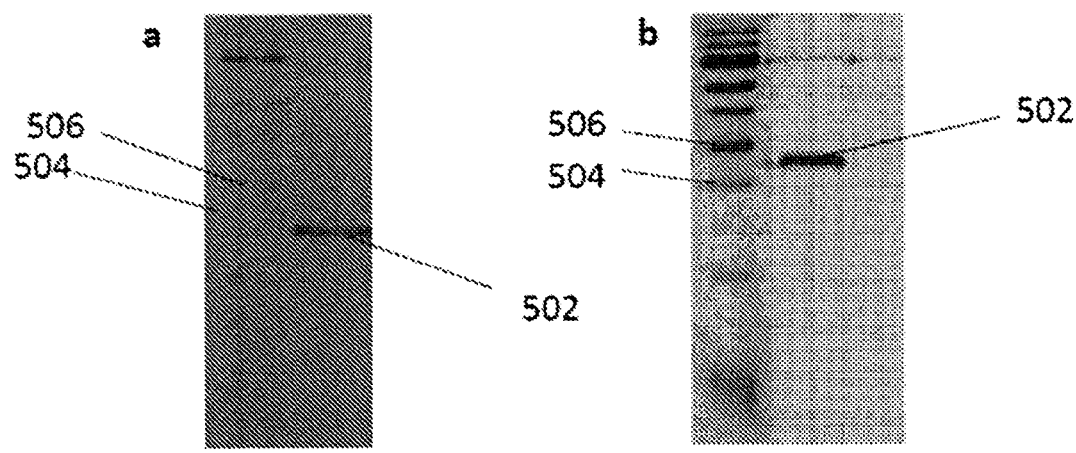
FIG. 5 is a photograph of a 15% Native PAGE of DOI extract (a) and 15% SDS PAGE (b), showing the protein recovered from the DOI extract visualized by silver staining.

A portion of the powdered residue DOI was subjected to polyacrylamide gel electrophoresis (PAGE) on a 15% native PAGE system, and on a 15% sodium dodecyl-sulfate (SDS) PAGE system, as shown in FIGS. 5A and 5B, respectively. DOI peptide was found to migrate as a single band 502 in both systems, indicating that the DOI residue is a relatively pure peptide. The migration of the DOI peptide fraction was compared to that of molecular weight standards 504, having a molecular weight of 26 kDA and 506 having a molecular weight of 34 kDA. The molecular weight of DOI peptide was found to be approximately 30 kDA as determined from its migration on SDS PAGE.

Figure 6A:
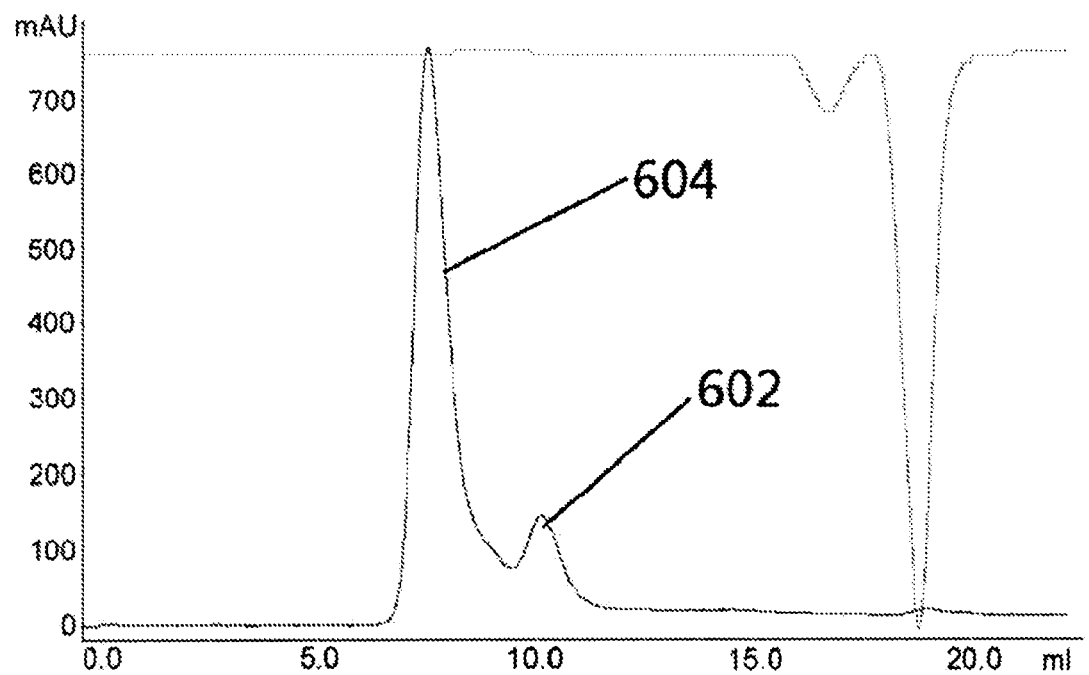
FIG. 6A is a chromatogram showing elution of the protein standards blue dextran and ovalbumin on a SUPERDEX 75 10/300 GL column.
Figure 6B:
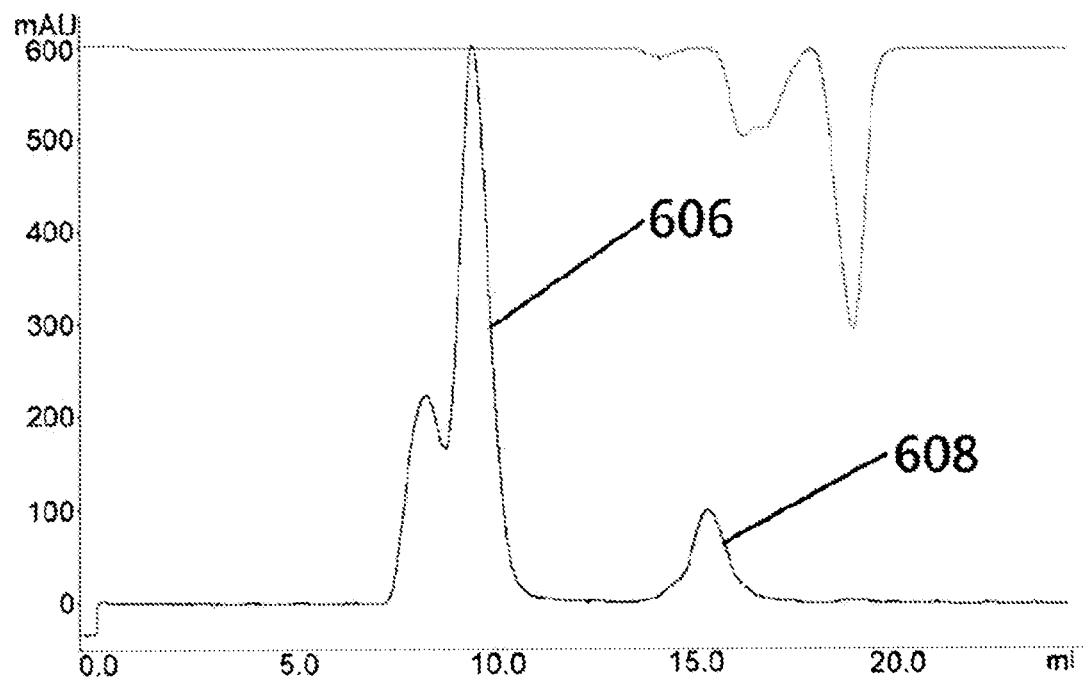
FIG. 6B is a chromatogram showing the elution of the protein standards serum albumin and aprotinin on a SUPERDEX 75 10/300 GL column.
Figure 6C:
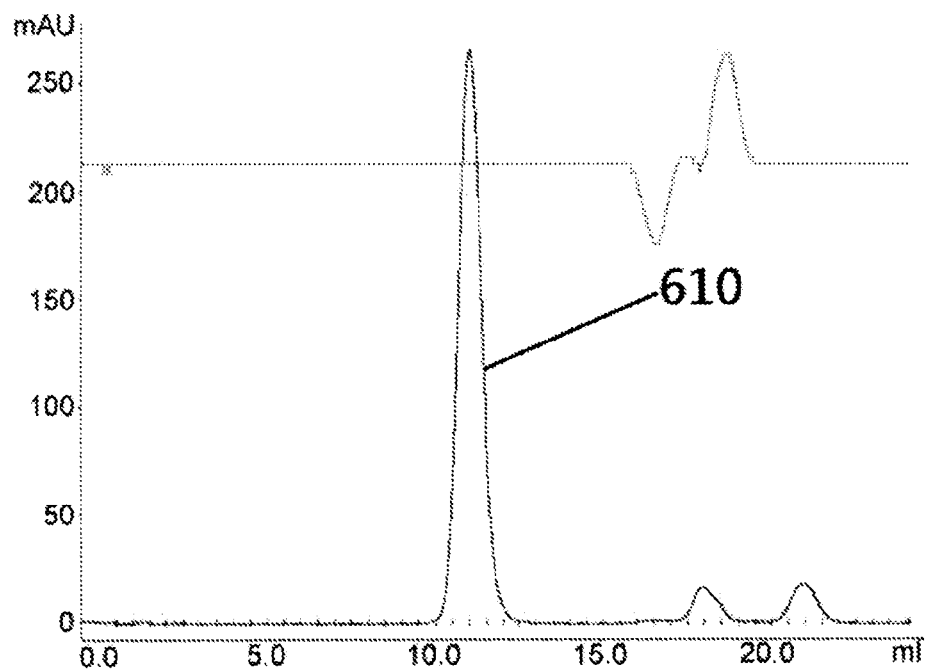
FIG. 6C is a chromatogram showing the elution of DOI peptide on a Superdex 75 10/300 GL column, in accordance with the present invention.
Figure 6D:
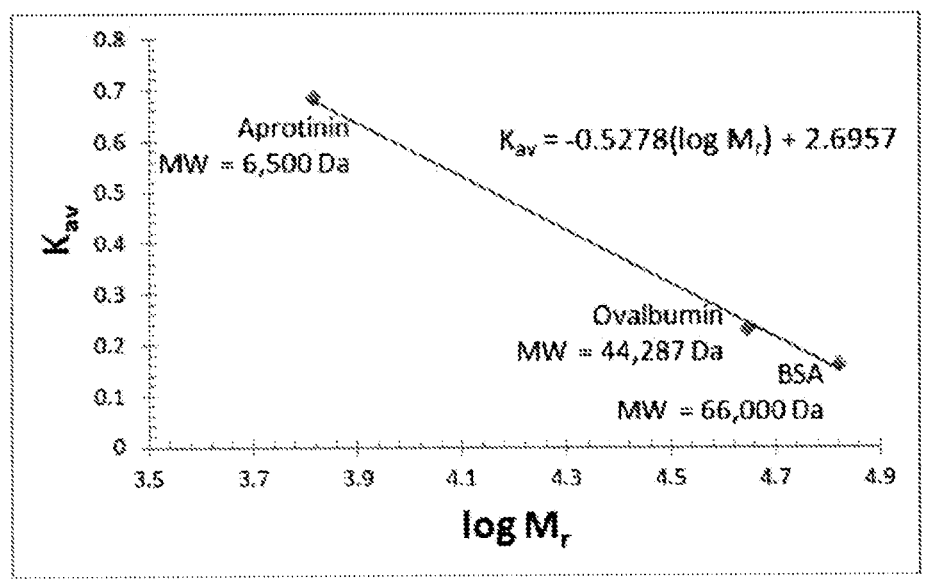
FIG. 6D is a graph showing a calibration curve from which the molecular weight of DOI peptide was determined.

The native size of DOI peptide (fraction S2) was determined by its retention time on a Superdex 75 10/300 column using Aprotinin (6500 Da), ovalbumin (44287 Da), and bovine serum albumin (66000 Da) as calibration size standards. The chromatogram showing the elution time of ovalbumin 602 as well as the column front elution volume, indicated by blue dextran 604, is shown in FIG. 6A. The chromatogram showing the elution time of bovine serum albumin, 606 and aprotinin 608 is shown in FIG. 6B. A standard curve, shown in FIG. 6D, was constructed by plotting the elution volumes against the molecular weights of the three standards. Finally, the purified fraction S2 (DOI peptide) 610, was chromatographed and the chromatogram is shown in FIG. 6C. The size calculated for the DOI peptide from standard curve was 32.5 kDa.

A summary of the molecular weight determination of the DOI peptide as determined from its chromatographic elution volume is presented in Table 1:

TABLE 1

Calculation of molecular weight of DOI:

| Superdex 75 10/300 GL | | | | |
|---|---|---|---|---|
| Bed volume (ml) | 18.8 | | | |
| Void volume (ml) | 7.52 | | | |

| | Retention volume (ml) | Kav | Molecular weight (MW) | log MW |
|---|---|---|---|---|
| Bovine serum albumin | 9.35 | 0.162234043 | 66000 | 4.819544 |
| Ovalbumin | 10.121 | 0.230585106 | 44287 | 4.646276 |
| Aprotinin | 15.25 | 0.685283688 | 6500 | 3.812913 |
| DOI | 11.06 | 0.313829787 | 32536.47007 | 4.51237 |

The molecular weight of the DOI peptide was calculated to be approximately 32.5 kDa.

A summary of the purification of the DOI peptide is presented in Table 2. DOI peptide was found to be approximately 0.017% of the total protein in the DOI rhizome.

TABLE 2

| Purification steps | Total protein (mg)/100 g Dioscorea opposita | Protein yield (%) |
|---|---|---|
| Homogenate | 165.19 | 100 |
| Supernatant after ammonium sulfate precipitation, dialysis and ultracentrifugation | 72.96 | 44.17 |
| fraction D3 | 13.12 | 7.94 |
| fraction P1 | 6.48 | 3.93 |
| fraction S2 (DOI) | 0.6 | 0.3 |

N-terminal sequence analysis of the isolated DOI peptide was carried out on an Model 494 Precise Protein Sequencer and a 140 Analyser (Applied Biosystems, Inc., Carlsbad, Calif.) using the Edman Degradation process. The results of the sequencing analysis are shown in FIG. 7. N-terminal sequence 700 was found to be:

(SEQ ID NO: 1)
Gly-Ile-Gly-Lys-Ile-Thr-Thr-Tyr-Trp-Gly-Gln-Tyr-

Ser-Asp-Glu-Pro-Ser-Leu-Thr-Glu-Ala.

Figure 35:
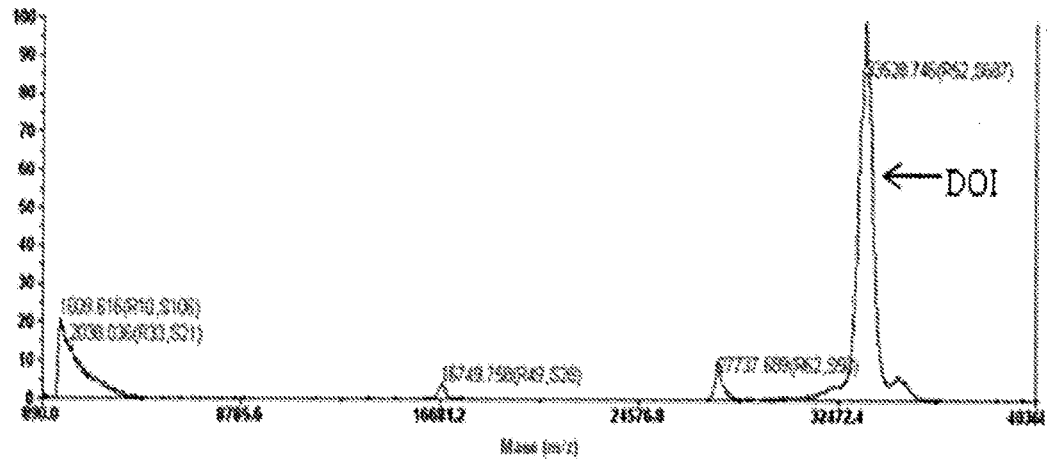
FIG. 35 shows the results of the size measurement of DOI by mass spectrometry.

The partial amino acid sequence was measured by mass spectrometry, with the support of the Proteomics Centre of Virji University, Amsterdam. DOI (4.5 ug) was redissolved in 50 mM ammonium bicarbonate, incubated with 300 ng trypsin/Lys-C Mix (Promega, Mass Spec grade) at 37° C. for 16 hrs, and then dried in a speedvac. Peptides were analysed by nanoLC-MSMS using an Ultimate 3000 LC system (Dionex) coupled to the TripleTop 5600 mass spectrometer (AB-Sciex). Peptides were trapped on a 5 mm Pepmap 100 C18 column (300 μm ID, 5 μm particle size, from Dionex) and fractionated on a 200 mm Alltima C18 column (100 μm ID, 3 μm particle size). The acetonitrile concentration in the mobile phase was increased from 5 to 40% in 30 min, and to 90% in 3 min at a flow rate of 400 nL/min. The eluted peptides were electrosprayed into the TripleTop MS. The mass spectrometer was operated in a data-dependent mode with single MS full scan (m/z 350-1200) followed by top 20 MS/MS scan. The data were searched with PEAKS7 using the UniProt_SwissProt plant database. The exact molecular weight of DOI was 33.5 kDa as measured by mass spectrometry (FIG. 35). The partial amino acid sequence of DOI determined by mass-Spectrometry was KSFYTRSNFLEAVSAYPGFGTKRE-IAAYFAHVTHGPMQLSWNYNYIDAGKELHFDGLN DPDIVGRDPIISFKTSLWF-WIRKGVQYVILDPNQGFGATIRIINGGQ-ECDGHNTAQMMAR VGYYQEYCAQ (SEQ ID NO: 6).

Biological Characterization of DOI Determination of Estradiol-Stimulating Effect of DOI by In Vitro Estrogenic Assay Female Sprague-Dawley rats (SD-rats), 21 to 23 day-old, were primed with 80 IU of pregnant mare serum gonadotropin (PMSG) (Sigma) for 48 hours to stimulate follicular development. The rats were then sacrificed and ovaries were dissected. The ovarian follicles were punctured with a 25-gauge needle and granulosa cells were extracted. The granulosa cells were then cultured for 2 hours in serum-free DME/F12 1:1 medium supplemented with penicillin-streptomycin and 1% BSA at 37° C. in an atmosphere of 5% $CO_2$. The DOI peptide was then added to the granulosa cells and incubated for 12 hours. The cell culture medium was collected for measurement of estrogen concentration and the cells were harvested for RNA and protein isolation.

Figure 8:
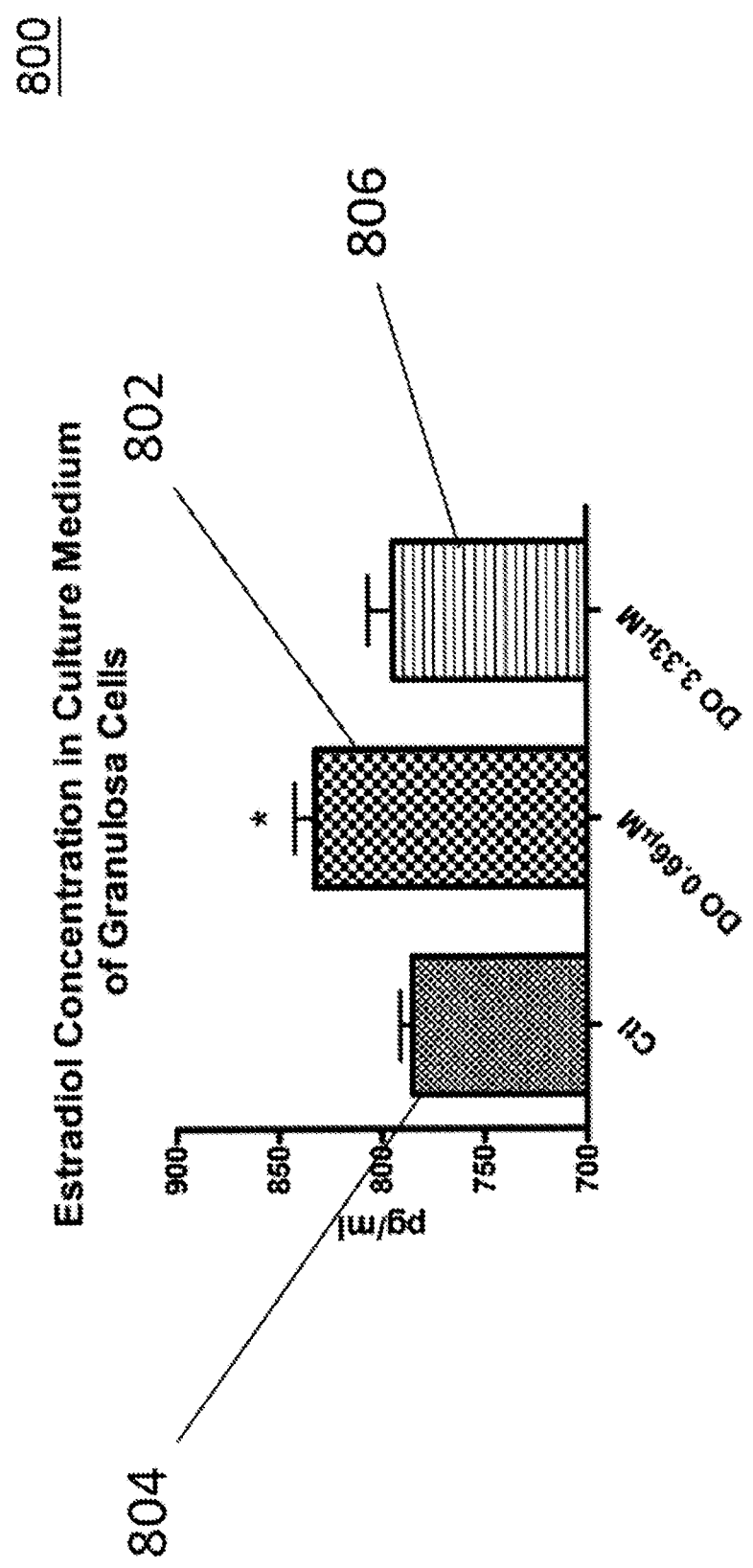
FIG. 8 is a graph showing the estrogenic activity of DOI protein on granulosa cells, in accordance with the present invention.

As shown in graph 800, FIG. 8, after a 12 hour incubation period, the average estradiol level in the culture medium of granulosa cells treated with DOI peptide at 0.66 μM (802) and 3.33 μM (806) were 832.2±10.12 pg/ml and 794.4±12.05 pg/ml respectively. There was a significant increase in estradiol level in 0.66 μM DOI-treated group 702 (p=0.016, un-paired t-test) compared with control 804 (785.5±5.766 pg/ml).

Determination of Acid-Stability, Alkali-Stability, Thermo-Stability, and Chitinase Activity of DOI In order to determine the effect of pH on DOI peptide, DOI peptide was incubated with HCl at a concentration of 0.01M, 0.1M and 1M respectively, at 4° C. for 30 minutes (DOI: HCl=1:1). The mixtures were then neutralized with NaOH with concentration of 0.01M, 0.1M and 1M, respectively (NaOH:HCl=1:1). The treated DOI was then added to the granulosa cells and incubated for 12 hours. The cell culture medium was collected for measurement of estrogen concentration. The results showing the effect of basic pH on the activity of DOI peptide are presented in graph 900, shown in FIG. 9.

The average estradiol level in the culture medium of granulosa cells treated with 10 nM DOI, pretreated with 0.01M (902), 0.1M (904) and 1M NaOH (906) were 486.1±16.86 pg/ml, 454.6±12.91 pg/ml and 449.7±15.97 pg/ml respectively. There was no significant difference in estradiol concentration, compared to control group 910, having no added DOI peptide. Estradiol concentration for control group 910 (no added DOI peptide) was found to be (446.8±3.04 pg/ml). A positive control group 908 comprising DOI peptide not exposed to NaOH, showed increased release of estradiol. When exposed to forskolin (912), as a viability test for the cells, the granulosa cells increased estradiol release (912) as expected.

DOI was incubated with HCl at a concentration of 0.01M, 0.1M and 1M respectively, at 4° C. for 30 minutes (DOI peptide:HCl=1:1). The mixtures were then neutralized with NaOH with concentration of 0.01M, 0.1M and 1M, respectively (NaOH:HCl=1:1). The treated DOI was then added to the granulosa cells and incubated for 12 hours. The cell culture medium was collected for measurement of estrogen concentration.

Ovarian granulosa cells incubated with DOI peptide that had been exposed to HCl were compared cells exposed to OD peptide having had no exposure to acid. The results are presented in graph 1000 of FIG. 10. The average estradiol level in culture medium of granulosa cells treated with 10 nM DOI peptide pretreated with 0.01M (1002), 0.1M (1004) and 1M (1006) HCl were 473.1±5.92 pg/ml, 508.1±6.33 pg/ml and 471.8±6.1 pg/ml respectively. There was a significant increase in estradiol level in all HCl treated groups (p=0.017, 0.0009 and 0.029 respectively, un-paired 1-test) compared with control 910 (446.8±3.04 pg/ml). Estradiol release from the acid treated groups was similar to that of the DOI peptide (no acid exposure) treated group (1008).

Figure 11:
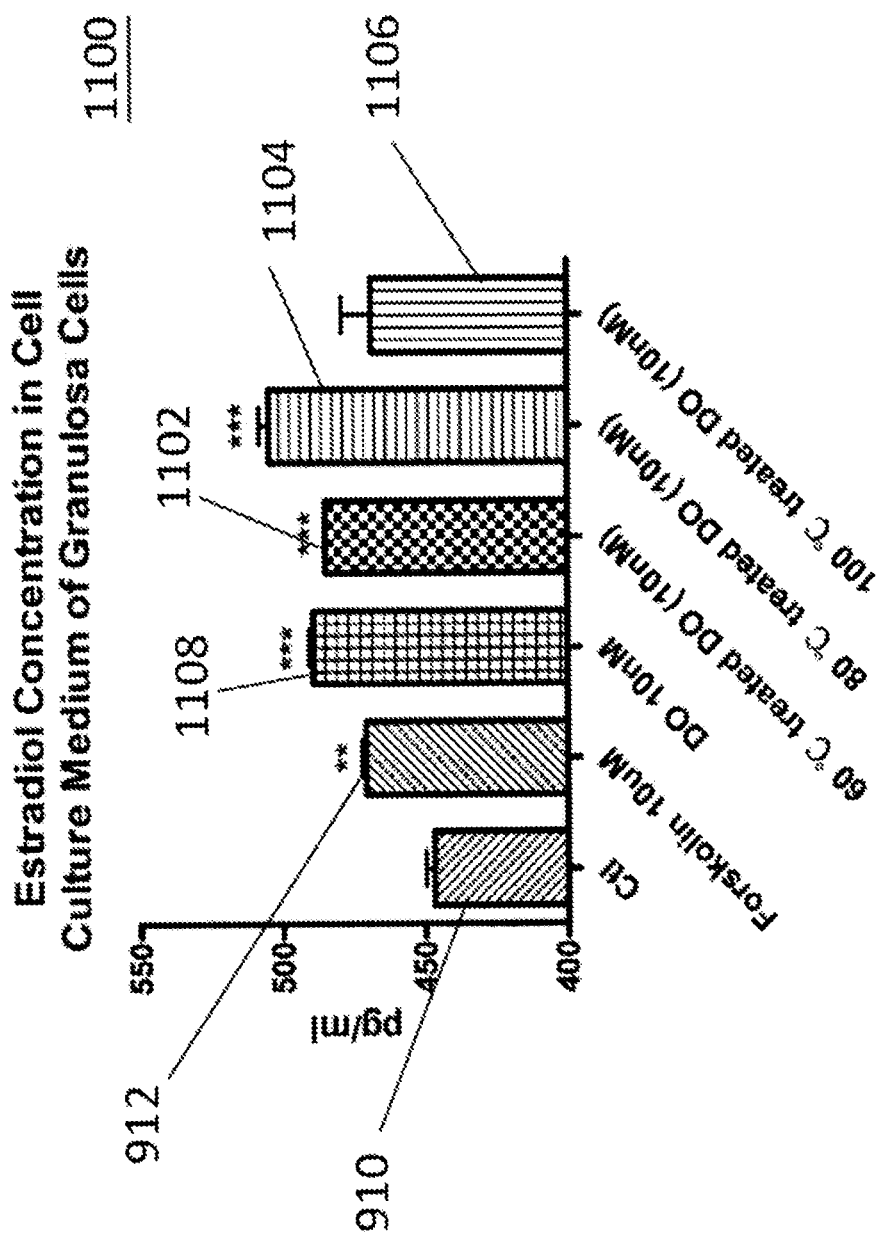
FIG. 11 is a graph showing the estrogenic activity of heat treated DOI peptide on granulosa cells. Results are expressed as means±SEM, n=3. * $p<0.05$, $p<0.01$,* $p<0.001$ compared with control group by un-paired t-test.

For the thermo-stability test, DOI was incubated at 60° C., 80° C. and 100° C. for 30 minutes. The treated DOI was then added to the granulosa cells and incubated for 12 hours treatment. The cell culture medium was collected for measurement of estrogen concentration. The results are shown in graph 1100 shown in FIG. 11. The chitinase activity of DOI was measured by using Chitinase Assay Kit (# CS0980, Sigma-Aldrich) following the manufacturer's instruction. Three substrates, including 4-nitrophenyl N,N-diacetyl-β-D-chitobioside (N6133), 4-nitrophenylN-acetyl-β-D-glucosaminide (9376), and 4-nitrophenyl β-D-N,N',N''-triacetylchitotriose (N8638) were used to evaluate DOI's exochitinase activity (chitobiosidase activity), exochitinase activity (β-N-acetylglucosaminidase activity), and endochitinase activity, respectively.

The average estradiol level in a culture medium of granulosa cells treated with 10 nM DOI incubated in 60° C., 80° C. and 100° C. was 484.9±0.46 pg/ml, 504.9±3.38 pg/ml and 468.5±10.62 pg/ml respectively. There was a significant increase in estradiol level in treatment groups with DOI incubated in 60° C. (1102) and 80° C. (1104) (p=0.0002 un-paired t-test) compared with control 910 (446.8±3.04 pg/ml). Estradiol release from all treated groups were similar to estradiol release by group 912, which was treated with DOI peptide not exposed to heat.

In one embodiment, the estrogenic activity of DOI could be maintained under acidic condition with highest activity after treatment with 0.1M HCl (pH 1). After treated with high temperature (60° C. and 80° C.), the activity of DOI was also stable. However, the activity diminished after treatment with NaOH with a dose dependent manner.

Evaluation of Viabilities of BT-483 Cells, OVCA-429 Cells, Mouse Splenocytes and Ovarian Granulose Cells after Incubation of DOI by MTT Assay BT-483 estrogen receptor positive-breast cancer cell line and OVCA-429 cancer cells with estrogen receptor ($3 \times 10^4$ and $1.5 \times 10^4$ cells per well in 96 well-plate respectively) were serum starved for 24 hours prior to drug treatment. Mouse splenocytes were isolated from BALB/c mice. The isolated splenocytes were diluted with RPMI 1640 medium with 15% fetal bovine serum and 1% penicillin-streptomycin followed by culturing in 96-well microplates at a density of $5 \times 10^5$ cells/100 μl/well. The preparation of ovarian granulosa cell was described above. All cells were cultured at 37° C. in a humidified atmosphere with 5% carbon dioxide for 24 hours. The DOI was then added in complete medium at the final concentration of 1 nM, 10 nM and 100 nM for 48 hours in case of cancer cells and added in RPMI 1640 medium with 15% fetal bovine serum and 1% penicillin-streptomycin for 72 hours in case of mouse splenocytes, respectively, followed by incubation with 10 μl MTT solution (5 mg/ml) for 3 hours. Formazan crystal was dissolved by DMSO. Absorbance at O.D. 540 nm was measured with a microplate reader (Model 680, Bio-Rad). Percentage viability relative to the control was calculated.

Action of DOI on Estradiol-Stimulating Effect In Vitro

DOI at the concentrations of 0.01M, 0.1M and 1M was added to the ovarian granulosa cells and incubated for 12 hours. The cell culture medium was collected for measurement of estrogen concentration and the cellular proteins were extracted for Western blotting analysis. Western blotting was performed using specific anti-FSHR (sc-13935, Santa Cruz Biotechnology, Inc) and anti-aromatase antibodies (sc-14245, Santa Cruz Biotechnology, Inc) for proteins from ovarian granulosa cells. For kinase inhibition assay, the granulosa cells were cultured for 1 hours in serum-free DME/F12 1:1 medium supplemented with penicillin-streptomycin and 1% bovine serum albumin at 37° C. in an atmosphere of 5% $CO_2$ with a cell density of $1 \times 10^6$ cells in a 24-well plate. The cells were then treated with 10 µM protein kinase A inhibitor (H-89), 20 µM protein kinase B inhibitor (LY-294002) and 30 µM protein kinase C inhibitor (GF-109203X), separately, for 1 hour. DOI (10 nM) was then added and incubated for another 12 hours. The cell culture medium was collected for measurement of estrogen concentration to evaluate the role of protein kinase A, B, C. In addition, in order to identify whether the DOI binding receptor is FSH receptor (FSHR), ovarian granulosa cells were pre-treated with 2 µg of FSHR antibody (sc-7798, Santa Cruz, USA) as FSHR antagonist for 30 min before treatment with DOI (0.1 µM and 0.01 µM), 1 µM forskolin (Sigma-Aldrich, USA) as positive control, or 2 µg of FSHR antibody as negative control, the cell culture medium was collected for measurement of estradiol after treatment for 12 hours in the FSHR-attenuated ovarian granulosa cell model.

Action of DOI on Estradiol-Stimulating Effect In Vivo

Animal model: Female Sprague-Dawley rats (SD-rats), 16-20 months old, with low serum estrogen levels were used as an animal model of aging. Female SD-rats, aged 8 months, were purchased from the Laboratory Animal Unit, The University of Hong Kong. The animals were housed in an air-conditioned room at an ambient temperature of 24° C. and 50-65% relative humidity with automatic 12 h light:dark cycles. The experiment had been approved by the Committee on the Use of Live Animals in Teaching and Research (CULATR) of Li Ka Shing Faculty of Medicine, the University of Hong Kong Drug administration, and collection of serum and organs: Female Sprague-Dawley rats (16- to 20-month-old SD rats) were randomly divided into six groups (n=6): Group 1 was the control group treated with an equal volume of phosphate buffered saline (PBS) instead of the proteins by intraperitoneal injections; Groups 2, 3 and 4 were treated with DOI at three different dosages: 2.5, 5 and 10 mg/kg, respectively, by intraperitoneal injections; Group 5 received an oral administration of Premarin (12.4 mg/kg). Each rat was treated daily for 6 weeks. Serum samples were collected from the tail vein once every two weeks to obtain blood samples for measuring the serum levels of estrogen and progesterone. Their ovaries, the $1^{st}$ to $6^{th}$ lumbar vertebra, brains and breast tissues were collected at the end of the experiment and stored at −80° C. for further analysis. Their body weight and ovarian weight were measured.

Figure 12A:
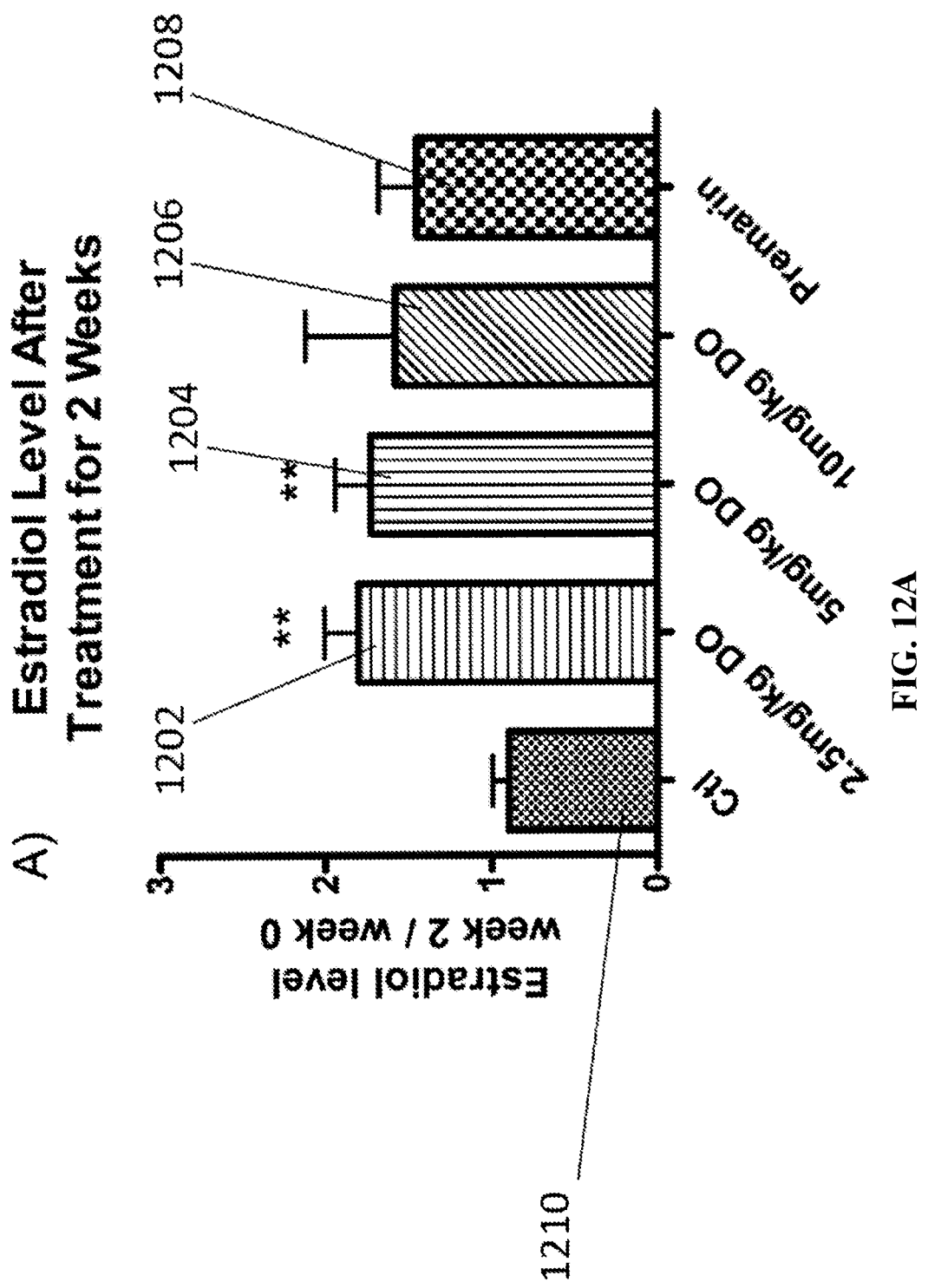
FIG. 12A is a graph of serum estrogen (estradiol) levels of Sprague-Dawley rats after a 2-week treatment with DOI peptide. Results are expressed as means±SEM, n=6. * $p<0.05$, ** $p<0.01$ compared with control by un-paired 1-test. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.

Detection of Serum Hormone Levels: Serum estradiol and progesterone levels were measured by means of an electrochemiluminescence immunoassay (Elecsys 2010; Roche Diagnostics), following the manufacturer's instruction. As shown in FIG. 12A, after treatment with 2.5 mg/kg (1202), 5 mg/kg (1204), and 10 mg/kg (1206) (daily intraperitoneal injection) of DOI peptide or Premarin (positive control, 1208, 12.4 mg/kg daily oral administration) for 2 weeks, the serum estradiol levels of the treated rats were respectively 180.1±20.73, 172.4±21.54, 157.7±54.39 and 144.9±22.92 percent (Mean±SEM, n=6) of the pre-treatment value. The serum estradiol level of negative control group 1210 (PBS) fell to 89.54±9.716 percent of the pre-treatment value. There was a significant increase in the fold change of serum estradiol level in 1202 (2.5 mg/kg) and 1204 (5 mg/kg) DOI peptide treated groups (p=0.0027 and 0.0057 respectively, un-paired t-test) compared with control group 1210 (FIG. 12A).

Figure 12B:
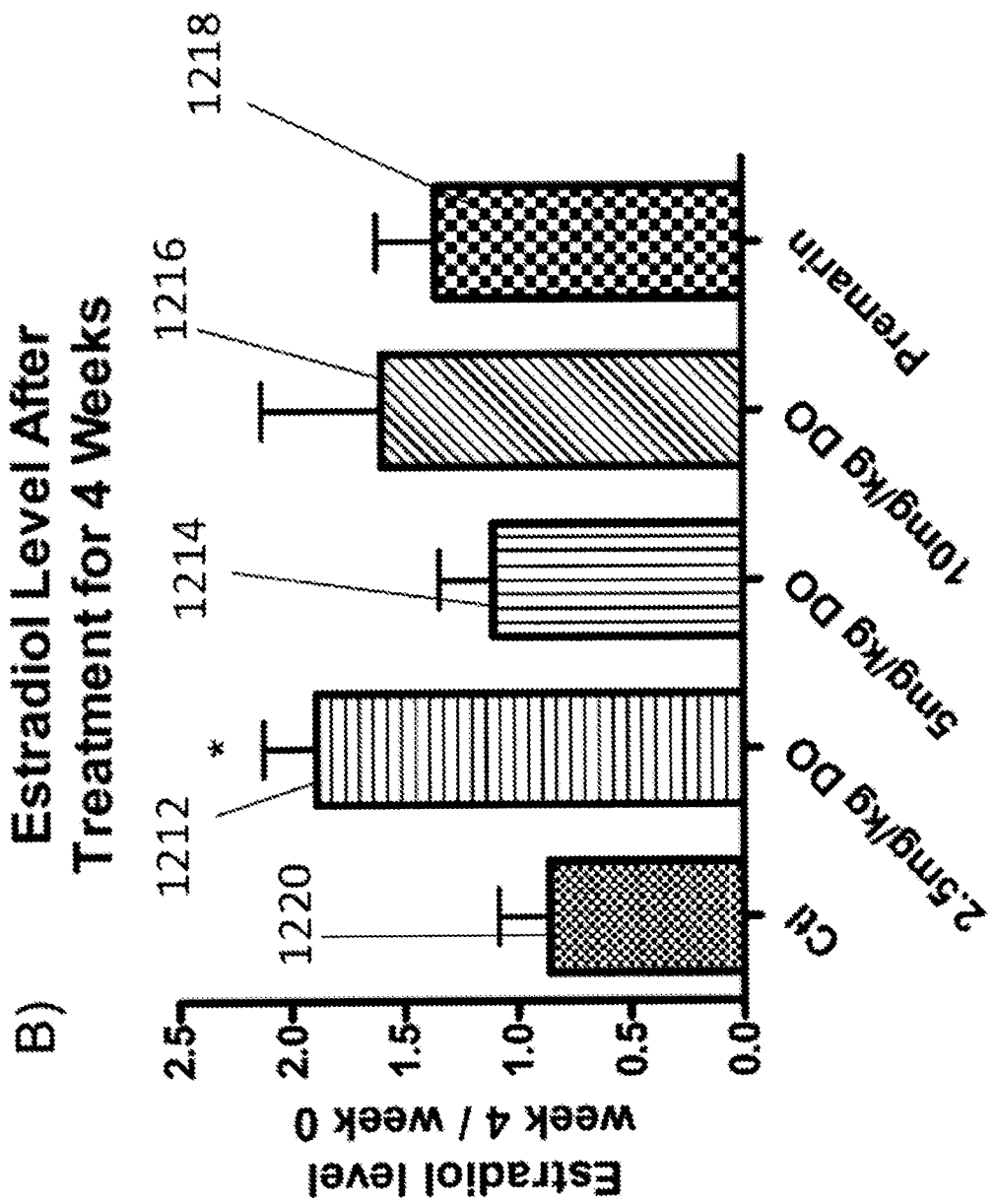
FIG. 12B is a graph of serum estrogen (estradiol) levels of Sprague-Dawley rats after a 4-week treatment period with DOI peptide. Results are expressed as means±SEM, n=6. * $p<0.05$, ** $p<0.01$ compared with control by un-paired t-test. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.

After treatment with 2.5 mg/kg (1212), 5 mg/kg (1214), 10 mg/kg (1216) daily by intraperitoneal injection of DOI peptide or Premarin (1218) (positive control 12.4 mg/kg daily oral administration) for 4 weeks, the serum estradiol levels of various groups of the Sprague-Dawley rats were respectively 188.8±23.54, 110.6±23.78, 159.9±53.02 and 135.8±26.2 percent (Mean±SEM, n=6) of the pre-treatment value (FIG. 12B). The serum estradiol level of negative control group 1220 (PBS) fell to 86.24±22.29 percent of the pre-treatment value. There was significant increase in the fold change of serum estradiol level in 1212 (2.5 mg/kg DOI treated group) (p=0.0101, un-paired t-test) compared with control group 1220 (FIG. 12B)

Figure 12C:
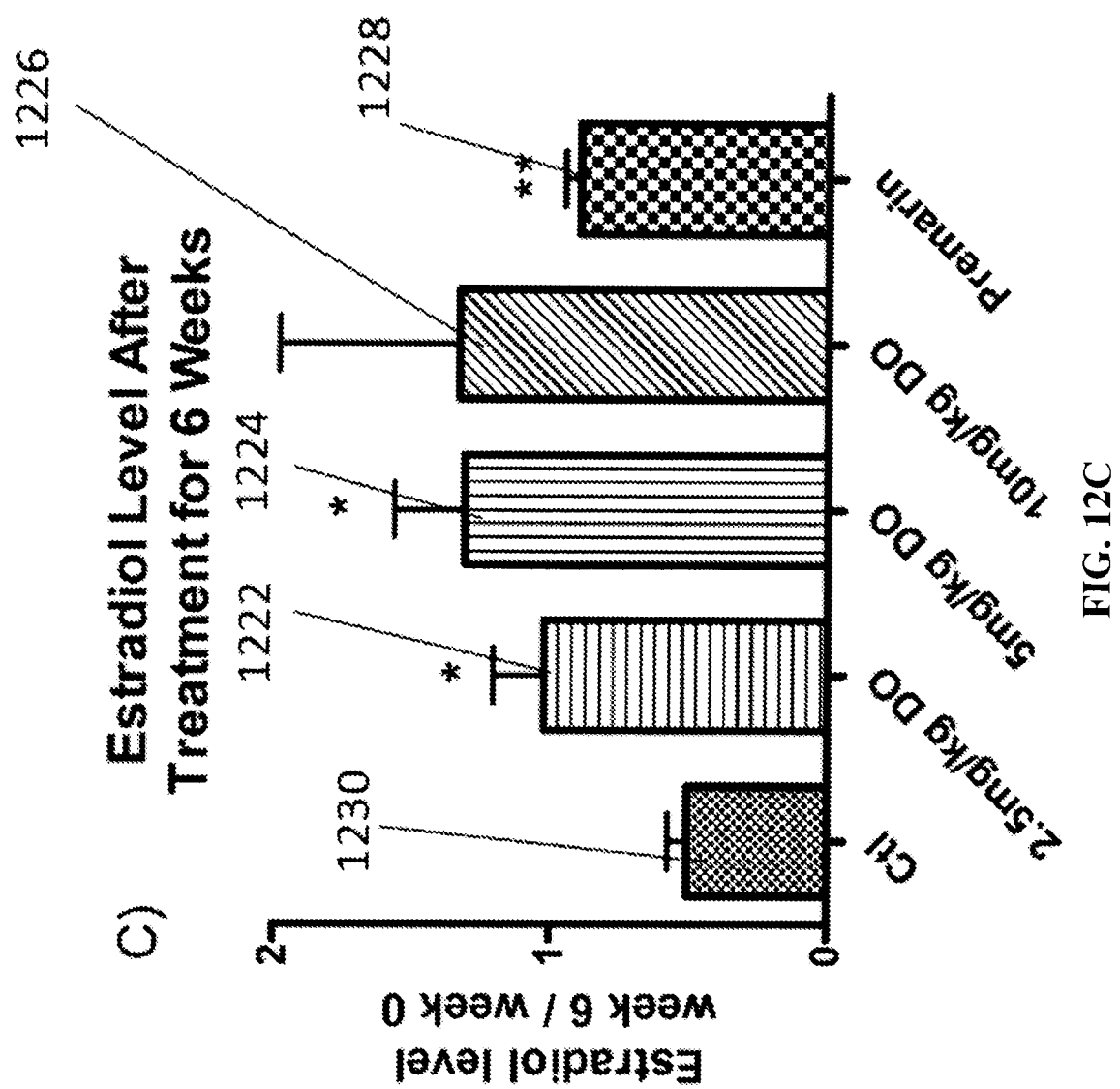
FIG. 12C is a graph of serum estrogen (estradiol) levels of Sprague-Dawley rats after a 6-week treatment period with DOI peptide. Results are expressed as means±SEM, n=6. * $p<0.05$, ** $p<0.01$ compared with control by un-paired t-test. Ctl: old control group receiving intraperitoneal injections of PBS; Premarin: positive control group treated with Premarin (12.4 mg/kg) by oral administration; DOI treated group receiving daily intraperitoneal injections of DOI at 2.5 mg/kg, 5 mg/kg and 10 mg/kg, respectively.

After treatment with 2.5 mg/kg (1222), 5 mg/kg (1224), and 10 mg/kg (1226) by intraperitoneal injection of DOI or Premarin (1228) (positive control 12.4 mg/kg daily by oral administration) for 6 weeks, the serum estradiol levels of various groups of the Sprague-Dawley rats were respectively 102.4±18.26, 133.1±25.62, 133±65.24 and 89.82±5.24 percent (Mean±SEM, n=6) of the pre-treatment value, as shown in FIG. 12C. The serum estradiol level of negative control group 1230 (PBS) fell to 50.64±6.88 percent of the pre-treatment value. There was significant increase in the serum estradiol level in both 1222 (2.5 mg/kg) and 1224 (5 mg/kg) DOI peptide treated groups and 1228, the Premarin treated group, (p=0.0242, 0.0126 and 0.0011 respectively, un-paired t-test) compared with negative control group 1230, shown in FIG. 12C.

Figure 12D:
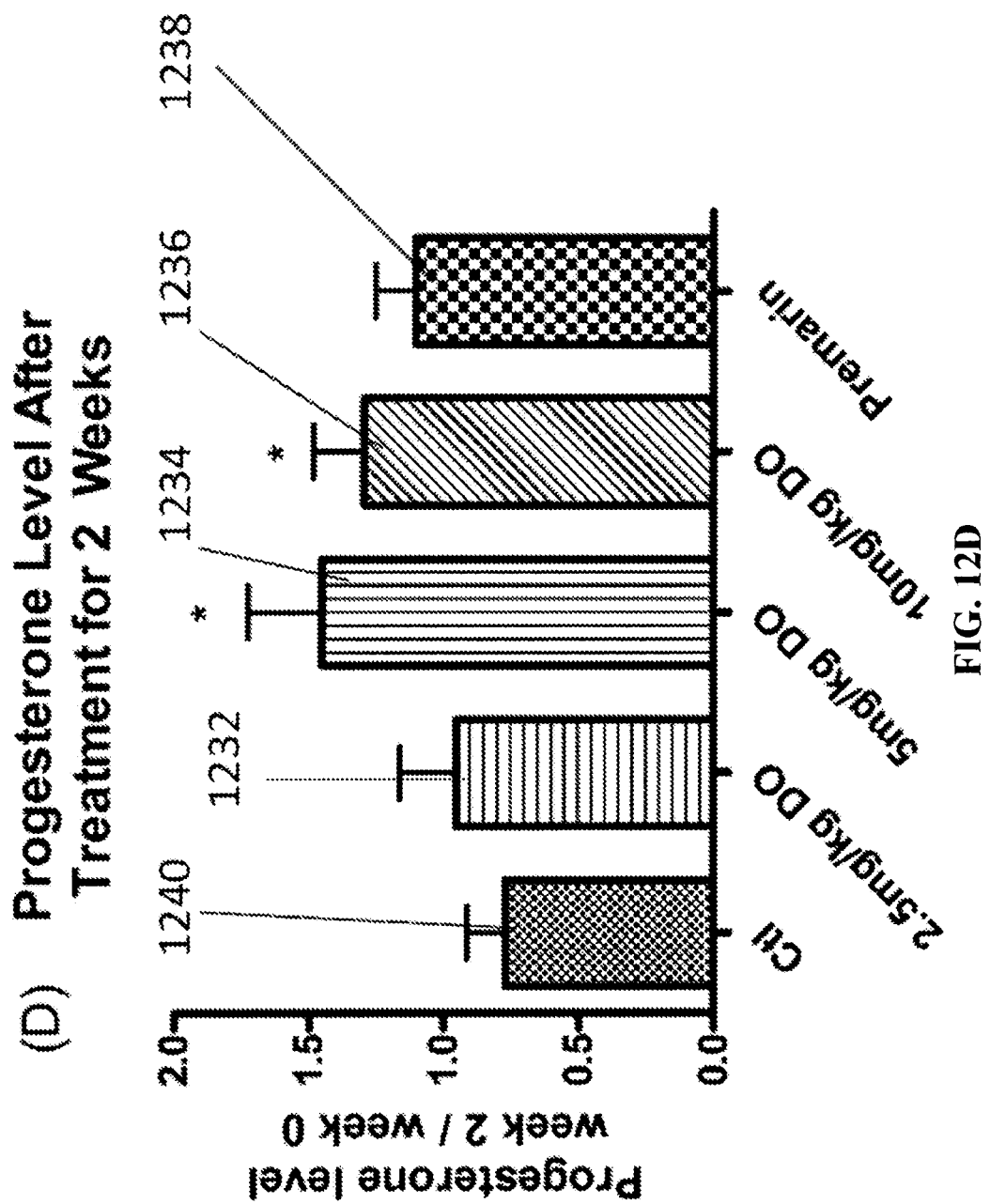
FIG. 12D is a graph of serum progesterone levels of Sprague-Dawley rats after a 2-week treatment period with DOI peptide. Results are expressed as means±SEM, n=6. * $p<0.05$, ** $p<0.01$ compared with control by un-paired Nest. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.

After treatment by daily intraperitoneal injection of DOI peptide or Premarin 1238 (positive control 12.4 mg/kg daily oral administration) for 2 weeks, the serum progesterone levels of various groups of the Sprague-Dawley rats, shown in FIG. 12D, were respectively 95.31±21.02% (1232), 145.3±27.26% (1234), 129.4±18.76% (1236) and 110.5±14.8% (1238) (Mean±SEM, n>5) of the pre-treatment value for animals given 2.5 mg/kg, 5 mg/kg, 10 mg/kg of DOI peptide and Premarin. The serum progesterone level of negative control group 1240 (PBS) fell to 77.21±14.33% of the pre-treatment value. There was significant increase in the fold change of serum progesterone level in 5 mg/kg and 10 mg/kg DOI peptide treated groups (p=0.039 and 0.047 respectively, un-paired t-test) compared with control group 1240.

Figure 12E:
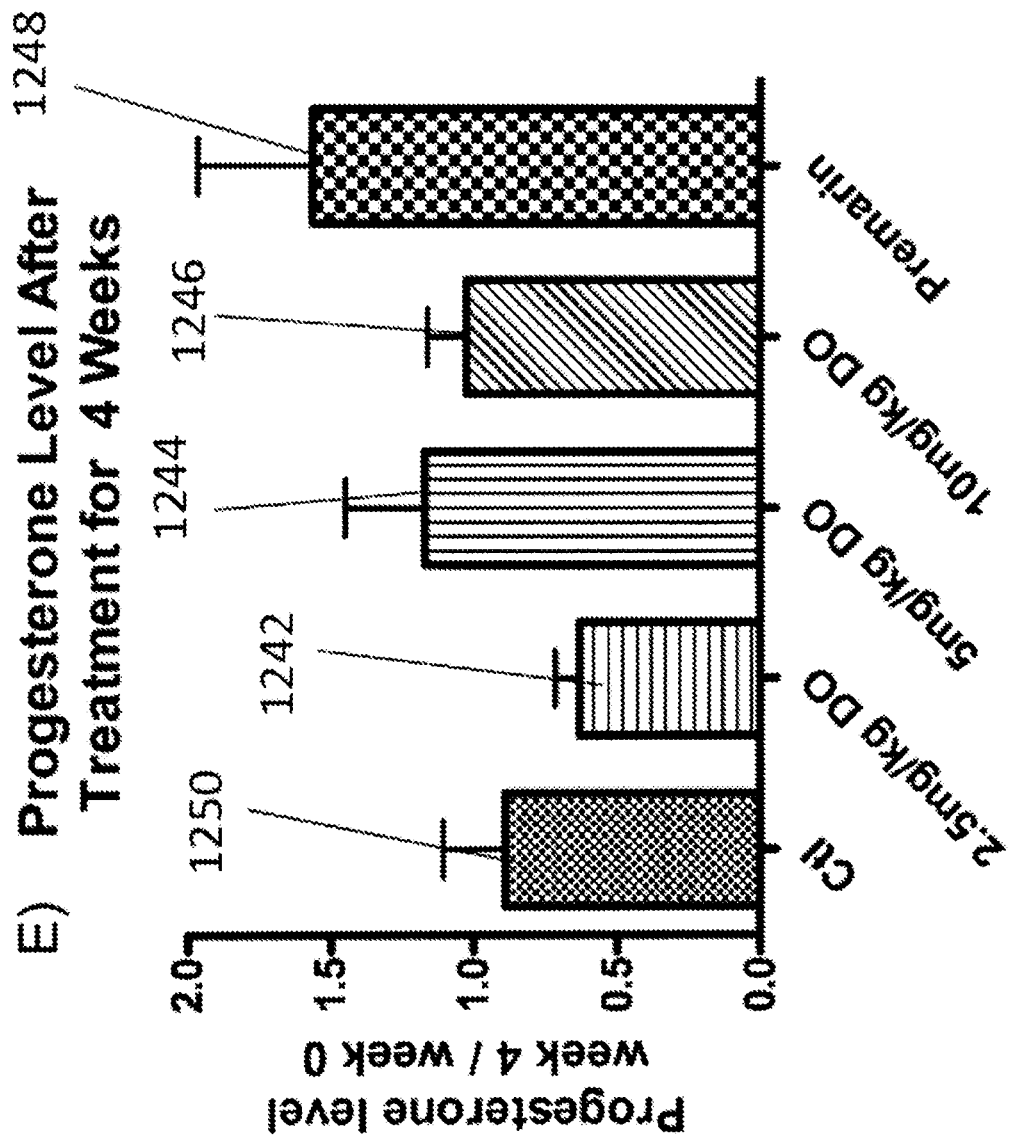
FIG. 12E is a graph of serum progesterone levels of Sprague-Dawley rats after a 4-week treatment period with DOI peptide. Results are expressed as means±SEM, n=6. * $p<0.05$, ** $p<0.01$ compared with control by un-paired t-test. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.
Figure 12F:
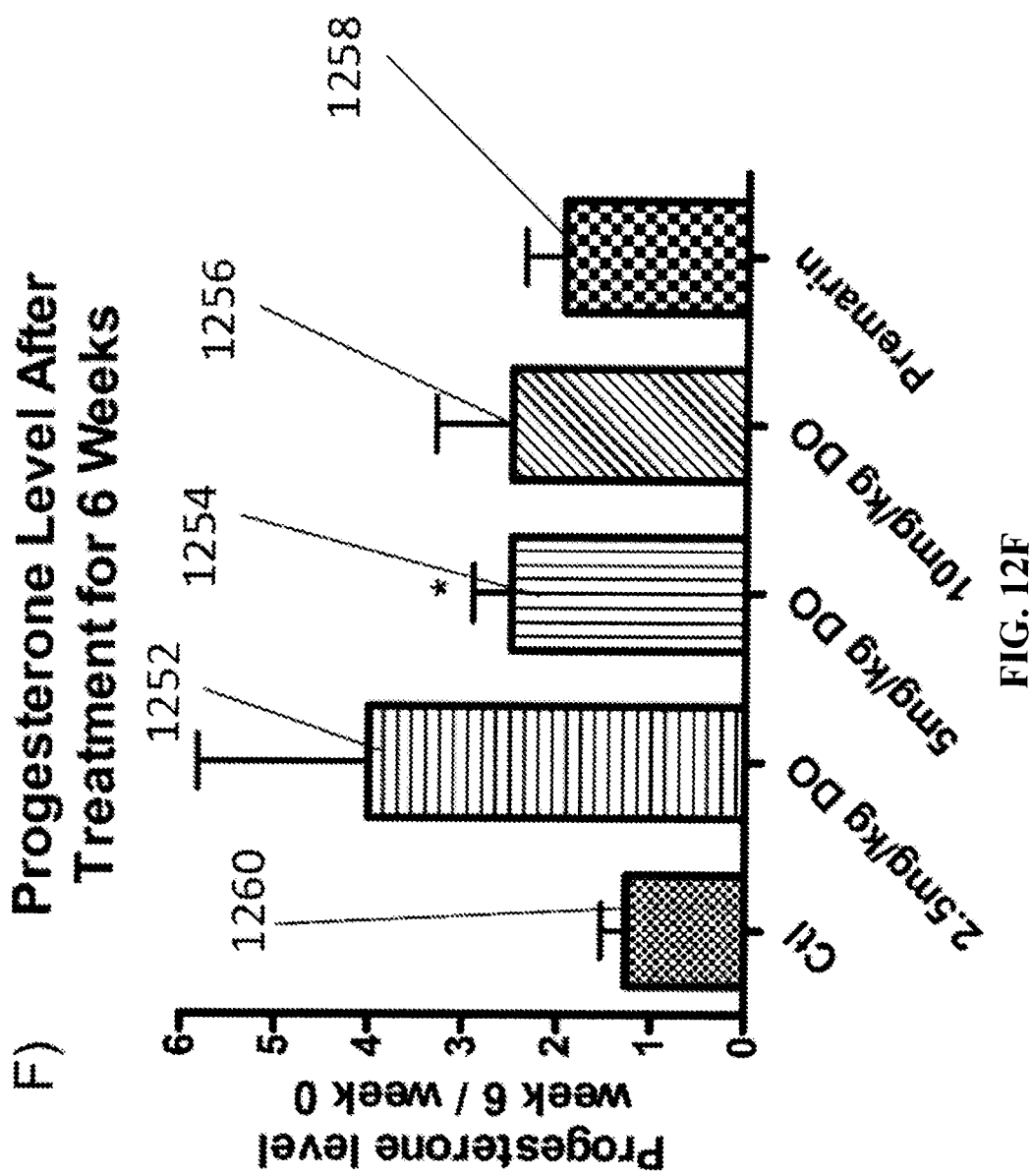
FIG. 12F is a graph of serum progesterone levels of Sprague-Dawley rats after a 6-week treatment period with DOI peptide. Results are expressed as means±SEM, n=6. * $p<0.05$, ** $p<0.01$ compared with control by un-paired t-test. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.

Following daily treatment with 2.5, 5, and 10 mg/kg of DOI peptide for 4 weeks, the serum progesterone levels of the various groups of rats were respectively 63.12±8.509% (1242), 117.0±28.20% (1244), 102.5±13.50% (1246) (Mean±SEM, n>5) of the pre-treatment value (FIG. 12E). A dose of 12.4 mg/kg daily of Premarin elevated serum progesterone to 156.6±40.07% (1248) (Mean±SEM, n>5) of the pre-treatment value. The serum progesterone level of negative control group 1250 (PBS) fell to 89.16±21.59% of the pre-treatment value.

After treatment with various doses (2.5 mg/kg, 5 mg/kg, 10 mg/kg daily intraperitoneal injection) of DOI and Premarin (positive control 12.4 mg/kg daily oral administration) for 6 weeks, the serum progesterone levels of various groups of the Sprague-Dawley rats were respectively 400.4±182.6% (1252), 249.9±41.0% (1254), 249.8±80.89% (1256) and 194.9±41.96% (1258) (Mean±SEM, n>5) of the pre-treatment value. The serum progesterone level of negative control group 1260 (PBS) rose to 126.4±26.45% of the pre-treatment value. There was significant increase in the fold change of serum progesterone level in the 5 mg/kg DOI peptide treated group 1254 (p=0.022, un-paired t-test) compared with control group 1260. Determination of estrogen-related gene expression by real time PCR: Total RNA was extracted from ovarian granulosa cells and rat ovaries with High Pure RNA Isolation Kit (Roche Applied Science) following manufacturer's instruction. cDNA was synthesized from total RNA using First Strand cDNA Synthesis Kit (Fermentas) following manufacturer's instruction. Real time PCR was performed using a LightCycler 480 Real-Time PCR system (Roche Applied Science). Primers for ovarian CYP-19 were (Forward: 5' GAGAGTTCATGAGAGTCTGGATCA (SEQ ID NO: 2), Reverse: 5' GATATAGTTGCTGTGCTTCATCA (SEQ ID NO: 3)). Primers for ovarian FSHR were (Forward: 5' GAAAGGATCATTTGCTGGATTT (SEQ ID NO: 4), Reverse: 5' CTTCCAAGACATCATTCTGAGAGA (SEQ ID NO: 5)). Primers for ovarian PKA were (Forward: 5' TGGATGTGATCGGGGAAA (SEQ ID NO: 7), Reverse: 5' AAGCTGTCGGCCTTTTCA (SEQ ID NO: 8)). Primers for ovarian PKB were (Forward: 5' AAAACTTTCTTCGTCCACACG (SEQ ID NO: 9), Reverse: 5' GGACTGCTCTGGTACTGT-TGC (SEQ ID NO: 10)). Primers for ovarian PKC were (Forward: 5' GCATAGACTGGGACCTGCTT (SEQ ID NO: 11), Reverse: 5' CCAGGCCATAGTCATCTGTG (SEQ ID NO: 12)).

The mRNA expression level of ovarian CYP-19 aromatase in ovaries from Sprague-Dawley rats treated with DOI peptide or Premarin was determined. The animals were treated for 6 weeks; DOI peptide was administered by intraperitoneal injection, and Premarin was given orally. A control group of animals received phosphate buffered saline (PBS) by intraperitoneal injection. The results are presented in graph 1500 in FIG. 15. Expression of mRNA for ovarian CYP-19 aromatase in rats treated with 2.5 mg/kg (1502), 5 mg/kg (1504), and 10 mg/kg (1506) of DOI peptide was 0.751±0.108, 0.257±0.062, and 0.327±0.025, respectively, expressed as $\log_{10}$ fold difference. Expression of mRNA in animals given Premarin (12.4 mg/kg daily), 1508, was 0.290±0.051 $\log_{10}$ fold difference. There was a significant increase in the mRNA expression level in 1502 (2.5 mg/kg) (p<0.01), 1504 (5 mg/kg) (p<0.05), 1506 (10 mg/kg) (p<0.05) DOI peptide treated groups and Premarin treated group 1508 (p<0.05) compared with control group 1510 by one way ANOVA statistical analysis followed by a Dunnett post-test.

Expression of mRNA for FSHR was measured in Sprague-Dawley rats after 6 weeks of treatment with DOI peptide. As shown in graph 1600 of FIG. 16, the mRNA expression level of FSHR in ovaries from Sprague-Dawley rats treated with DOI peptide at 2.5 mg/kg (1602), 5 mg/kg (1604), 10 mg/kg (1606) and Premarin at 12.4 mg/kg (1608) was measured and expressed as $\log_{10}$ fold difference. The mRNA expression levels were 0.370±0.078 (1602), 0.221±0.101 (1604), 0.288±0.053 (1606) and 0.382±0.068 (1608) respectively. There was a significant increase in the mRNA expression level in groups 1602 (p<0.05), 1606 (p<0.05), and Premarin treated group 1608 (p<0.05) compared with control group 1610. Statistical analysis was performed using one-way ANOVA.

Determination of the estrogen-related protein by Western blotting analysis: Protein was extracted from ovarian granulosa cells, ovaries and breast of Sprague-Dawley rats using RIPA buffer (Sigma Aldrich) with complete protease inhibitor cocktail tablets (Roche Applied Science). 20 µg of denatured proteins per sample were separated on SDS-PAGE and transferred to PVDF membranes. Immunoblotting was performed using specific anti-FSHR (sc-13935, Santa Cruz Biotechnology, Inc), anti-aromatase (sc-14245, Santa Cruz Biotechnology, Inc), anti-phospho-PKA (#04-404, upstate), anti-p-AKT1/2/3 (ser 473)-R (sc-7985-R, Santa Cruz Biotechnology, Inc) and anti-phospho-PKC (Thr555/Thr563, upstate, new part of Millipore) antibodies for proteins from ovarian granulosa cells and ovaries, with anti-GAPDH antibody as internal standard, followed by incubation with horseradish peroxidase-conjugated secondary antibody. Protein was extracted from breast tissue, Immunoblotting was performed using specific anti-aromatase antibodies (sc-14245, Santa Cruz Biotechnology, Inc) for evaluating the breast cancer risk. Chemiluminescence detection (GE Bio-health) was accomplished with the Bio-Rad Chemi Doc™ EQ densitometer (Bio-rad) and quantified by Bio-Rad Quantity One 1-D Analysis software (Bio-Rad laboratories, Hercules, USA).

Figure 13:
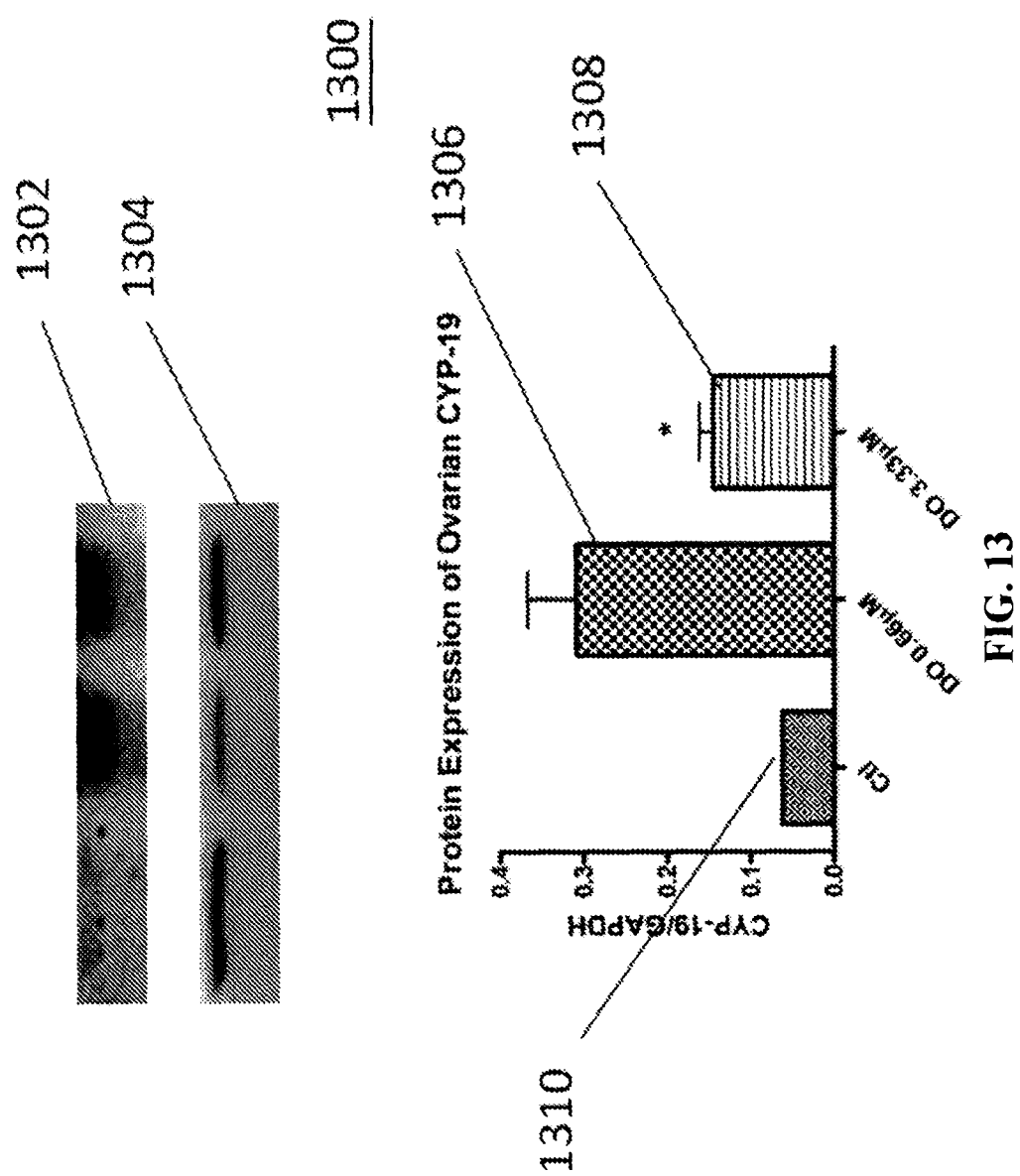
FIG. 13 is a graph showing protein expression of ovarian CYP-19 aromatase in granulosa cells.

Protein expression of ovarian CYP-19 aromatase (also known as estrogen synthetase) was compared to expression of glyceraldehyde 3-phosphate dehydrogenase (GAPDH) in granulosa cells treated with DOI peptide. Protein was extracted from granulosa cells and ovaries of Sprague-Dawley rats using RIPA buffer (Sigma Aldrich) with Complete Protease Inhibitor Cocktail Tablets (Roche Applied Science). 20 µg of denatured proteins per sample were separated on SDS-PAGE and transferred to PVDF membranes. Immunoblotting was performed using specific anti-FSHR (follicle stimulating hormone receptor) and anti-ovarian aromatase antibodies, with anti-GAPDH antibody as an internal standard, followed by incubation with horseradish peroxidase-conjugated secondary antibody. Chemiluminescence detection (GE Bio-health, Princeton, N.J.) was accomplished with the Bio-Rad Chemi Doc™ EQ densitometer (Bio-rad) and quantified by Bio-Rad Quantity One software (Bio-Rad laboratories, Hercules, USA). Results are shown in FIG. 13.

Specific induction of the CYP-19 protein compared to GAPDH is apparent from a comparison of the thickness of bands 1302 (CYP-19) and 1304 (GAPDH) obtained from SDS PAGE. The protein expression of ovarian CYP-19/GAPDH in granulosa cells treated with DOI at 0.66 µM (1304) and 3.33 µM (1306) was 0.309±0.059 and 0.146±0.016 respectively, as shown in graph 1300. There was a significant increase in the protein expression in 3.33 µM DOI peptide treated group 1306 (p=0.0347, un-paired t-test) compared with control group 1310 (0.062±0.001).

Figure 14:
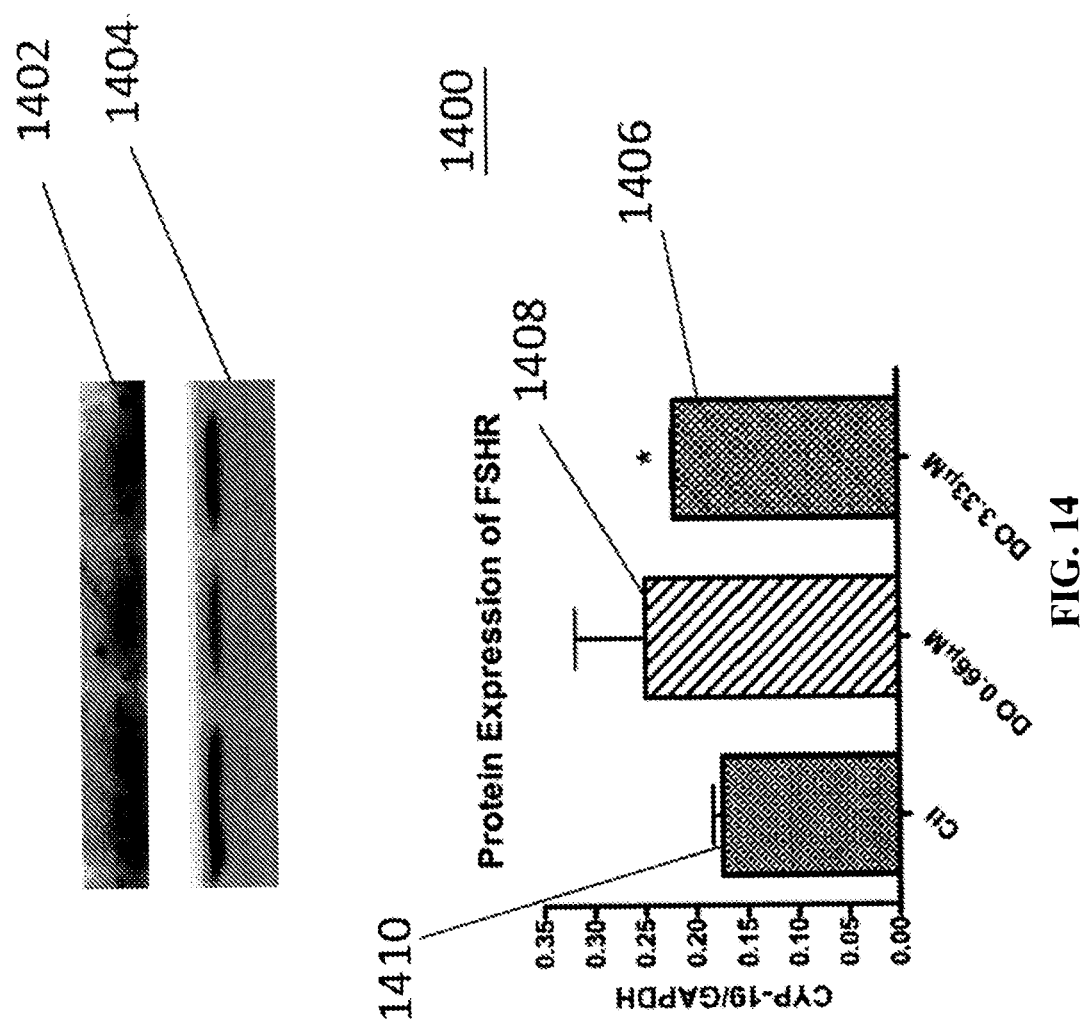
FIG. 14 is a graph showing protein expression of FSHR in granulosa cells.

Similarly, expression of follicle-stimulating hormone receptor (FSHR) and GAPDH in granulosa cells treated with DOI peptide at 0.66 µM and 3.33 µM was measured. The results, shown in FIG. 14, indicate that FSHR expression (band 1402) increased compared to GAPDH expression (band 1404). Expression of FSHR/GAPDH in granulosa cells treated with DOI protein at 0.66 µM (1408) and 3.33 µM (1406) was 0.249±0.069 and 0.220±0.002 respectively. There was a significant increase in the protein expression in the 3.33 µM DOI peptide treated group 1406 (p=0.0391, un-paired t-test) compared with the control group 1410 (0.174±0.009) as shown in FIG. 14.

Figure 17:
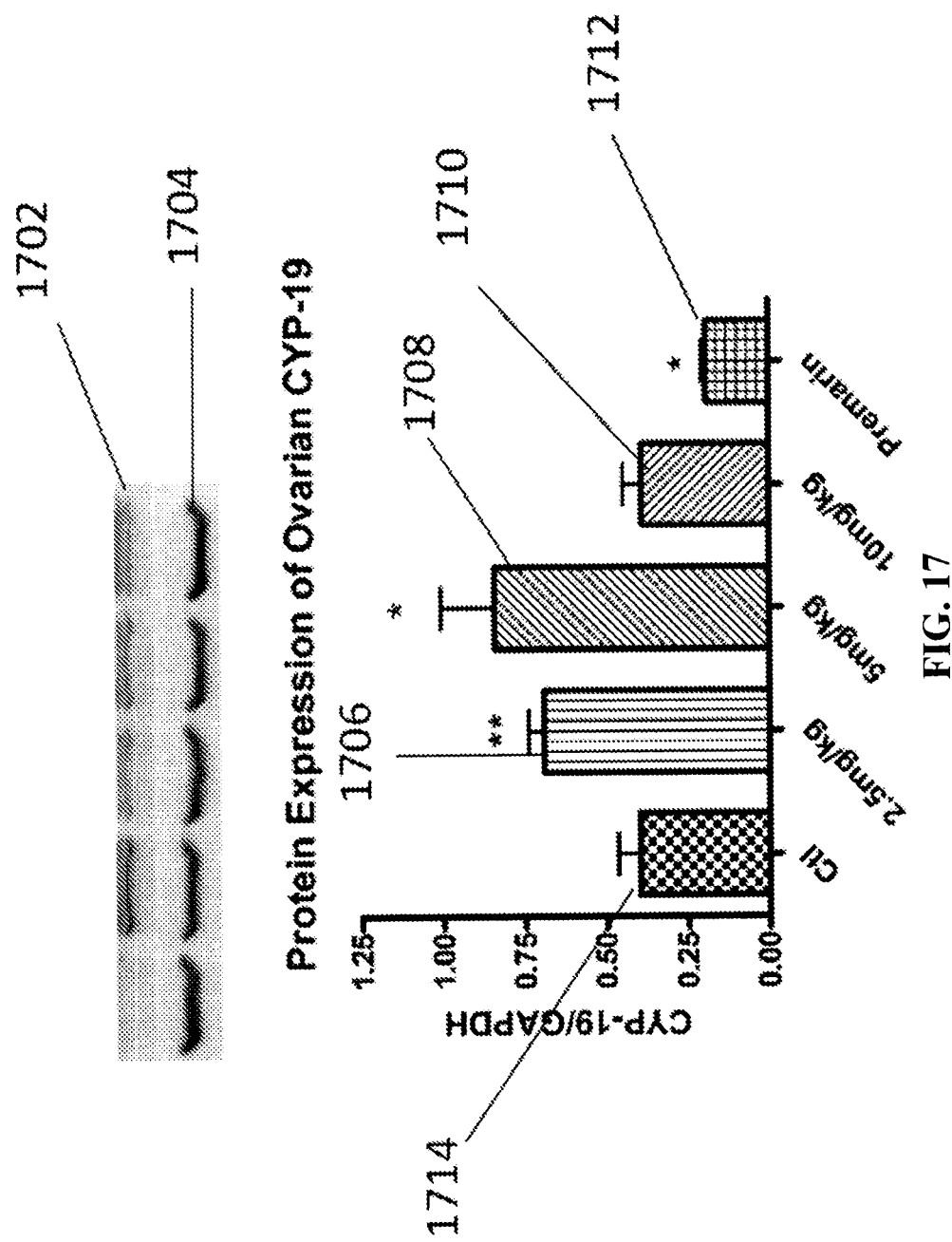
FIG. 17 is a graph showing the protein expression level of ovarian CYP-19 aromatase in ovaries from Sprague-Dawley rats after a 6-week treatment with DOI peptide. Results are expressed as means±SEM, n=6. * $p<0.05$, $p<0.01$, *$p<0.001$ compared with control group by One Way ANOVA followed by Dunnett's Multiple Comparison Test. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.

The protein expression level of ovarian CYP-19 aromatase was measured and compared to expression of GAPDH in ovaries from Sprague-Dawley rats treated with DOI peptide. DOI peptide was administered to female Sprague-Dawley rats at 2.5 mg/kg, 5 mg/kg, 10 mg/kg daily for 6 weeks. A control group of animals received 12.4 mg/kg Premarin daily for 6 weeks. A negative control group of animals received PBS injections daily for 6 week. The results are shown in FIG. 17. CYP-19 1702 and GAPDH 1704 expression were analyzed using SDS PAGE. The ratio of CYP-19/GAPDH was determined to be 0.691±0.048 (1706), 0.842±0.167 (1708), 0.391±0.058 (1710) and 0.192±0.015 (1712) for doses 2.5 mg/kg, 5 mg/kg, 10 mg/kg, and Premarin, respectively. There was a significant increase in the protein expression level in 2.5 mg/kg and 5 mg/kg DOI treated groups 1706 (p=0.0051) and 1708 (p=0.0326), un-paired t-test) compared to control group 1714 (0.398±0.066). There was a significant decrease in Premarin treated group 1712 (p=0.0128, un-paired t-test) compared with control group 1714.

Figure 18:
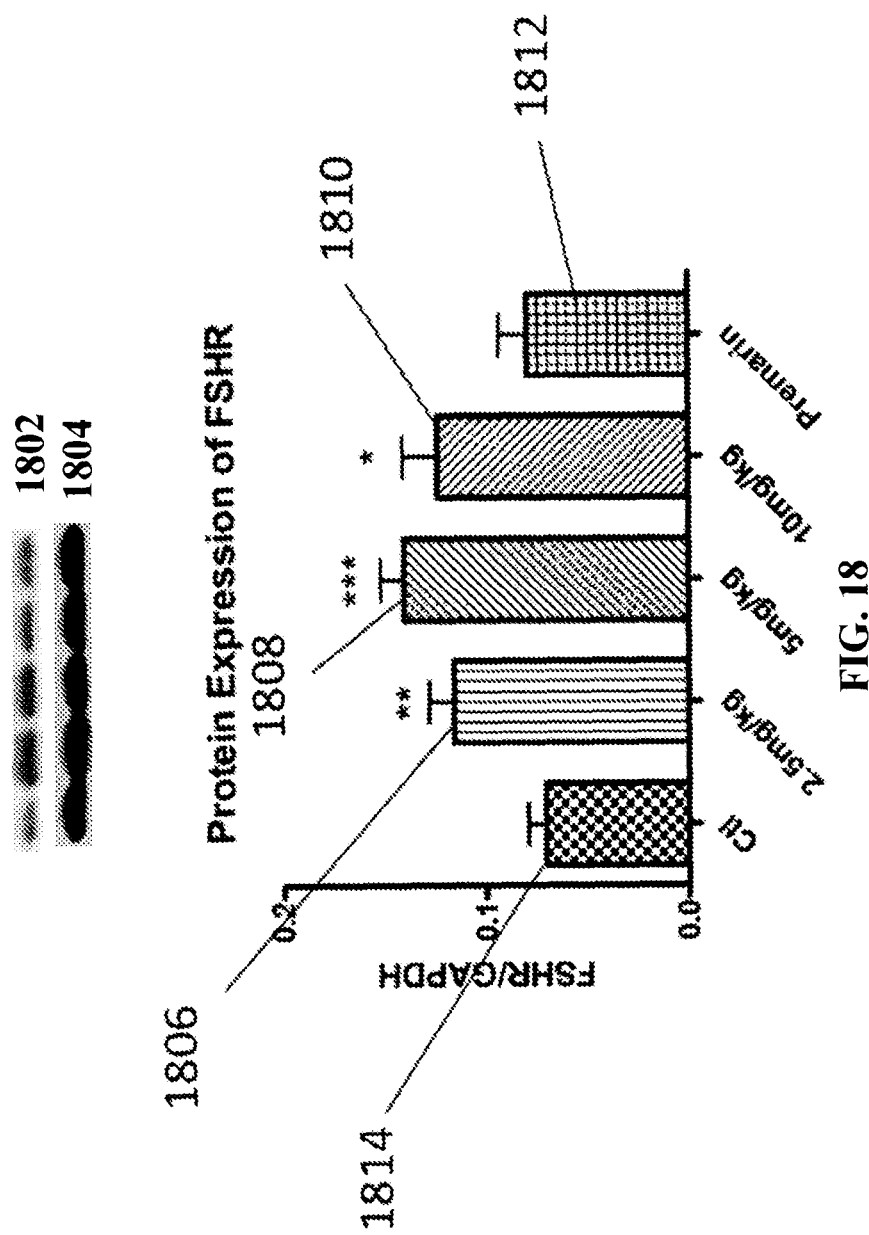
FIG. 18 is a graph showing the protein expression level of FSHR in ovaries from Sprague-Dawley rats after a 6-week treatment with DOI peptide. Results are expressed as means±SEM, n=6. * p<0.05, p<0.01, *p<0.001 compared with control group by One Way ANOVA followed by Dunnett's Multiple Comparison Test. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.

FSHR expression was measured and compared to expression of GAPDH in the ovaries of Sprague-Dawley rats after a 6 week treatment period with DOI peptide, Premarin, or PBS. The results are shown in FIG. 18. The protein expression level of FSHR (1802)/GAPDH (1804) in ovaries from rats treated with DOI peptide at 2.5 mg/kg (1806), 5 mg/kg (1808), 10 mg/kg (1810) and Premarin (1812) was 0.116±0.012, 0.141±0.012, 0.124±0.017 and 0.079±0.014 respectively. There was significant increase in the protein expression level in 1806 (2.5 mg/kg), 1808 (5 mg/kg) and 1810 (10 mg/kg) DOI peptide treated groups (p=0.0099, 0.0004 and 0.0167 respectively, un-paired t-test) compared with control group 1814 (0.071±0.009).

In one embodiment, the DOI peptide isolated from Chinese yam tuber (*Dioscorea opposita*) increases the endogenous biosynthesis of estrogen and progesterone by up-regulating synthesis of follicle stimulating hormone receptor (FSHR) (FIGS. 14, 16, 18) and ovarian CYP-19 aromatase (FIG. 13, 15, 17). Both estrogen (FIG. 8, 12) and progesterone levels (FIG. 12) are maintained at premenopausal levels. In addition, progesterone and estrogen synthesis, mediated by FSHR and CYP-19 aromatase, are regulated by the feedback mechanism of the hypothalamus-pituitary axis. In one embodiment menopausal syndrome is relieved by slowing the decline of serum estrogen and progesterone levels (FIG. 12). MTT Assay: The MTT Cell Proliferation Assay is a quantitative, convenient method for evaluating a cell population's response to external factors. Results may show an increase in cell growth, no effect, or a decrease in growth due to necrosis or apoptosis.

BT 483 and OVCA-429 cancer cells were serum starved for 24 hours prior to drug treatment. The DOI peptide was then added in complete growth medium at the concentration of 1 nM, 10 nM and 100 nM for 48 hours, followed by incubation with MTT solution for 3 hours. Formazan crystals were dissolved by DMSO. Absorbance at O.D. 540 nm was measured with a microplate reader (Model 680, Bio-Rad). Percentage proliferation relative to the control was calculated.

Figure 19:
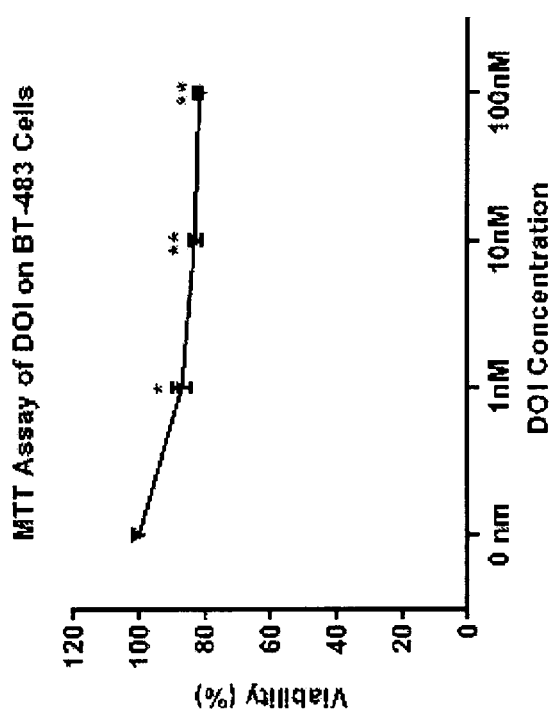
FIG. 19 is a graph showing the effect of DOI on proliferation of BT-483 breast cancer cells after treatment with DOI for 48 hours. Results are expressed as means±SEM, n=3.  p<0.01, * p<0.001 compared with control group by un-paired Nest.
Figure 20:
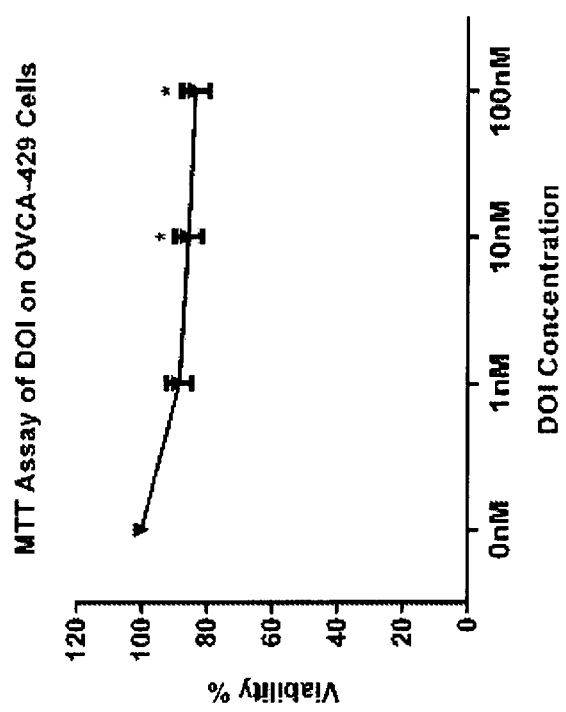
FIG. 20 is a graph showing the effect of DOI on proliferation of OVCA-429 ovarian cancer cells after treatment with DOI for 48 hours. Results are expressed as means±SEM, n=3.  p<0.01, * p<0.001 compared with control group by un-paired Nest.
Figure 21:
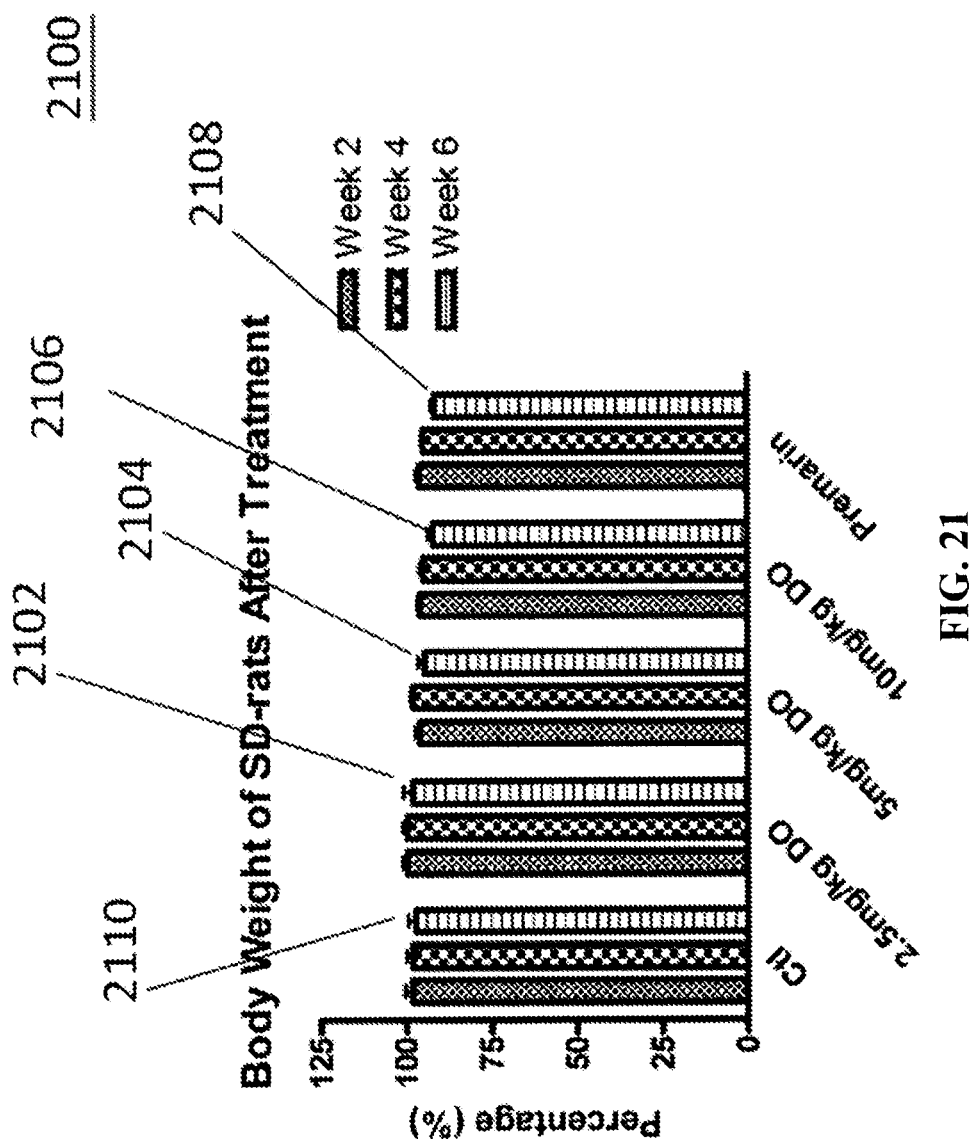
FIG. 21 is a graph showing the body weight of rats after treatment with DOI peptide.

In one embodiment, DOI peptide inhibited the proliferation of both BT-483 breast cancer cells (FIG. 19) and OV-429 cells (FIG. 20) in a dose dependent fashion. As indicated by FIG. 19, incubation of BT-483 cells with DOI peptide at a concentration of 100 nM for 48 hours decreased the proliferation of BT-483 breast cancer cells to 78.65±5.502% of control value. As shown in FIG. 20, incubation of OV-429 ovarian cancer cells decreased cellular proliferation to 83.81±1.899%. Effect of DOI Peptide on Body Weight: The body weights of female Sprague-Dawley rats given either DOI peptide or Premarin were determined after 6 weeks of treatment. DOI peptide was administered at doses of 2.5 mg/kg, 5 mg/kg, 10 mg/kg, and Premarin at a dose of 12.54 mg/kg. Results are shown in graph 1700, FIG. 21. Body weights after 2, 4, and 6 weeks of treatment were compared with the pre-treatment value. The final body weights after 6 weeks of treatment were found to be 95.27±3.76% (2102), 90.78±4.15%, (2104), 92.17±1.46% (2106) for DOI peptide doses of 2.5 mg/kg, 5 mg/kg, 10 mg/kg, respectively, and 91.72±0.98% (2108) for Premarin. There was no significant difference with the control group (2110) (97.31±2.32) and any of the treated groups.

Measurement of bone mineral density and micro-architecture by Micro-CT scanning: For sample preparation, lumbar vertebrae including soft tissue from Sprague-Dawley rats after treatment for 6 weeks were harvested and wrapped in normal saline gauze (0.9%). They were then stored at −80 degree Celsius until measurement. The specimens were thawed at room temperature prior to evaluation of bone status using an In Viva MicroCT 40 computed tomography system (Scanco Medical, Basserdorf, Switzerland). For image acquisition, the lumbar vertebrae wrapped with saline gauze were placed in a sample holder and the long axis aligned with the axis of rotation of the X-ray gantry. A scout view was obtained which was used to identify the 2nd lumbar vertebra (L2) and determine the scanning location. A set of 100 contiguous axial slices at an isotropic resolution of 21 μm was prescribed at the L2 mid-vertebral body. Exposure parameters were set at X-ray tube peak voltage of 70 kVp and tube current of 114 μA with integration time of 300 ms. Calibration of X-ray attenuation to bone mineral density (mg/cc of hydroxyapatite, HA) with the micro CT scanner was carried out weekly using a standardized phantom. For Image processing and analysis, a Gaussian filter (with a support=2 and sigma=1.2) was used to reduce the image noises. Precise contouring was performed in each of the slices by drawing the region of interest manually a few voxels away from the endocortical boundary. This was then followed by segmentation using a global threshold of 250 for all the study groups so as to separate the mineral tissues from non-mineralized tissues. Volume rendering of these segmented slices was performed to provide a three-dimensional (3D) image. The apparent trabecular bone mineral density and its bone micro-architecture were automatically evaluated using the built-in program of the micro CT with the model independent direct 3D morphometry. The bone micro-architecture including apparent trabecular bone mineral density, bone volume fraction, trabecular number, trabecular thickness, trabecular separation and structural model index were reported. Table 3 lists the bone micro-architecture parameters used to evaluate bone mineralization and provide a measure of anti-osteoporotic activity.

TABLE 3

List of bone micro-architecture parameters used to evaluate bone mineralization and provide a measure of anti-osteoporotic activity

| Abbreviation | Variable | Description | Standard unit |
|---|---|---|---|
| tBMD ↑ | Apparent trabecular bone mineral density | Bone mineral density of the total bone volume including the bone marrow | mg/cc of HA |
| BV/TV ↑ | Bone volume fraction | Ratio of the segmented bone volume to the total volume of the region of interest | % |
| Tb.N ↑ | Trabecular number | Measure of the average number of trabecular per unit length | 1/mm |
| Tb.Th ↑ | Trabecular thickness | Mean thickness of trabeculae, assessed using direct 3D methods | mm |
| Tb.Sp ↓ | Trabecular separation | Mean distance between trabeculae, assessed using direct 3D methods | mm |
| SMI ↓ | Structure model index | An indicator of the structure of trabeculae; SMI will be 0 for parallel plates and 3 for cylindrical rods | dimensionless |

Source: (Bouxsein, Boyd et al. 2010)

The anti-osteoporotic activity of DOI peptide was evaluated in female Sprague-Dawley rats by comparing the bone calcification effects of DOI peptide to the hormone replacement drug, Premarin and Raloxifene. Raloxifene is a drug that prevents and treats osteoporosis by mimicking the effects of estrogen to increase the density (thickness) of bone. Premarin, and Raloxifene were used as positive controls.

Groups of 3-6 animals per group were dosed daily with 2.5 mg/kg 5 mg/kg, 10 mg/kg of DO peptide, 12.4 mg/kg Premarin, and 25.56 mg/kg Raloxifene. A negative control group received daily doses of PBS. After 6 weeks of dosing, the L2 vertebra of the animals was harvested and examined for apparent trabecular bone mineral density (FIG. 22), bone volume fraction (FIG. 23), trabecular number (FIG. 24), trabecular thickness (FIG. 25), structure model index (FIG. 26), and trabecular separation (FIG. 27).

Figure 22:
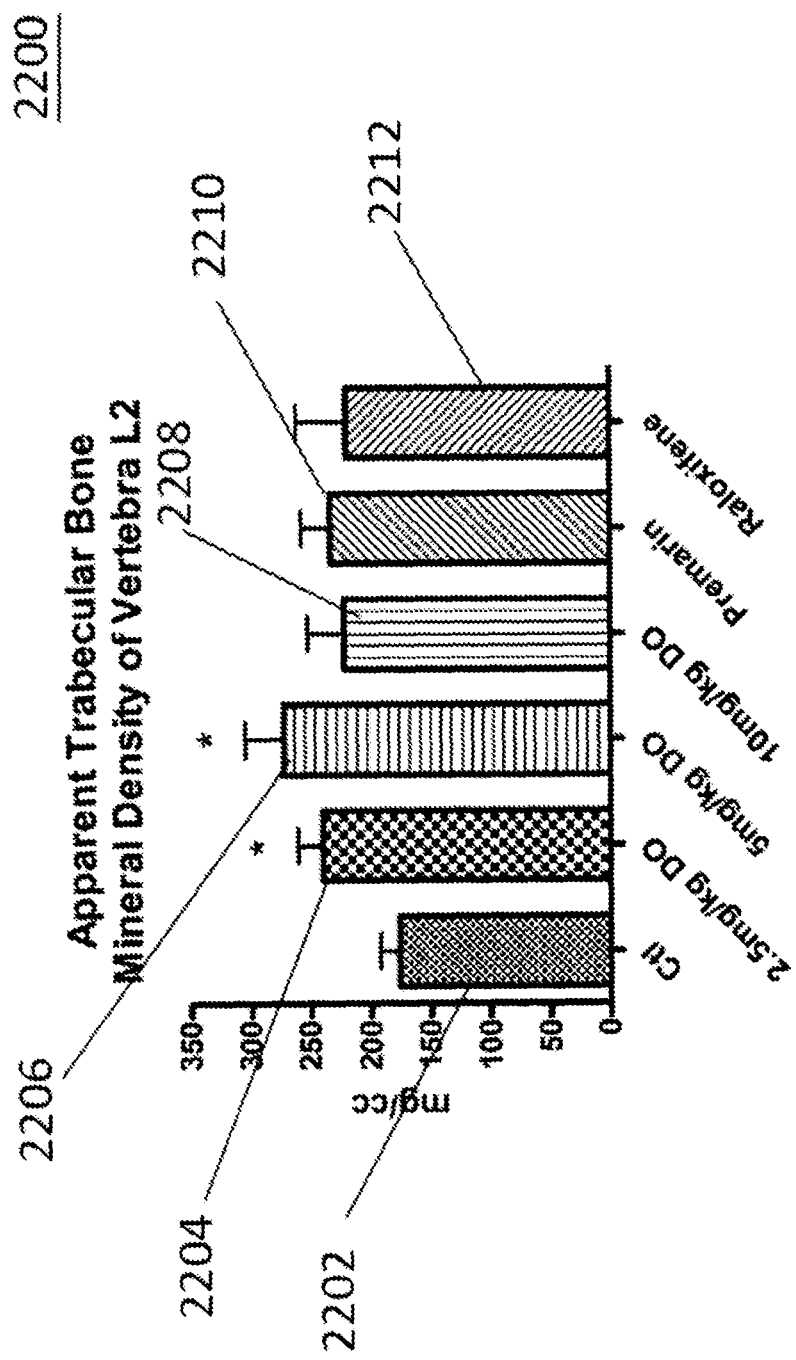
FIG. 22 is a graph showing the apparent trabecular bone mineral density of vertebra L2 of rats after 6-week treatment with DOI peptide. Results are expressed as means±SEM, n=6 (except permarin group, where n=3). * p<0.05, ** p<0.01 compared with control group by un-paired t-test. Ctl: old control group receiving intraperitoneal injections of PBS; Premarin and Raloxifene: two positive control groups treated with Premarin (12.4 mg/kg) and Raloxifene (25.56 mg/kg), respectively, by oral administration; DOI group: DOI treated group receiving daily intraperitoneal injections of DOI at 2.5 mg/kg, 5 mg/kg and 10 mg/kg, respectively.

The mean apparent trabecular bone mineral density (tBMD) of vertebra L2 in the groups treated with DOI peptide are shown in graph 2200 (FIG. 22). Animals given 2.5 mg/kg, 5 mg/kg, and 10 mg/kg DOI peptide had tBMD measurements of 240.2±21.03 mg/cc HA (2204), 272.5±32.2 mg/cc HA (2206), and 222.1±30.24 mg/cc HA (2208) respectively. Premarin treated animals had tBMD measurement of 233.6±24.23 mg/cc HA (2210) and Raloxifene treated animals had a tBMD measurement of 219.4±42.36 mg/cc HA (2212). There was a significant increase in tBMD in 2.5 mg/kg (2204) and 5 mg/kg (2206) DOI treated groups (p=0.0351 and 0.0229 respectively, un-paired t-test) compared to negative control group (2202) (176.3±15.69 mg/cc HA).

Figure 23:
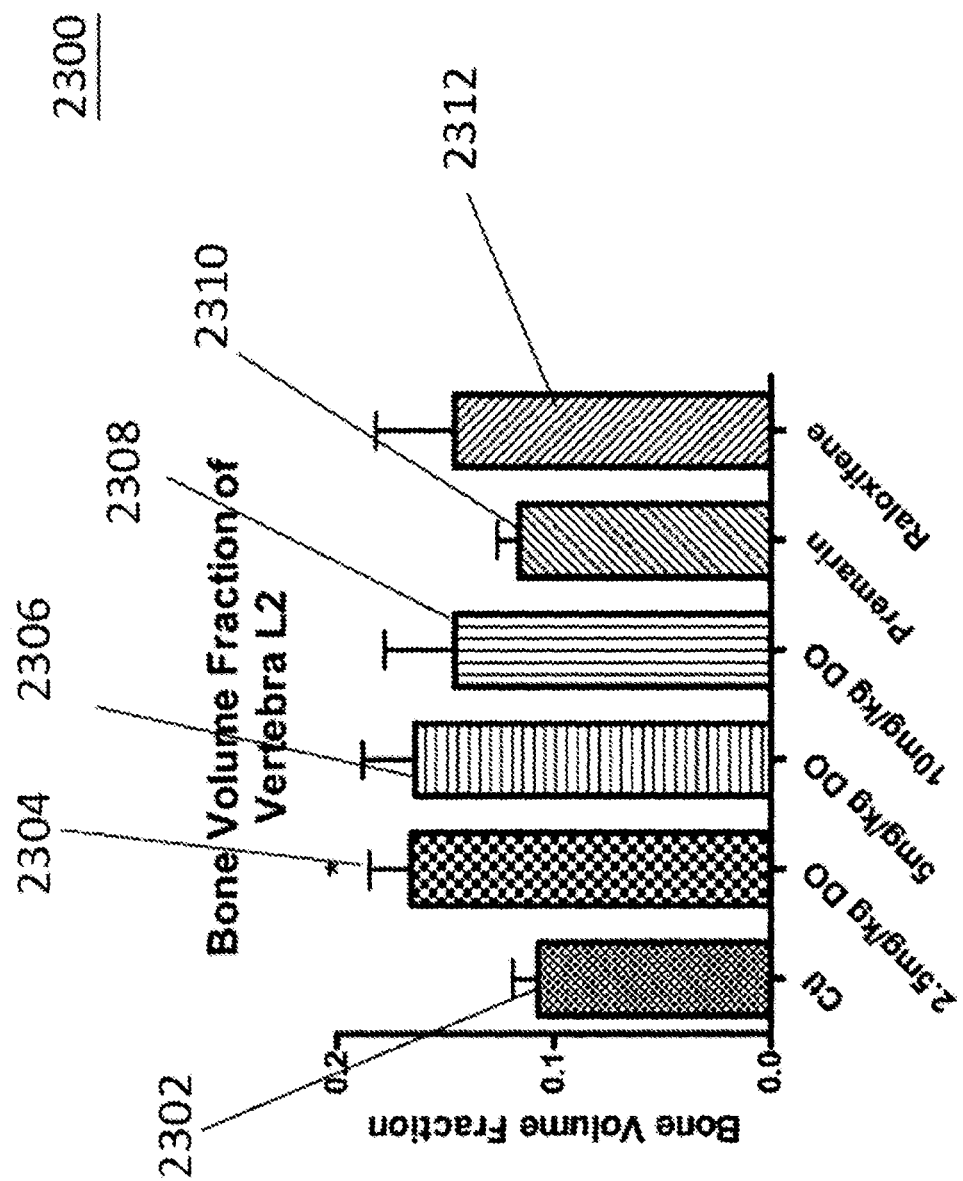
FIG. 23 is a graph showing the bone volume fraction of vertebra L2 of rats after 6-week treatment with DOI peptide. Results are expressed as means±SEM, n=6 (except permarin group, where n=3). * p<0.05, ** p<0.01 compared with control group by un-paired t-test. Ctl: old control group receiving intraperitoneal injections of PBS; Premarin and Raloxifene: two positive control groups treated with Premarin (12.4 mg/kg) and Raloxifene (25.56 mg/kg), respectively, by oral administration; DOI group: DOI treated group receiving daily intraperitoneal injections of DOI at 2.5 mg/kg, 5 mg/kg and 10 mg/kg, respectively.

Bone volume measurements are presented in graph 2300 (FIG. 23). The percentage bone volume fraction (BV/TV) of vertebra L2 were 16.57±1.939%, 16.43±2.378%, 14.59±3.228%, for animals given DOI peptide at doses of 2.5 mg/kg (2304), 5 mg/kg (2306), 10 mg/kg (2308), respectively. Premarin treated group 2310 had a bone volume fraction of 11.61±0.996%, and Raloxifene treated group 2312 was 146.1±3.61%. There was a significant increase in bone volume fraction in 2.5 mg/kg DOI treated group (p=0.0275, un-paired t-test) compared to control group 2302 (10.73±1.167%).

Figure 24:
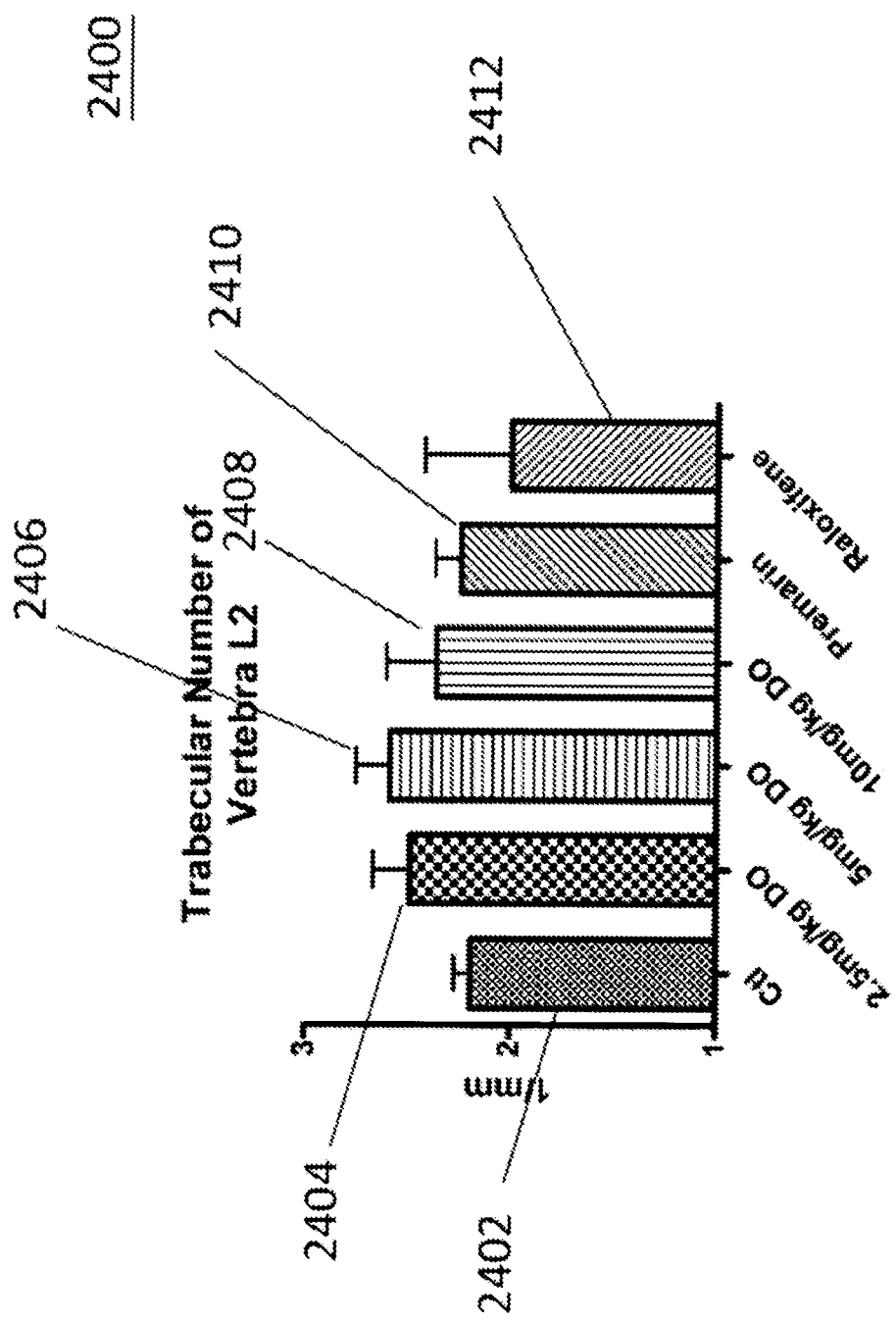
FIG. 24 is a graph of the trabecular number of vertebra L2 of rats after a 6-week treatment period with DOI peptide. Results are expressed as means±SEM, n=6 (except permarin group, where n=3). * p<0.05, ** p<0.01 compared with control group by un-paired t-test. Ctl: old control group receiving intraperitoneal injections of PBS; Premarin and Raloxifene: two positive control groups treated with Premarin (12.4 mg/kg) and Raloxifene (25.56 mg/kg), respectively, by oral administration; DOI group: DOI treated group receiving daily intraperitoneal injections of DOI at 2.5 mg/kg, 5 mg/kg and 10 mg/kg, respectively.

Trabecular bone numbers (Tb.N) of vertebra L2 are presented in graph 2400 (FIG. 24). The trabecular bone numbers were 2.491±0.178 mm$^{-1}$, 2.59±0.164 mm$^{-1}$, 2.365±0.243 mm$^{-1}$, for animals given DOI peptide at doses of 2.5 mg/kg (2404), 5 mg/kg (2406), 10 mg/kg (2408), respectively. Premarin treated group 2410 had a trabecular bone number of, 2.247±0.124 mm$^{-1}$, and Raloxifene treated group 2412 was 2±0.425 mm$^{-1}$. There was an average increase of 13.59%, 18.10% and 7.84% in Tb.N the groups 2404, 2406, and 2408 treated daily with DOI peptide at 2.5 mg/kg (2404) 5 mg/kg (2406) and 10 mg/kg (2408) respectively compared to control group 2402 (2.193±0.082 mm$^{-1}$), which is not statistically different from that of Premarin treated group 2410.

Figure 25:
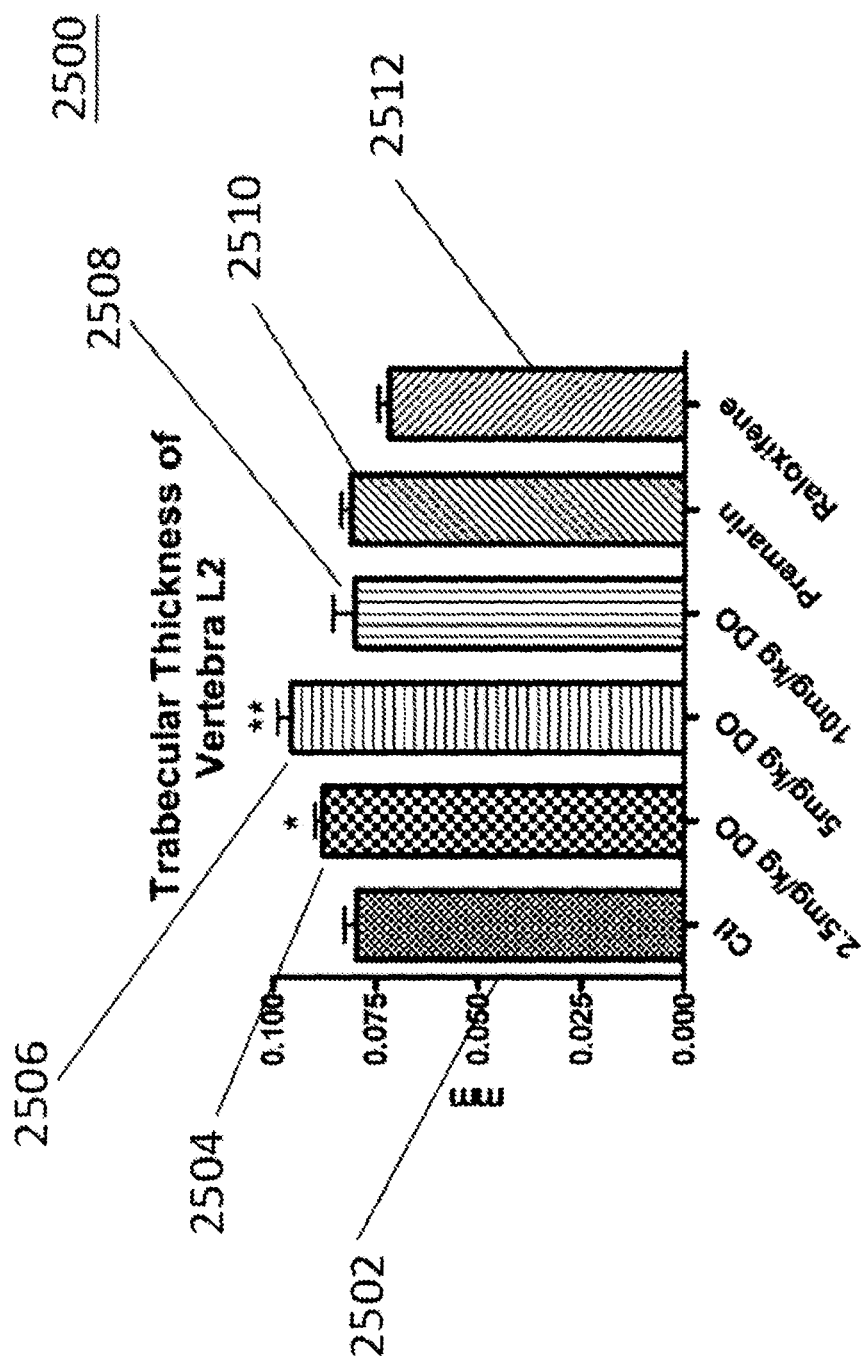
FIG. 25 is a graph of the trabecular thickness of vertebra L2 of rats after a 6-week period of treatment with DOI peptide. Results are expressed as means±SEM, n=6 (except permarin group, where n=3). * p<0.05, ** p<0.01 compared with control group by un-paired t-test. Ctl: old control group receiving intraperitoneal injections of PBS; Premarin and Raloxifene: two positive control groups treated with Premarin (12.4 mg/kg) and Raloxifene (25.56 mg/kg), respectively, by oral administration; DOI group: DOI treated group receiving daily intraperitoneal injections of DOI at 2.5 mg/kg, 5 mg/kg and 10 mg/kg, respectively.

Trabecular thickness (Tb.Th) measurements of vertebra L2 are presented in graph 2500, shown in FIG. 25. The Tb.Th measurements were 0.088±0.002 mm (2504), 0.096±0.003 mm (2506), and 0.0801±0.005 mm (2508) for animals given DOI peptide at doses of 2.5 mg/kg (2504), 5 mg/kg (2506), 10 mg/kg (2508), respectively. The Premarin treated control group had a Tb.Th measurement 2510 of 0.081±0.003 mm, and the Raloxifene treated group had Tb.Th measurement 2512 of 0.0719±0.003 mm. There was a significant increase in Tb.Th 2104 and 2506 in the 2.5 mg/kg and 5 mg/kg DOI treated groups (p=0.0419 and 0.0052 respectively, un-paired t-test) compared to control group 2502 (0.080±0.003 mm).

Figure 26:
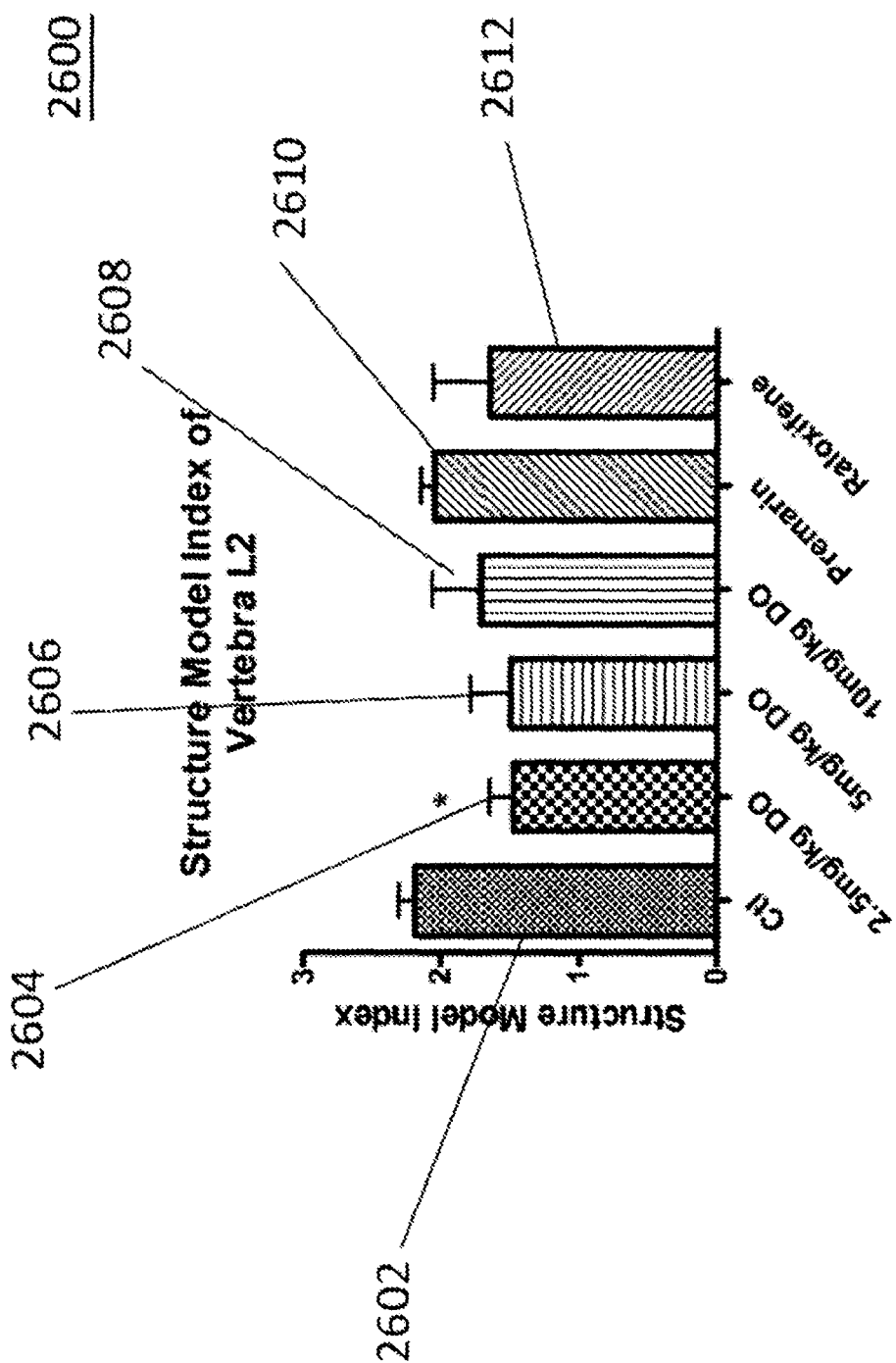
FIG. 26 is a graph of the structure model index of vertebra L2 of rats after a 6-week treatment period with DOI peptide. Results are expressed as means±SEM, n=6 (except permarin group, where n=3). * p<0.05, ** p<0.01 compared with control group by un-paired t-test. Ctl: old control group receiving intraperitoneal injections of PBS; Premarin and Raloxifene: two positive control groups treated with Premarin (12.4 mg/kg) and Raloxifene (25.56 mg/kg), respectively, by oral administration; DOI group: DOI treated group receiving daily intraperitoneal injections of DOI at 2.5 mg/kg, 5 mg/kg and 10 mg/kg, respectively.
Figure 27:
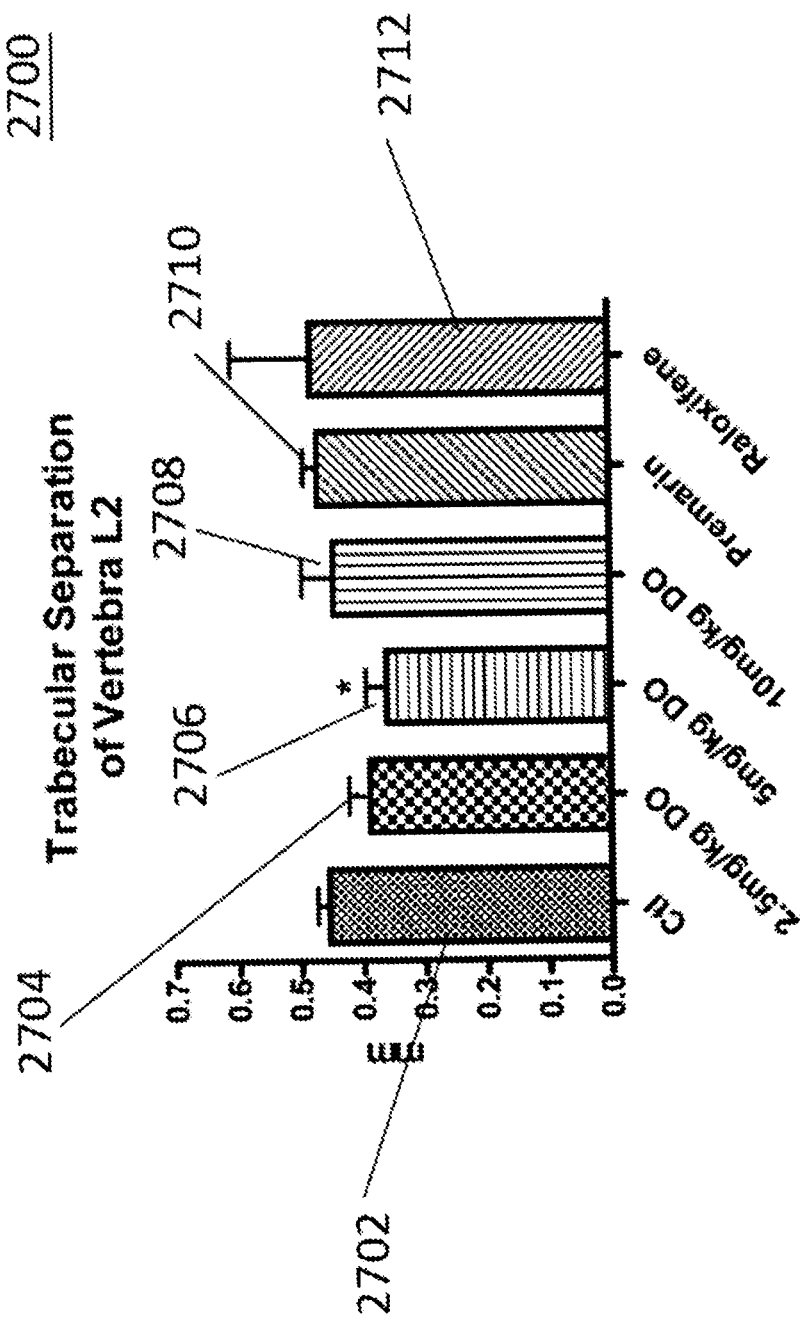
FIG. 27 is a graph of the trabecular separation of vertebra L2 of rats after a 6-week treatment period with DOI peptide. Results are expressed as means±SEM, n=6 (except permarin group, where n=3). *p<0.05, ** p<0.01 compared with control group by un-paired t-test. Ctl: old control group receiving intraperitoneal injections of PBS; Premarin and Raloxifene: two positive control groups treated with Premarin (12.4 mg/kg) and Raloxifene (25.56 mg/kg), respectively, by oral administration; DOI group: DOI treated group receiving daily intraperitoneal injections of DOI at 2.5 mg/kg, 5 mg/kg and 10 mg/kg, respectively.

The structure model indices (SMI) of the L2 vertebrae are presented in graph 2600, shown in FIG. 26. The SMI values of vertebra L2 were 1.48±0.177 (2604), 1.501±0.281 (2606), and 1.715±0.352 (2608) for animals given DOI peptide at doses of 2.5 mg/kg (2604), 5 mg/kg (2606), 10 mg/kg (2608), respectively. The Premarin treated control group had SMI value (2610) of 2.047±0.101, and Raloxifene treated control group 2612 had an SMI value of 1.653±0.402. There was a significant decrease in SMI value 2604 of the 2.5 mg/kg DOI treated group (p=0.0115, un-paired t-test) compared to control group SMI value 2602 of 2.186±0.121.

The trabecular separations (Tb.Sp) of the L2 vertebrae are presented in graph 2700, shown in FIG. 27. The Tb.Sp values were 0.388±0.034 mm (2704), 0.360±0.033 mm (2706), and 0.445±0.051 mm (2708) for animals given DOI peptide at doses of 2.5 mg/kg, 5 mg/kg, 10 mg/kg, respectively. The Premarin treated control group had Tb.Sp value 2710 of 0.471±0.021 mm; the Raloxifene treated group had Tb.Sp value 2712 of 0.480±0.127 mm. There was an significant decrease in Tb.Sp value 2706 in the 5 mg/kg DOI treated group (p=0.0358, un-paired t-test) compared to the negative control group Tb.Sp value 2702 of 0.454±0.020 mm.

High resolution microCT reveal a general increase in bone mineral density (FIG. 22), bone volume fraction (FIG. 23), trabecular number (FIG. 24) and trabecular thickness (FIG. 25), and a concomitant decrease in both structure model index (FIG. 26) and trabecular separation (FIG. 27). These density and bone micro-architecture changes favor an enhancement of bone strength. The decrease in structure model index indicates an increase in the ratio of plate-shaped to rod-shaped trabeculae. The latter trabecular structure is dominant in osteoporosis. The trabeculae shape changes show that the bone may become less porous as reflected in the parallel decrease in trabecular separation. In one embodiment, administration of DOI peptide exerts an anti-osteoporotic effect on the trabecular bone in this old-age rat model.

Detection of protein level of brain derived neurotrophic factor (BDNF) and TrkB gp445: The protein levels of brain derived neurotrophic factor (BDNF) in the rat prefrontal cortex and hippocampus were measured by using brain derived neurotrophic factor (BDNF) Sandwich ELISA Kit (#CYT306; Millipore), following the manufacturer's instruction. The protein expression levels of BDNF were normalized by using the total protein concentration of the individual samples. Immunoblotting was performed using anti-TrkB receptor antibody (sc-8316, Santa Cruz Biotechnology, Inc) for proteins from prefrontal cortex, and with anti-GAPDH antibody for internal standard, followed by incubation with horseradish peroxidase-conjugated secondary antibody. Chemiluminescence detection (GE Bio-health) was accomplished with the Bio-Rad Chemi Doc™ EQ densitometer (Bio-rad) and quantified by using Bio-Rad Quantity One 1-D Analysis software (Bio-Rad laboratories, Hercules, Calif., USA).

Groups of 3-6 animals per group were dosed daily with 2.5 mg/kg 5 mg/kg, 10 mg/kg of DOI peptide, or 12.4 mg/kg Premarin. A negative control group received daily doses of PBS. After 6 weeks of dosing, BDNF protein levels (normalized to total protein content) were determined in the hippocampus, and prefrontal cortex.

The BDNF levels in the hippocampus, presented in graph 2800 (FIG. 28), were 28.10+2.117 pg/mg, 36.17±3.177 pg/mg, 30.70±3.878 pg/mg for animals given DOI peptide at doses of 2.5 mg/kg (2804), 5 mg/kg (2806), 10 mg/kg (2808), respectively. The Premarin treated control group 2810 had BDNF protein concentration 2810 32.46±2.749 pg/mg in the hippocampus. There was a significant increase in the BDNF protein level in group 2806 that had received 5 mg/kg DOI peptide (p=0.024, un-paired t-test) compared with the control group 2802 (26.87 t 1.392 pg/mg).

The BDNF levels in the prefrontal cortex, presented in graph 2900 (FIG. 29) were 51.87±4.942 pg/mg, 71.82±4.682 pg/mg, 67.22±6.331 pg/mg for animals given DOI peptide at doses of 2.5 mg/kg (2904), 5 mg/kg (2906), and 10 mg/kg (2908), respectively. The Premarin treated control group had BDNF protein concentration 56.84±5.478 pg/mg (2910) in the prefrontal cortex. There was significant increase in the BDNF protein level 5 mg/kg DOI treated group 2906 (p=0.047, un-paired t-test) compared with control group 2902 (55.77±5.580).

TrkB is the high affinity catalytic receptor for several neurotrophins, which are small protein growth factors that induce the survival and differentiation of distinct cell populations. The neurotrophins that activate TrkB include BDNT. TrkB mediates the multiple effects BDNF and other neutrophins including neuronal differentiation and survival within the brain.

Figure 30:
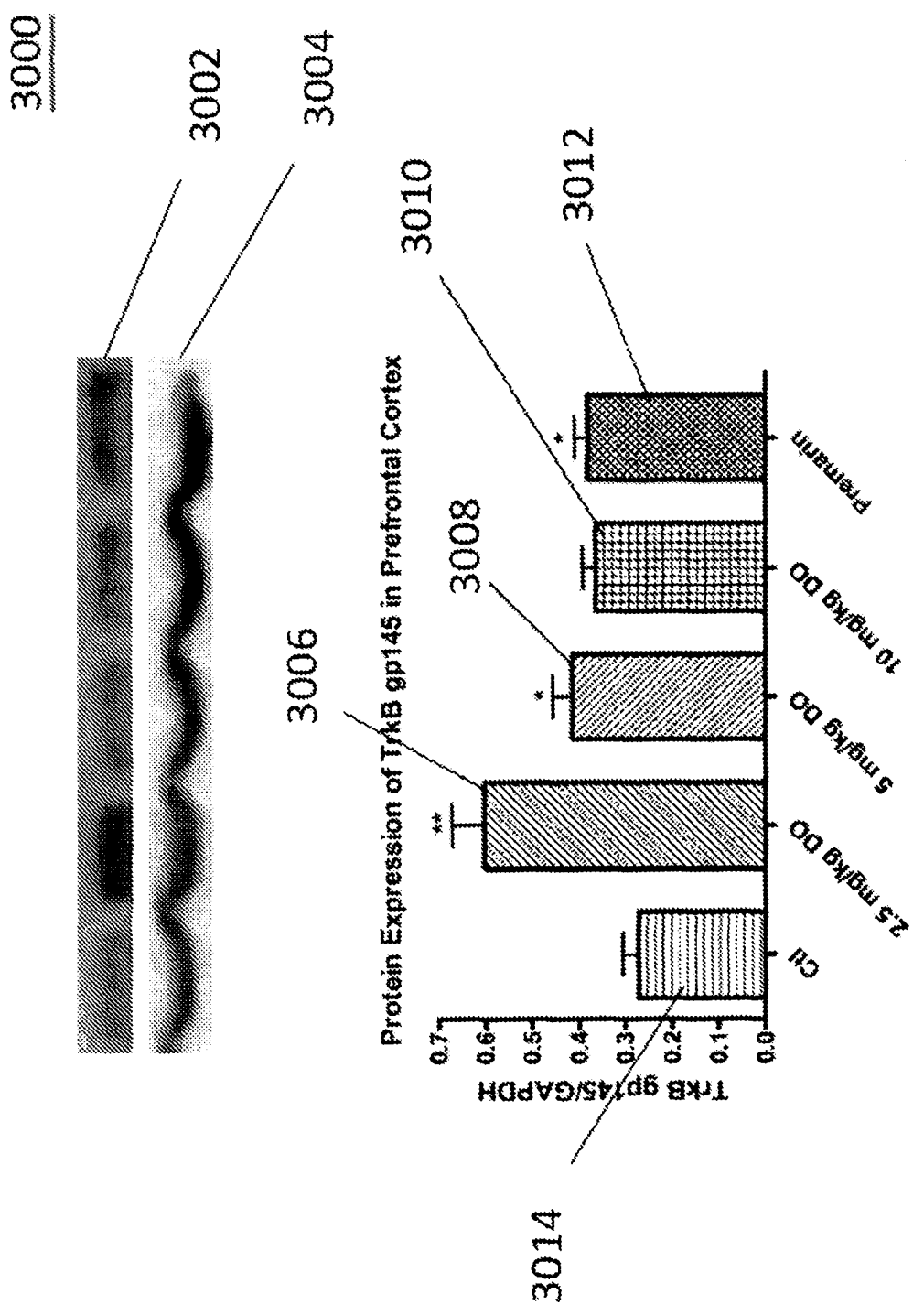
FIG. 30 is a graph showing the protein level of TrkB gp145 receptor protein in prefrontal cortex of Sprague-Dawley rats after 6-week treatment with DOI peptide. Results are expressed as means±SEM, n=6. * p<0.05, ** p<0.01 compared with control group by un-paired t-test. Ctl: old control group receiving intraperitoneal injections of PBS; Premarin: positive control group treated with Premarin (12.4 mg/kg/daily) by oral administration; DOI group: DOI treated group receiving daily intraperitoneal injections of DOI at 2.5 mg/kg, 5 mg/kg and 10 mg/kg, respectively.

Specific induction of TrkB gp145 receptor protein compared to GAPDH 3004 is apparent from a comparison of the thickness of bands 3002 (TrkB gp145) and 3004 (GAPDH) obtained from SDS PAGE, shown in FIG. 30. The protein levels of TrkB gp145 receptor/GAPDH in the prefrontal cortex, presented in graph 3000, FIG. 30 were 0.6038±0.06977, 0.4150±0.04169, 0.3638±0.02919 for animals given DOI peptide at doses of 2.5 mg/kg (3006), 5 mg/kg (3008), and 10 mg/kg (3010), respectively. The Premarin treated control group had TrkB gp145 receptor/GAPDH ratio of 0.3805±0.03002 (3012) in the prefrontal cortex. There was a significant increase in the protein expression level in 3006 (2.5 mg/kg), 3008, 5 mg/kg and Premarin 3012 treated groups (p=0.0016, 0.0239 and 0.0377 respectively, un-paired t-test) compared with control group 3014 (0.2723±0.03377).

Figure 28:
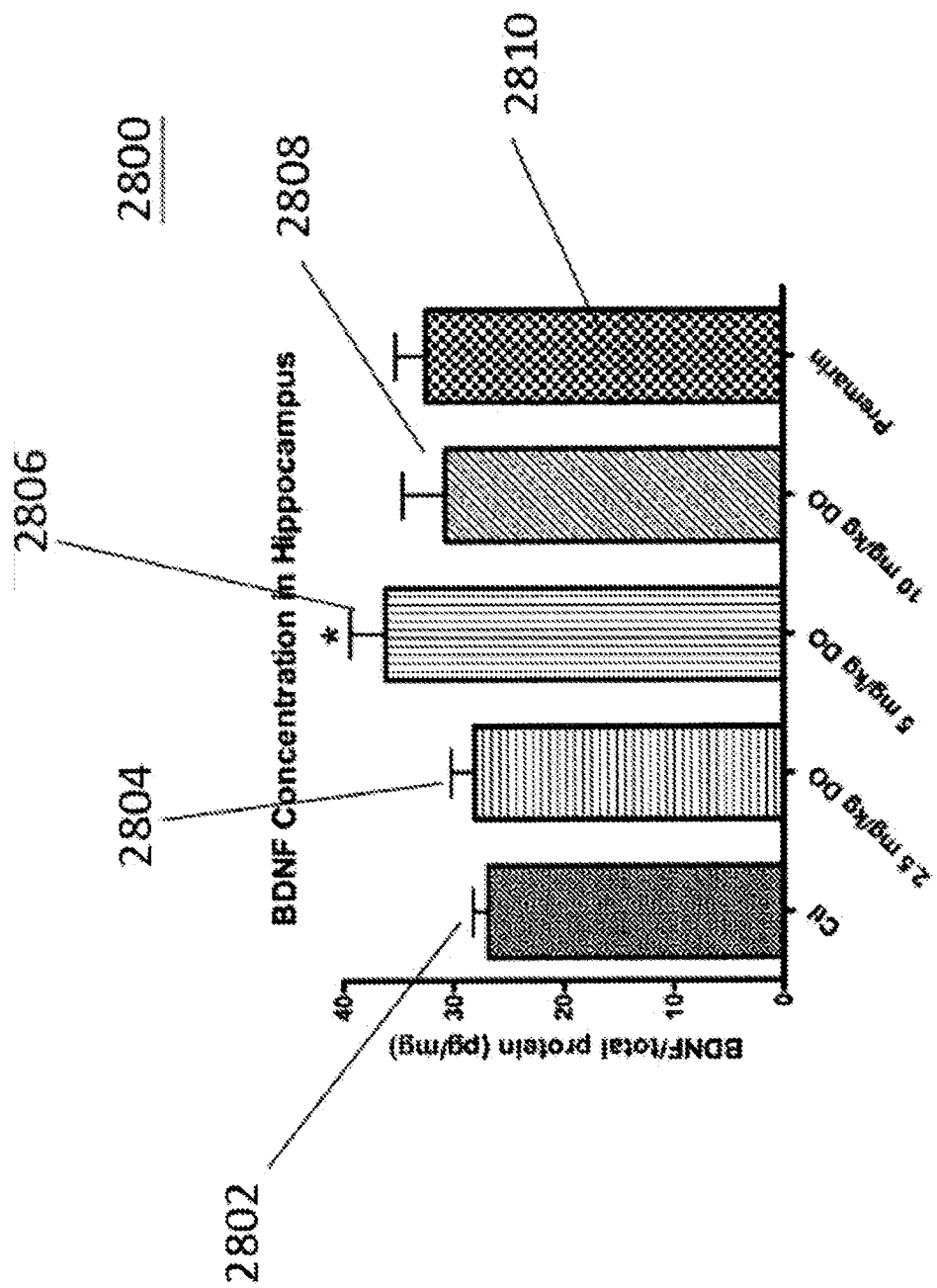
FIG. 28 is a graph of the protein level of brain derived neurotrophic factor (BDNF) protein in the hippocampus of Sprague-Dawley rats after 6-week treatment with DOI peptide. Results are expressed as means±SEM, n=6. * p<0.05, ** p<0.01 compared with control group by un-paired 1-test. Ctl: old control group receiving intraperitoneal injections of PBS; Premarin: positive control group treated with Premarin (12.4 mg/kg/daily) by oral administration; DOI group: DOI treated group receiving daily intraperitoneal injections of DOI at 2.5 mg/kg, 5 mg/kg and 10 mg/kg, respectively.

In one embodiment, DOI peptide exerts beneficial effects on cognitive functions, as revealed by the elevated BDNF translational level in the DOI-treated rats (FIG. 28). BDNF is involved in synaptic plasticity and both maintenance and survival of neurons in the hippocampus and cortex, which is associated with cognitive functions. While BDNF expression decreases in deprivation of estrogen, estrogen replacement in rodents can reverse the change. The elevated protein expression level of BDNF and TrkB receptor in the prefrontal cortex of DOI peptide treated rats (FIGS. 29, 30) indicates that the DOI peptide has a stimulatory effect in prefrontal BDNF signaling and a potential beneficial role in enhancing cognitive functions during aging.

Figure 31:
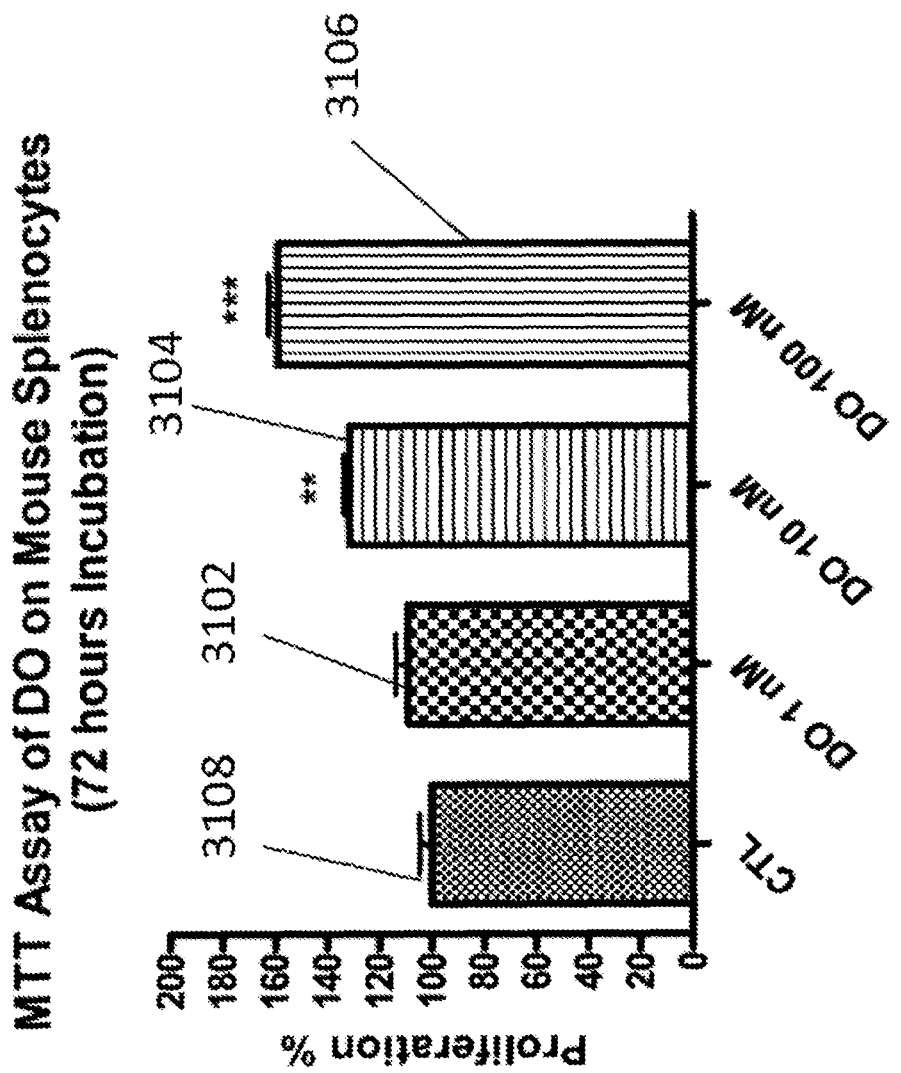
FIG. 31 is a graph showing the results of an assay of mitogenic activity of DOI peptide on mouse splenocytes after treatment with DOI for 48 hours. Results are expressed as means±SEM, n=3.  p<0.01, * p<0.001 compared with control group by un-paired t-test.
Figure 32:
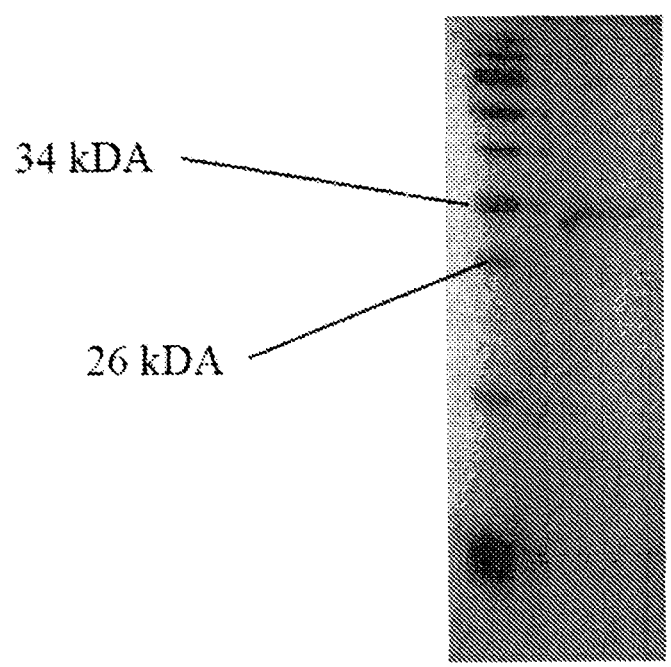
FIG. 32 is a photograph of a 15% SDS PAGE, showing the DOI protein isolated by the antibody affinity column visualized by silver staining. The left lane is protein molecular weight standards and right lane showing the eluted DOI protein retained by affinity column. The size of DOI protein eluted is approximately 30 kDA, when compared to that of molecular weight standards 34 kDA and 26 kDA. The apparent molecular weight of the DOI peptide is consistent with that obtained using conventional column purification techniques.

In one embodiment, the mitogenic activity of DOI was assayed using mouse splenocytes. Splenocytes were isolated from BALB/c mice. The isolated splenocytes were diluted with RPMI 1640 with 15% fetal bovine serum and 1% penicillin-streptomycin and seeded in 96-well microplates at a density of $5 \times 10^5$ cells/100 µl/well. Cells were cultured at 37° C. in a humidified atmosphere with 5% carbon dioxide for 24 hours. DOI peptide was then added at 1 nM (3102), 10 nM (3104) and 100 nM (3106) concentrations, as shown in FIG. 31. Cells without DOI treatment served as control 3108. The cells after adding drug were incubated for further 72 hours, followed by incubation with MTT solution for 3 hours. Formazan crystals were dissolved by DMSO. Absorbance at O.D. 540 nm was measured with a microplate reader (Model 680, Bio-Rad). Percentage proliferation relative to the control was calculated.

As shown in the FIG. 31, DOI peptide displayed a mitogenic effect, as reflected by the proliferation of mouse splenocytes, in a dose dependent manner. There were a significant increase in proliferation percentage in mouse splenocytes treated with 10 nM (3104) and 100 nM (3106) DOI peptide, where the mean proliferation percentage relative to control 3108 were 131.6±2.098% (p=0.0026, unpaired t-test) and 158.8±3.610% (p<0.0001, unpaired t-test) (mean±SEM) respectively.

Menopause and general ageing are accompanied by the decline in immune functions. Changes in the immune system during aging including immune tolerance, increase of autoantibody reactions, decline in function of natural killer cells, B lymphocytes and T lymphocytes have been observed. Reduced estrogen levels after menopause correlate with increased levels of pro-inflammatory serum markers, decreased in CD4 T and B lymphocytes levels. In one embodiment, administration of DOI peptide improves immune function in aged individuals through a mitogenic effect on splenocytes.

Purification of the DOI Protein Using Antibody—Affinity Column Purification Method Basic antigen affinity-purified polyclonal antibody (rabbit) was raised with purified DOI protein as the antigen (GenScript). The anti-DOI antibody was covalently attached to a column with the use of AminoLink® Plus Immobilization kit (Thermo Scientific) to produce an affinity column that purifies the DOI protein by the affinity to the antibody.

*Dioscorea opposita* was peeled and homogenized in an aqueous extraction buffer (5% acetic acid+0.1% β-mercaptoethanol) in a ratio of 1:2 (w/v) for 3 hours at 4° C. The homogenate was subjected to centrifugation at 17,700 g for 30 min at 4° C. The supernatant was collected and ammonium sulfate was added to 80% of saturation. The mixture was stirred at 4° C. overnight and subjected to centrifugation at 17,700 g for 1 hr at 4° C. The supernatant was collected and ammonium sulfate was added to 80% of saturation. The mixture was stirred at 4° C. overnight and subjected to centrifugation at 17,700 g for 1 hr at 4° C. The precipitate (protein extract) was retained and resuspended in purified water. The protein extract mixture was dialyzed against doubly distilled $H_2O$ overnight and then subjected to ultra-centrifugation at 40,000 g for 2 hr at 4° C. The supernatant was collected and subjected to the affinity column purification according to the manufacturer instructions of AminoLink® Plus Immobilization kit.

Estrogen concentration in cell culture medium of DOI-treated primary cell culture of rat ovarian granulosa cells was measured. Briefly, 21 to 23 day-old female Sprague-Dawley (SD)-rats were primed with 15 IU PMSG (Sigma) for 48 hours to stimulate follicular development. The rats were then sacrificed and ovaries were dissected. The ovarian follicles were punctured with a 25-gauge needle. The isolated granulosa cells were cultured at 37° C. in an atmosphere of 5% $CO_2$ in culture medium consisting of serum free DMEM/F12 1:1 medium containing 1% penicillin-streptomycin, 0.1% BSA and insulin (1 µg/ml) for 24 hour.

The DOI protein was isolated from various *Dioscorea* species isolated using AminoLink® Plus Column linked to anti-DOI antibody was then added to the granulosa cells for 24-hour treatment. The cell culture medium was collected for measurement of estrogen concentration and the cells were harvest for protein extraction. Protein concentration from cellular lysate was determined with Bradford assay.

Figure 33:
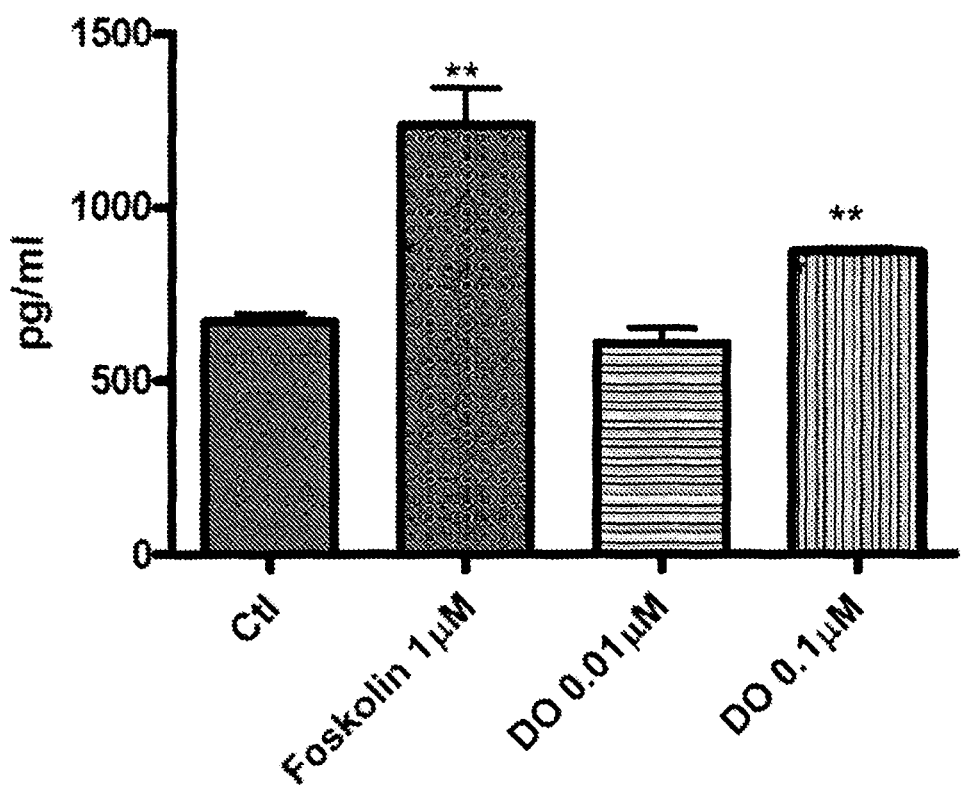
FIG. 33 shows the estrogenic activity of DOI protein on ovarian granulosa cells. The DOI protein is isolated from *Dioscorea opposita* using antibody affinity column. The results are expressed as means±SEM, n=3. ** $p<0.01$ compared with control group by un-paired t-test.

FIG. 33 shows estradiol concentration in cell culture medium of granulosa cells. The estradiol concentration of granulosa cell medium is expressed as mean pg estradiol/ml±SEM (n=3). The estradiol levels in control (Ctl) group, treatment with forskolin 1 µM, DOI 0.01 µM and DOI 0.1 µM are respectively 671.0±23.70, 1236±108.0, 872.9±10.33 and 609.2±44.82 pg/ml. There is significant difference in forskolin 1 µM (p<0.01) and DOI 0.1 µM (p<0.01) group compared with control group in unpaired t-test.

The DOI protein stimulates expression of ovarian aromatase and elevates tserum estradiol level. This Example investigates the safety and efficacy of the DOI protein for relieving menopausal symptoms. The activation of aromatase in extragonadal tissues such as mammary gland may lead to pathological consequences. Also, hyperactivation of aromatase in breast tissue may promote the progression of breast cancer, leading to enhanced estrogen production for growth of breast tumor.

To evaluate the effect of DOI protein on stimulating aromatase expression in extragonadal tissue, protein expression of aromatase in mammary gland was determined by Western blotting analysis. Protein expression of CYP-19 aromatase in mammary glands was compared to expression of glyceraldehyde 3-phosphate dehydrogenase treated with the DOI peptide.

Briefly, proteins were extracted from mammary glands of Sprague-Dawley rats using RIPA buffer (Sigma Aldrich) with Complete Protease Inhibitor Cocktail Tablets (Roche Applied Science). 20 µg of denatured proteins per sample were separated on SDS-PAGE and transferred to PVDF membranes. Immunoblotting was performed using specific anti-aromatase antibodies, with anti-GAPDH antibody as an internal standard, followed by incubation with horseradish peroxidase-conjugated secondary antibody. Chemiluminescence detection (GE Bio-health, Princeton, N.J.) was accomplished with the Bio-Rad Chemi Doc™ EQ densitometer (Bio-rad) and quantified by Bio-Rad Quantity One software (Bio-Rad laboratories, Hercules, USA).

Expression of protein for aromatase in mammary glands was measured in Sprague-Dawley rats after 6 weeks of treatment with DOI peptide. The protein expression level of aromatase in mammary glands from Sprague-Dawley rats from control group or treated with DOI peptide at 2.5 mg/kg, 5 mg/kg, 10 mg/kg and Premarin at 12.4 mg/kg was measured and expressed mean relative intensity±standard deviation.

Figure 34:
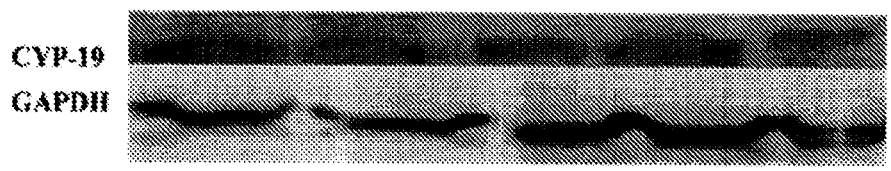
FIG. 34 shows the effect of the DOI protein on expression of aromatase in the mammary glands of Sprague-Dawley rats after a 6-week treatment with DOI peptide. Results are expressed as means±SEM, n=6. * $p<0.05$, $p<0.01$, *$p<0.001$ compared with control group by One Way ANOVA followed by Dunnett's Multiple Comparison Test. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.
Figure 34:
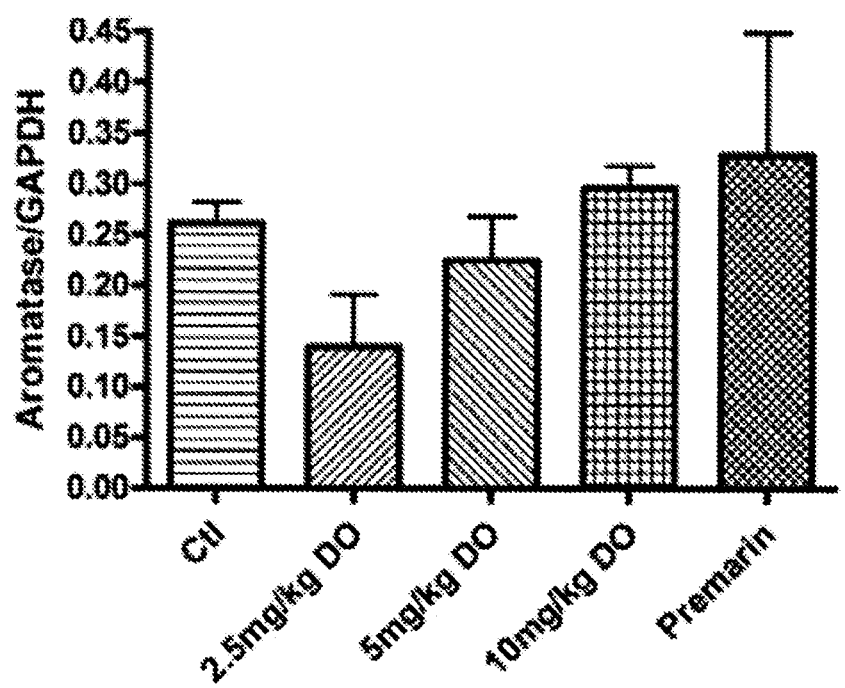

FIG. 34 shows that the protein expression levels of aromatase were 0.2614±0.04082 (control), 0.1390±0.08948 (2.5 mg/kg DOI-treated), 0.2243±0.08658 (5 mg/kg DOI-treated), 0.2963±0.04294 (10 mg/kg DOI-treated), 0.3285±0.2428 (premarin-treated), respectively. No statistical differences were detected in statistical analysis using one-way ANOVA.

The results show that the DOI protein stimulates aromatase in ovaries of Sprague-Dawley rats, but not in mammary glands, indicating that DOI has tissue-specific aromatase modulating properties. This shows that the DOI protein is less likely to increase the risk of breast cancers due to extragonadal stimulation of aromatase in breast tissues.

Antibodies

In one embodiment, the present invention provides an antibody that binds specifically to a polypeptide of the present invention. In one embodiment, the antibody binds specifically to polypeptide obtainable from *Dioscorea* sp., wherein the polypeptide has an apparent molecular weight of about 32.5 kDA by chromatography, wherein the first twenty-one consecutive amino acids at the N-terminal of the polypeptide consists of SEQ ID NO:1 and the polypeptide increases the level of estrogen in vitro or in vivo.

An antibody that is contemplated for use in the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment of an antibody yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "antigen binding fragment" with respect to antibodies, refers to, for example, Fv, F(ab) and F(ab')$_2$ fragments. Of particular importance for binding are the first 110 to 130 amino acids at the N-terminus of the amino acid sequences exemplified herein. Thus, high identity in the N-terminus 110, 115, 120, 125, or 130 amino acids constituting the variable region is preferred. Variant sequences preferably have more than 75%, 90%, or even 95% identity in this region.

The subject invention further comprises fusion constructs wherein the antibody, or fragment thereof, may be fused to one or more additional entities. The additional entity(ies) may be for example linkers, toxins, carriers, solid supports, and/or detectable molecules. In this context the binding portion may consist or consist essentially of the antibody.

"Specific binding" or "specificity" refers to the ability of an antibody or other agent to detectably bind an epitope presented on an antigen, while having relatively little detectable reactivity with other proteins or structures. Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules.

"Selectivity" refers to the preferential binding of a protein to a particular region, target, or peptide as opposed to one or more other biological molecules, structures, cells, tissues, etc. For example, selectivity can be determined by competitive ELISA or Biacore assays. The difference in affinity/avidity that marks selectivity can be any detectable preference (e.g., a ratio of more than 1:1.1, or more than about 1:5, if detectable).

If desired, the antibodies produced by the B cells can be modified in any suitable process. For example, the binding affinity of the antibodies can be increased via various methods known in the art. For example, binding characteristics can be improved by direct mutation, methods of affinity maturation, phage display, or chain shuffling within the nucleic acids encoding the antibody molecules. For example, individual residues or combinations of residues can be randomized so that in a population of otherwise identical antigen binding sites, all twenty amino acids are found at particular positions. Binding characteristics can also be improved by methods of affinity maturation. (See, e.g., Yang et al. (1995) *J. Mol. Bio.* 254, 392-403; Hawkins et al. (1992) *J. Mol. Bio.* 226, 889-896; or Low et al. (1996) *J. Mol. Bio.* 250, 359-368 (each of which is hereby incorporated by reference in its entirety, particularly with respect to methods of increasing the binding affinity of antibodies)). Methods known in the art include for example, Marks et al. *Bio/Technology*, 10:779-783 (1992) describes affinity maturation by VH and VL domain shuffling; random mutagenesis of CDR and/or framework residues is described by Barbas et al. *Proc. Natl. Acad. Sci., USA* 91:3809-3813 (1994); Schier et al. *Gene,* 169:147-155 (1995); Yelton et al. *J. Immunol.,* 155:1994-2004 (1995); Jackson et al., *J. Immunol.,* 154(7):3310-3319 (1995); and Hawkins et al, *J. Mol. Biol.,* 226:889-896 (1992).

Strategies for antibody optimization are sometimes carried out using random mutagenesis. In these cases positions are chosen randomly, or amino acid changes are made using simplistic rules. For example all residues may be mutated to alanine, referred to as alanine scanning. WO 9523813 (which is hereby incorporated by reference in its entirety) teaches in vitro methods of increasing antibody affinities utilizing alanine scanning mutagenesis. Alanine scanning mutagenesis can also be used, for example, to map the antigen binding residues of an antibody (Kelley et al., 1993, *Biochemistry* 32:6828-6835; Vajdos et al., 2002, *J. Mol. Biol.* 320:415-428). Sequence-based methods of affinity maturation (see, U.S. Pat. Application No. 2003/022240 A1 and U.S. Pat. No. 2002/177170 A1, both hereby incorporated by reference in their entireties) may also be used to increase the binding affinities of antibodies.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Modification of Amino Acid Sequences

If desired, the subject protein can be modified by any suitable process. For example, individual residues or combinations of residues can be randomized so that in a population of otherwise identical antigen binding sites, all twenty amino acids are found at particular positions. Binding characteristics can also be improved by methods of affinity maturation. Strategies for protein optimization are sometimes carried out using random mutagenesis. In these cases positions are chosen randomly, or amino acid changes are made using simplistic rules. For example all residues may be mutated to alanine, referred to as alanine scanning. In addition, substitution of amino acids other than those specifically exemplified or naturally present in a protein of the invention are also within the scope of the present invention. For example, non-natural amino acids can be substituted for the amino acids of the protein, so long as the protein having the substituted amino acids retains substantially the same functional activity as the protein in which amino acids have not been substituted.

Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a modified protein of the present invention having an amino acid of one class is replaced with another amino acid of the same class fall within the scope of the subject invention so long as the modified protein having the substitution still retains substantially the same functional activity (e.g., increasing the levels of estradiol, estrogen, and/or progesterone) that does not have the substitution. Polynucleotides encoding a modified protein having one or more amino acid substitutions in the sequence are also within the scope of the present invention. Table 4 provides a listing of examples of amino acids belonging to each class.

TABLE 4

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Polypeptides within the scope of the subject invention can also be defined in terms of more particular identity and/or similarity ranges with those sequences of the invention specifically exemplified herein. The sequence identity will typically be greater than 75%, preferably greater than 80%, more preferably greater than 90%, and can be greater than 95%. The identity and/or similarity of a sequence can be 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

Fragments of the polypeptides of the present invention, having activity including increasing the level estradiol, estrogen, and/or progesterone, can be generated using routine techniques. For example, a library of polypeptide fragments of various sizes can be generated from the full length DOI peptide of the present invention; active fragments can be selected using assays taught in the present application, including testing the activity of the fragment in increasing the level of estradiol, estrogen, and/or progesterone; increasing the expression levels of aromatase CYP-19 and/or follicle-stimulating hormone receptor (FSHR); increasing the level of brain derived neurotrophic factor (BDNF) and/or TrkB receptor in hippocampus and prefrontal cortex; treating osteoporosis; e) improving cognitive function; and/or stimulating a splenic mitosis response.

The DOI peptide of the present invention can conveniently be administered in a pharmaceutical composition containing the DOI peptide at a clinically effectively concentration in combination with a suitable excipient formulation. The formulation may be selected to optimize delivery of DOI peptide to the ovaries and thereby stimulate secretion of estrogen and progesterone. Such pharmaceutical compositions are prepared by methods and contain excipients that are well known in the art. A generally recognized compendium of such methods and ingredients is Remington's Pharmaceutical Sciences by E. W. Martin (Mark Publ. Co., 15.sup.th Ed., 1975). Compositions containing the DOI peptide of the present invention can be administered parenterally, for example, by intravenous, intraperitoneal or intramuscular injection, topically, orally, or rectally.

Frequently, protein pharmaceuticals are rapidly eliminated from the systemic circulation by renal clearance and/or enzymatic degradation. They may also elicit an adverse immune response. As macromolecules, protein pharmaceuticals may not be readily taken up by their target cells, and may instead be taken up by non-target tissues or organs.

In one embodiment, renal filtration and clearance of the DOI protein are addressed by conjugating the protein with one or more water-soluble polymers resulting in a complex larger than 40-kDa. Conjugation can also increase the resistance of the DOI peptide to enzymatic degradation and decrease its immunogenicity. In one embodiment, the polymer is poly(ethylene glycol) (PEG).

In one embodiment, DOI peptide is delivered using microreservoir carriers that provide a high degree of protection against enzymatic degradation by isolating the protein from the external environment. Examples of such microreservoirs include liposomes and nanoparticles.

Vector molecules with affinity towards characteristic ligands of target tissue can further improve the targeting of protein or peptide drug carriers. Vector molecules with this capability include antibodies, peptides, lectins, saccharides, hormones as well as small molecules such as vitamin. Among these molecules, antibodies have the highest potential specificity for targeting. In various embodiments, suitable vector molecules are used alone or in combination with protein conjugation, microreservoirs or other technologies to provide an optimal drug delivery system for DOI peptide.

In one embodiment, the DOI peptide is enterically coated, and delivered orally. For oral therapeutic administration, the active compound may be combined with one or more excipients and used in the form of ingestible tablets, buccal tablets, troches, capsules, elixirs, suspensions, syrups, wafers, and the like. Such compositions and preparations typically contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form would be pharmaceutically acceptable and substantially non-toxic in the amounts employed. In addition, the DOI peptide may be incorporated into sustained-release preparations and devices.

In one embodiment, pharmaceutical dosage forms suitable for injection or infusion of the DOI peptide include sterile aqueous solutions or dispersions or sterile powders comprising the DOI peptide which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. Any of these injectable formulations may be suitable for use with the DosePro drug delivery system (Zogenix Corp., San Diego, Calif., USA), or other similar devices.

Sterile injectable solutions can be prepared by incorporating the DOI peptide in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the DOI peptide plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the DOI peptide can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the DOI peptide of the invention can be determined from it apparent in vivo activity in animal models. Methods for the extrapolation of effective dosages in rats and other animals, to humans are known to the art. In the present invention, the effective dose in aged Sprague-Dawley rats is in the range of 2.5 to 10.0 mg/kg. In one embodiment the effective dose for human patients is in the range of 0.5 to 500 mg/kg.

In one embodiment, the DOI peptide is conveniently administered in unit dosage form; for example, containing 1 to 10 g, of DOI peptide per unit dosage form. The desired dose may conveniently be presented in a single dose or as divided doses administered at appropriate intervals, for example, as two, three, four or more sub-doses per day.

The exact regimen for administration of the DOI peptide can be obtained depending upon the needs of the individual patient being treated, the type of treatment and, of course, the judgment of the attending practitioner.

In one embodiment the DOI peptide is extracted for the rhizomes of the Chinese yam *Dioscorea Opposita*, as described above. In another embodiment the DOI peptide is produced by recombinant means.

While the invention has been described with reference to particular embodiments, it will be understood by one skilled in the art that variations and modifications may be made in form and detail without departing from the spirit and scope of the invention.

In one embodiment, the present invention also provides therapeutic compositions, comprising an isolated or substantially pure polypeptide compound of the present invention, or a salt thereof, and optionally, a pharmaceutically acceptable carrier.

The term "carrier" refers to a diluent, adjuvant, excipient, or vehicle with which the compound is administered. Such pharmaceutical carriers can be sterile liquids, such as water and oils, including those of petroleum oil such as mineral oil; vegetable oil such as peanut oil, soybean oil, and sesame oil; animal oil; or oil of synthetic origin. Saline solutions and aqueous dextrose and glycerol solutions can also be employed as liquid carriers, particularly for injectable solutions.

The therapeutic or pharmaceutical compositions of the invention can be formulated as neutral or salt forms. Pharmaceutically acceptable salts include, but are not limited to, salts formed with hydrochloric, phosphoric, acetic, oxalic, tartaric acids, sodium, potassium, ammonium, calcium, ferric hydroxides, etc.

The invention also provides a pharmaceutical pack or kit comprising one or more containers filled with one or more of the ingredients, e.g., compound, carrier, of the pharmaceutical compositions of the invention.

The compounds and compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject. In preferred embodiments, the compounds and compositions of the subject invention are administered to a subject by oral administration.

The amount of the therapeutic or pharmaceutical composition of the invention which is effective in the treatment of a particular disease, condition or disorder will depend on the route of administration, and the seriousness of the disease, condition or disorder, and should be decided according to the judgment of the practitioner and each patient's circumstances. In general, the dosage ranges from about 0.001 mg/kg to about 3 g/kg.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

RESULTS

Protein Extraction and Column Purification of DOI

Figure 2:
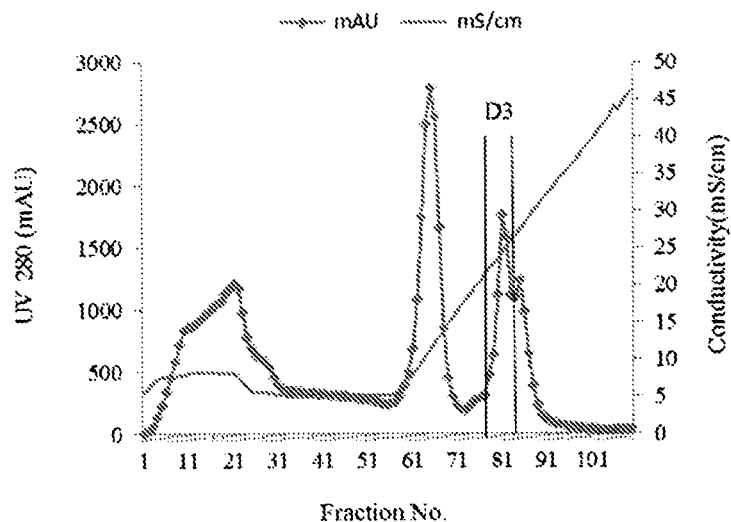
FIG. 2 is a chromatogram showing the purification of an extract of *Dioscorea opposita* on a HiPrep 16/10 DEAE FF column.

Crude protein preparations were obtained from the Chinese yam homogenate by chromatography on a HiPrep 16/10 DEAE FF column using an AKTA purifier system (FIG. 2). The third peak (D3) was eluted with a linear gradient of 0-0.45M NaCl in 100 mM Tris buffer, pH8.0. Since fraction D3 contained estrogen-stimulating activity, this active fraction was collected and dialyzed for further purification on a HiPrep 16/10 Phenyl FF (high sub) column using an FPLC system. The active fraction P1 was eluted with a linear gradient of 0.3-0M $(NH_4)_2SO_4$ in 10 mM sodium phosphate pH 7.0 (FIG. 3), and then was dialyzed for further purification on a Superdex 75 10/300 GL column (GE Healthcare) with an FPLC system. The pure active protein (S1), designated as DOI, was obtained by eluting with 50 mM sodium phosphate buffer (pH 7.2) containing 150 mM NaCl. The protein yield of DOI was 0.3% of the total soluble protein in *Dioscorea opposita* thumb. The purification steps are summarized in Table 2.

Chemical Characterization of DOI

The molecular weight of DOI was 32.5 kD as measured by size-exclusion chromatography and SDS-PAGE after silver staining, respectively (Table 1). The N-terminal sequence of DOI determined by Edman degradation was GIGKITTY-WGQYSDEPSLTE. The partial amino acid sequence of DOI determined by mass-Spectrometry was:
KSFYTRSNFLEAVSAYPGFGTKREIAAY-FAHVTHGPMQLSWNYNYIDAGKELHF DGLNDPDI-VGRDPIISFKTSLWFWIRKGVQYVILDP-NQGFGATIRIINGGQECDGHNTAQ MMARVGYYQEYCAQ. The exact molecular weight of DOI was 33.5 kDa as measured by mass spectrometry (FIG. 35).

Biological Characterization of DOI

Figure 9:
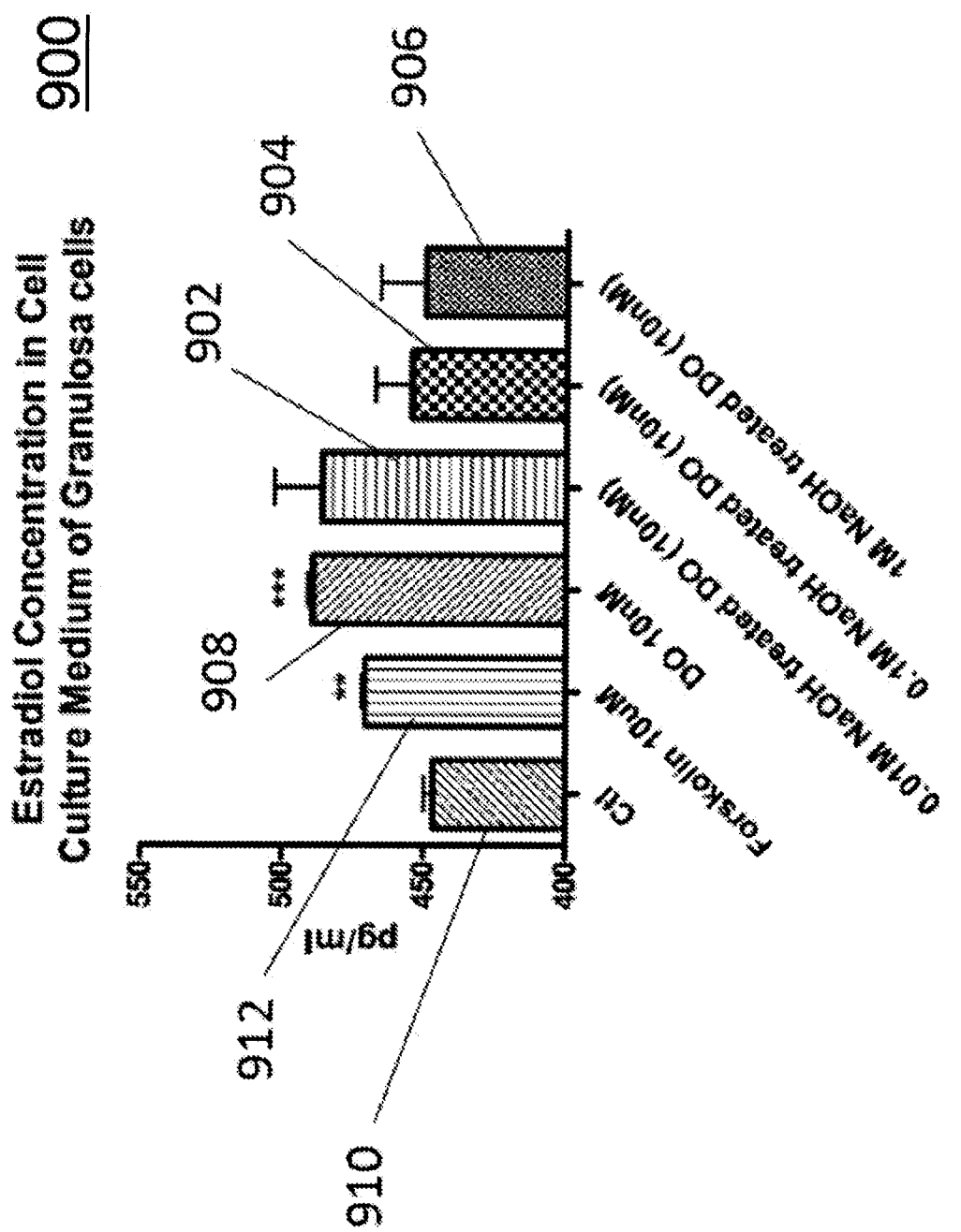
FIG. 9 is a graph showing the estrogenic activity of NaOH treated DOI peptide in granulosa cells. Results are expressed as means±SEM, n=3. * $p<0.05$, $p<0.01$, * $p<0.001$ compared with control group by un-paired t-test.
Figure 36:
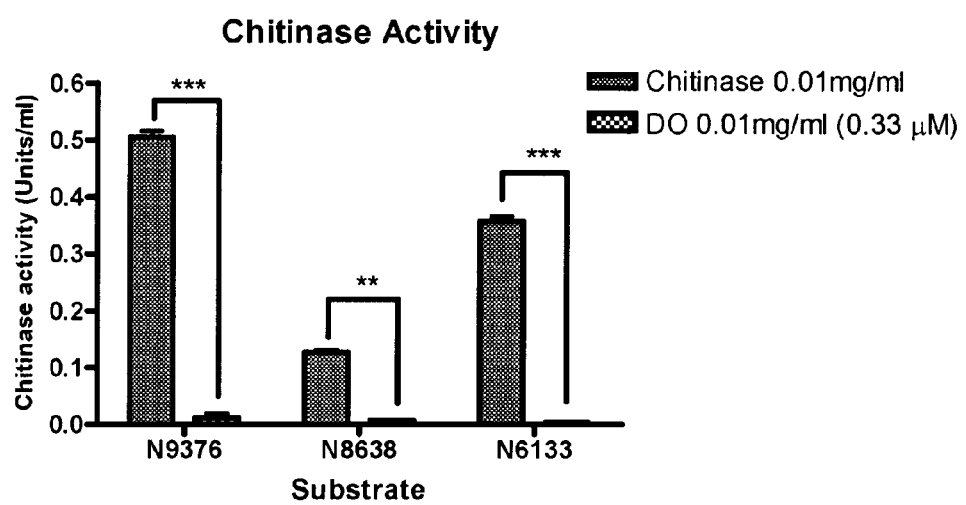
FIG. 36 is a graphical representation of the chitinase activity of DOI. Results are expressed as means±SEM, n=3.  $p<0.01$, * $p<0.001$ compared with the positive chitinase control by un-paired t-test. N9376 refers to 4-Nitrophenyl N-acetyl-β-D-glucosaminide, which is a substrate suitable for exochitinase activity detection (β-N-acetylglucosaminidase activity); N8638 refers to 4-Nitrophenyl β-D-N,N', N"triacetylchitotriose, which is a substrate suitable for endochitinase activity detection; and N6133 refers to 4-Nitrophenyl N,N'-diacetyl-3-D-chitobioside, which is a substrate suitable for exochitinase activity detection (chitobiosidase activity).
Figure 37:
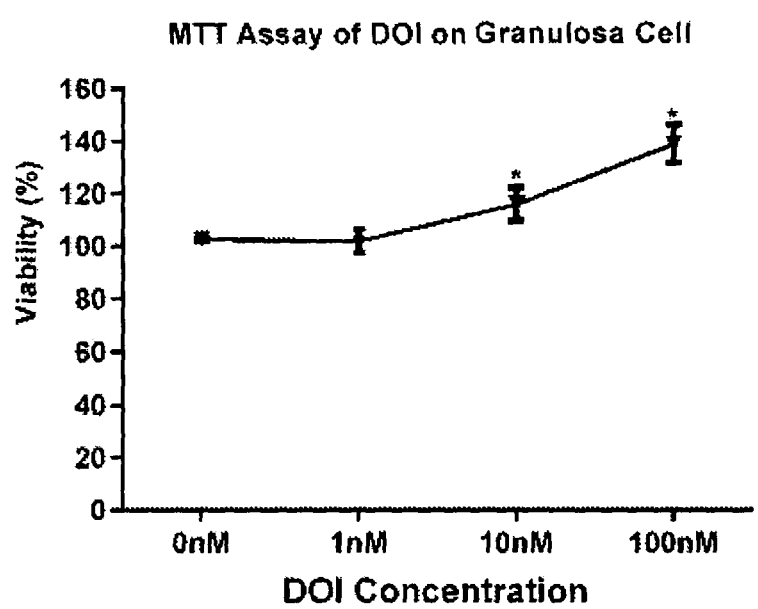
FIG. 37 is a graphical representation of the survival of ovarian granulosa cells after treatment with DOI for 48 hours. The results are expressed as means±SEM, n=3.  $p<0.01$, * $p<0.001$ compared with control group by un-paired t-test.

DOI did not possess hemagglutinating activity (data not shown). DOI displayed estrogen-stimulating activity on ovarian granulosa cells at 1-10 nM concentrations, but not at 100 nM concentration. DOI protein (10 nM) exhibited stability in an acidic environment in 0.01-1M HCl (FIG. 10) and thermostability at 80° C. (FIG. 11), but it did not possess stability in an alkaline environment in 0.01-1M NaOH (FIG. 9). The chitinase activity of DOI on three different substrates N9376, N8638 and N6133 was negligible compared with the positive control chitinase (FIG. 36). Viabilities of BT-483 and OVCA-429 showed a slight decrease in a dose-dependent manner after DOI treatment, but viabilities of mouse splenocytes and rat ovarian granulosa cells were increased after DOI treatment (FIGS. 19, 20, 31 and 37).

Action of DOI on Estradiol-Stimulating Effect In Vitro

Figure 40A:
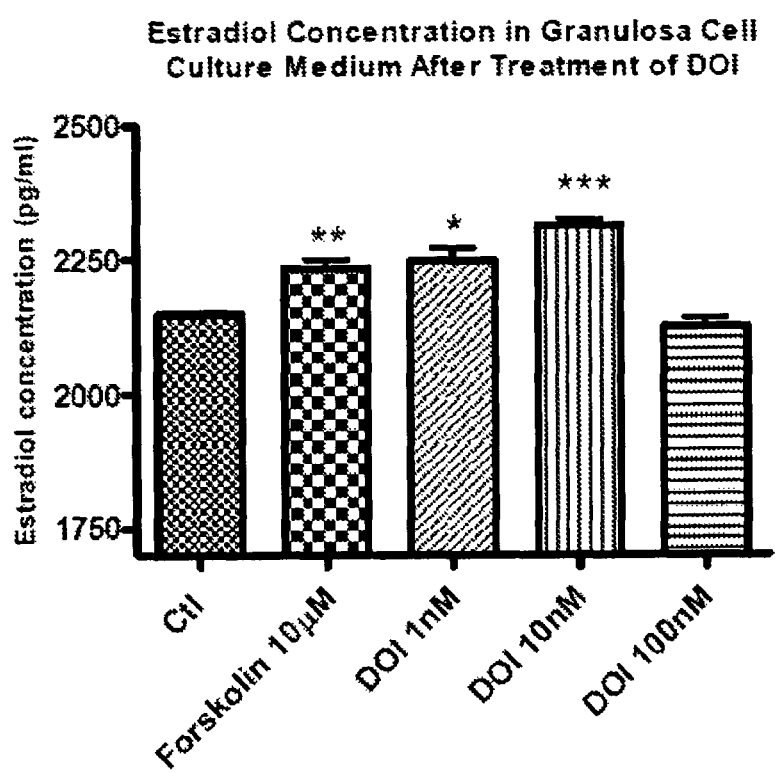
FIG. 40A shows a graphical representation of the stimulatory activity of DOI on estrogen biosynthesis by granulosa cells. The results are expressed as means±SEM, n=3. * $p<0.05$, ** $p<0.01$ compared with control group by un-paired West.
Figure 40B:
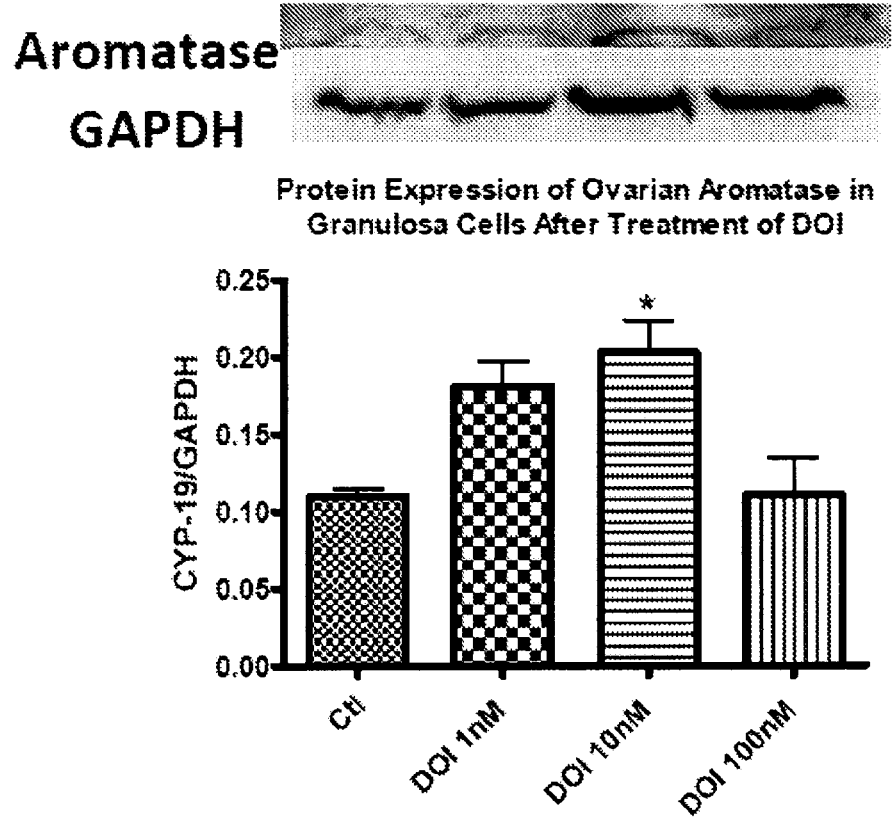
FIG. 40B shows a Western blot of protein expression (with graphical quantitation) of aromatase in ovarian granulosa cells. Results are expressed as means±SEM, n=3. * $p<0.05$,  $p<0.01$, * $p<0.001$ compared with control group by un-paired t-test.
Figure 40C:
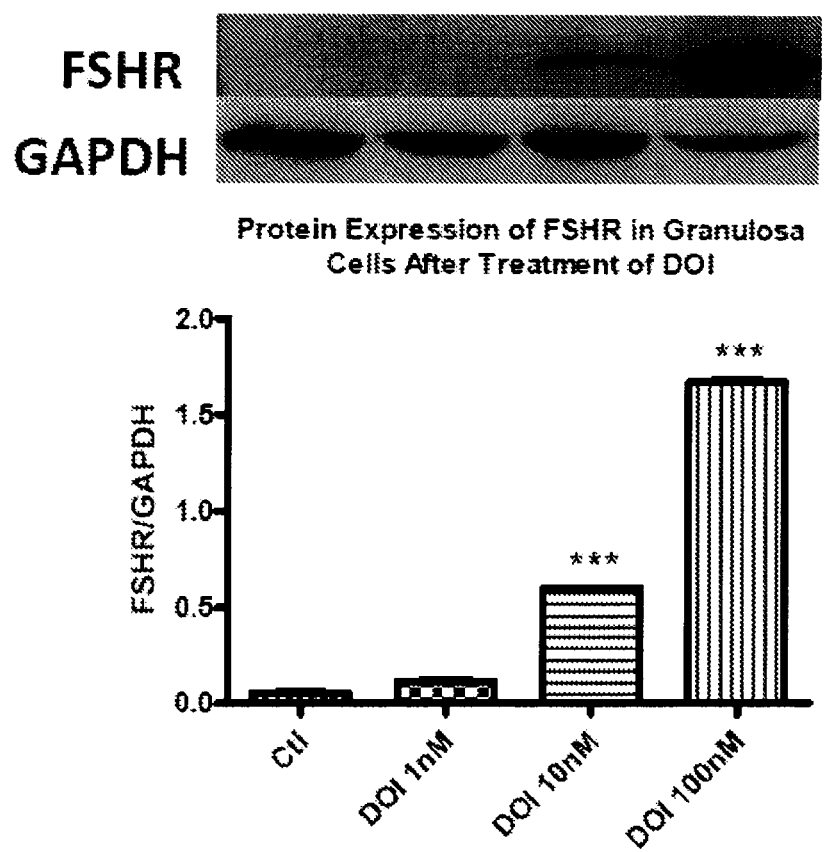
FIG. 40C shows a Western blot of protein expression (with graphical quantitation) of follicle stimulating hormone receptor (FSHR) in ovarian granulosa cells. Results are expressed as means±SEM, n=3. * $p<0.05$,  $p<0.01$,* $p<0.001$ compared with control group by un-paired Nest.

The aromatase expression after DOI treatment was similar to its estrogen-stimulating activity. Treatment with DOI at 1 nM and 10 nM significantly increased estradiol biosynthesis (FIG. 40A) and aromatase expression (FIG. 40B) in granulosa cells compared with control, forskolin as positive control. DOI at 10 nM produced maximal estrogen-stimulating effect. DOI at 100 nM did not show any estrogen stimulating activity compared with control. The FSHR expression increased with DOI treatment at 1 nM-100 nM treatment (FIG. 40C).

Figure 40D:
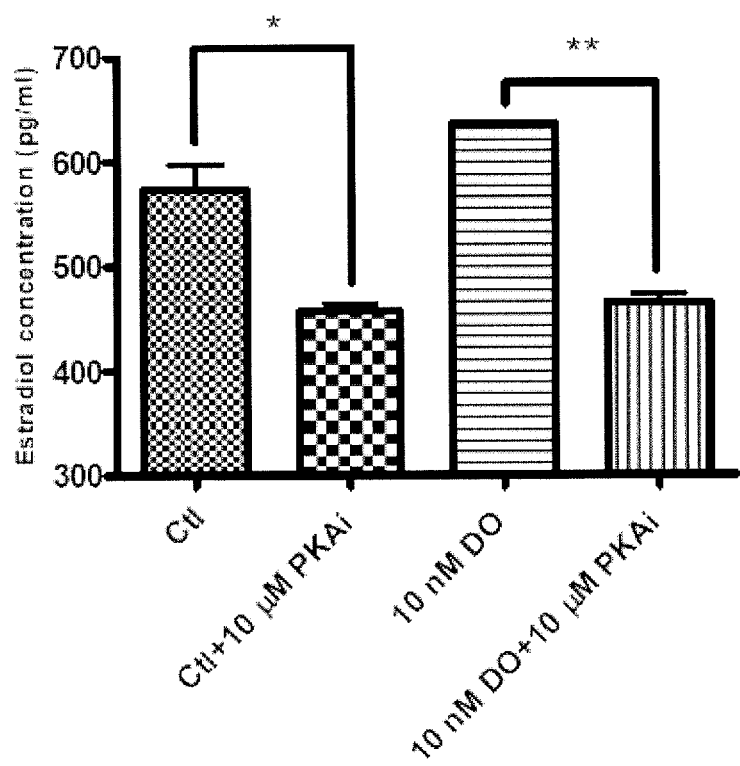
FIG. 40D is a graph showing the estradiol concentration in granulosa cell culture medium with treatment of protein kinase A inhibitor (PKAi). Results are expressed as means±SEM, n=3. * $p<0.05$,  $p<0.01$, * $p<0.001$ compared with control group by un-paired t-test.
Figure 40E:
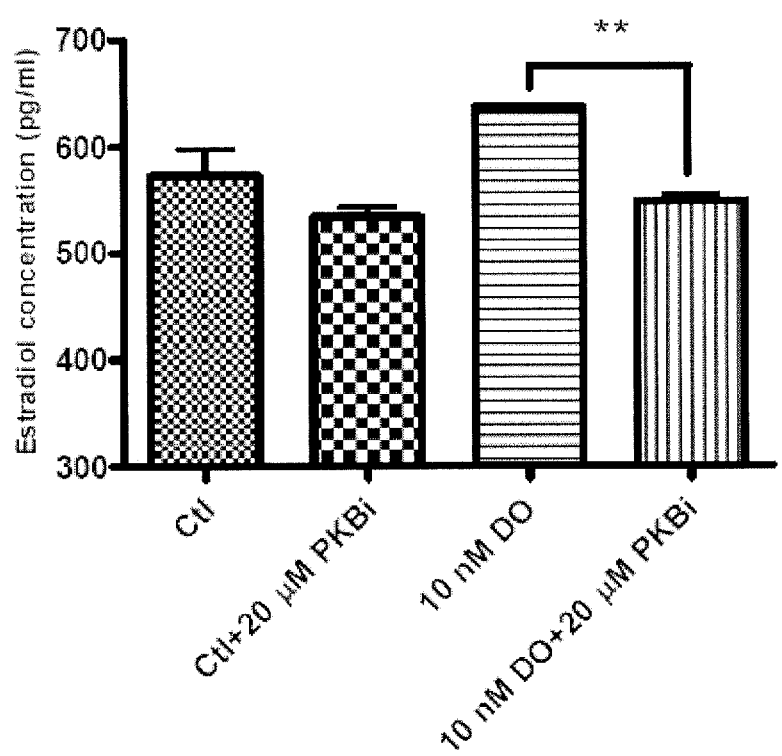
FIG. 40E is a graph showing the estradiol concentration in granulosa cell culture medium with treatment of protein kinase B inhibitor (PKBi). Results are expressed as means±SEM, n=3. *$p<0.05$,  $p<0.01$, * $p<0.001$ compared with control group by un-paired t-test.
Figure 40F:
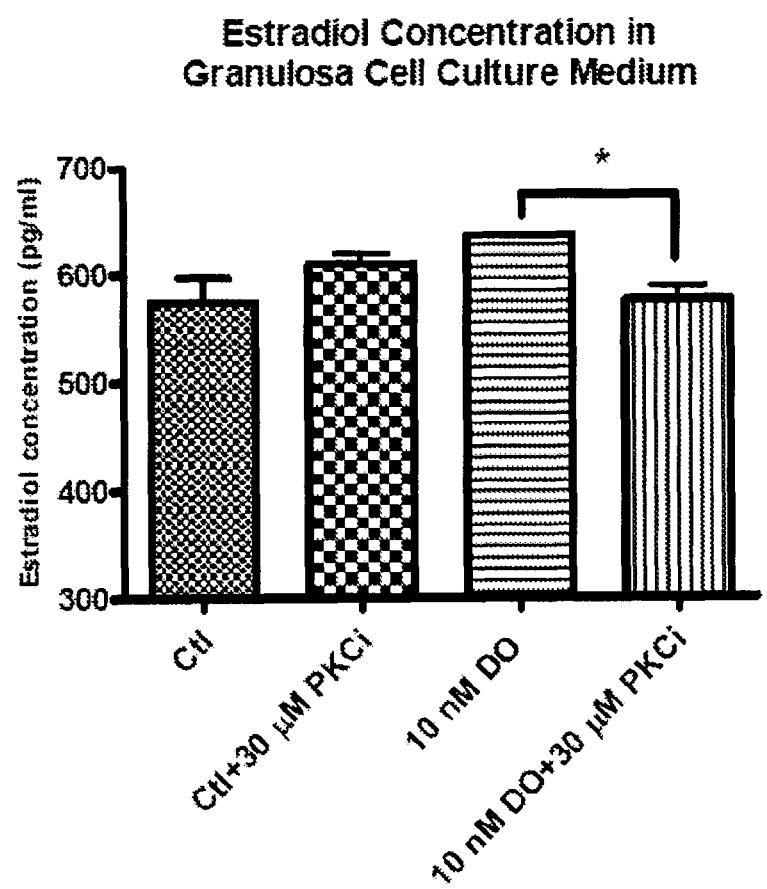
FIG. 40F is a graph showing the estradiol concentration in granulosa cell culture medium with treatment of protein kinase C inhibitor (PKCi). Results are expressed as means±SEM, n=3. * $p<0.05$,  $p<0.01$,* $p<0.001$ compared with control group by un-paired t-test.
Figure 40G:
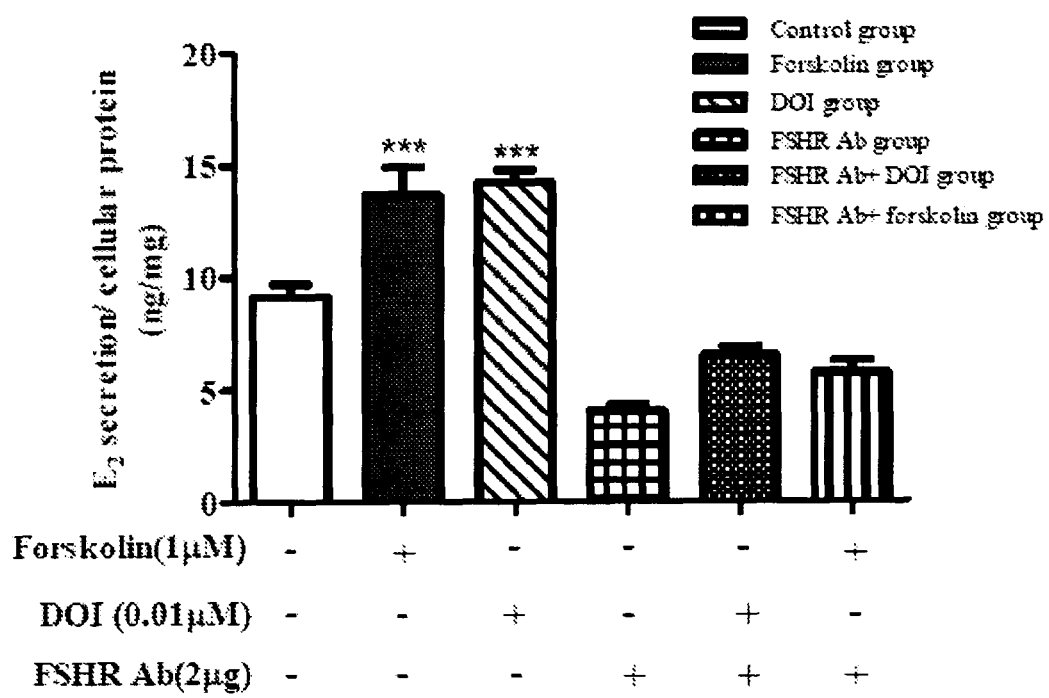
FIG. 40G shows a graph of the effects of DOI treated FSHR-attenuated ovarian granulosa cells after 12 hours of treatment. The results are expressed as means±SEM, n=3. * $p<0.05$, ** $p<0.01$ compared with control group by un-paired t-test.

The estradiol level in the culture medium of granulosa cells was significantly decreased both in the control group and DOI-treated group in the presence of PKAi (FIG. 40D). PKAi one-fold decrease the estrogen-stimulating activity after 10 nM DOI treatment (FIG. 40D). Treatment with PKBi and PKCi did not affect the culture medium estradiol level in the control groups; instead, those of the DOI treated group were decreased significantly (FIG. 40). It was slightly reduced in the presence of PKB inhibitor and PKC inhibitors (FIG. 40E, F). The estradiol stimulating effect of DOI was abolished in the FSHR-attenuated ovarian granulosa cell model (FIG. 40G).

Action of DOI on Estradiol-Stimulating Effect In Vivo

The body weight of the SD rats did not change significantly during the treatment with DO and Premarin (data not shown). The ratio of ovarian weight over total body weight remained steady after treatment with 2.5 and 5 mg/kg DOI compared with control, but it increased from 0.032% to 0.047% and 0.048%, p<0.05 after treatment with 10 mg/kg DOI and premarin, respectively. (data not shown).

Detection of Hormone Levels

The estradiol and progesterone levels reached the peak after treatment for six weeks with DOI at the concentration of 5 mg/kg (FIG. 12). However, treatment with the highest concentration of DOI for six weeks did not significantly increase estradiol and progesterone levels compared with control. Premarin is the HRT group, also increase the estradiol biosynthesis.

Determination of the Estrogen-Related Gene Expression by Real Time PCR In Vivo

Figure 15:
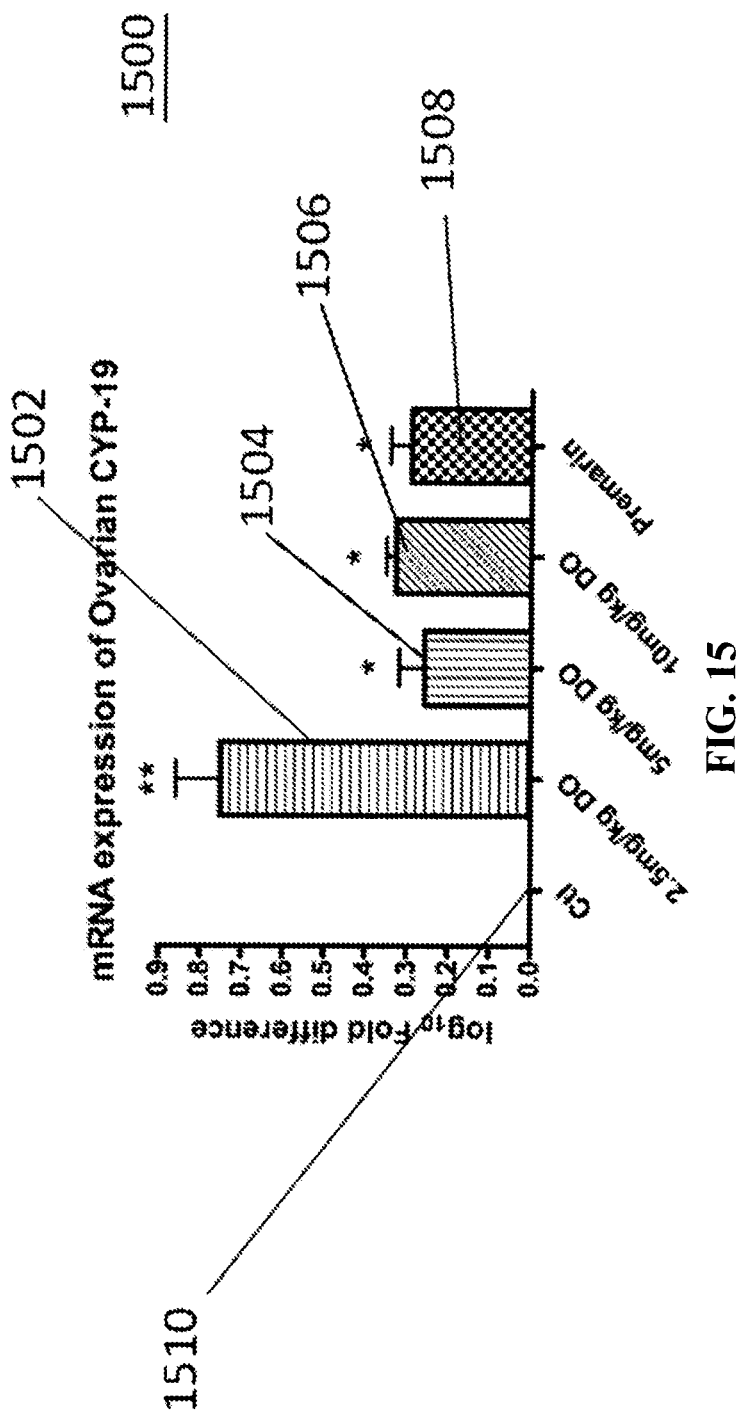
FIG. 15 is a graph showing mRNA expression of ovarian CYP-19 aromatase in ovaries from Sprague-Dawley rats after a 6-week treatment with DOI peptide. Results are expressed as means±SEM, n=6. * $p<0.05$, $p<0.01$, *$p<0.001$ compared with control group by One Way ANOVA followed by Dunnett's Multiple Comparison Test. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.
Figure 16:
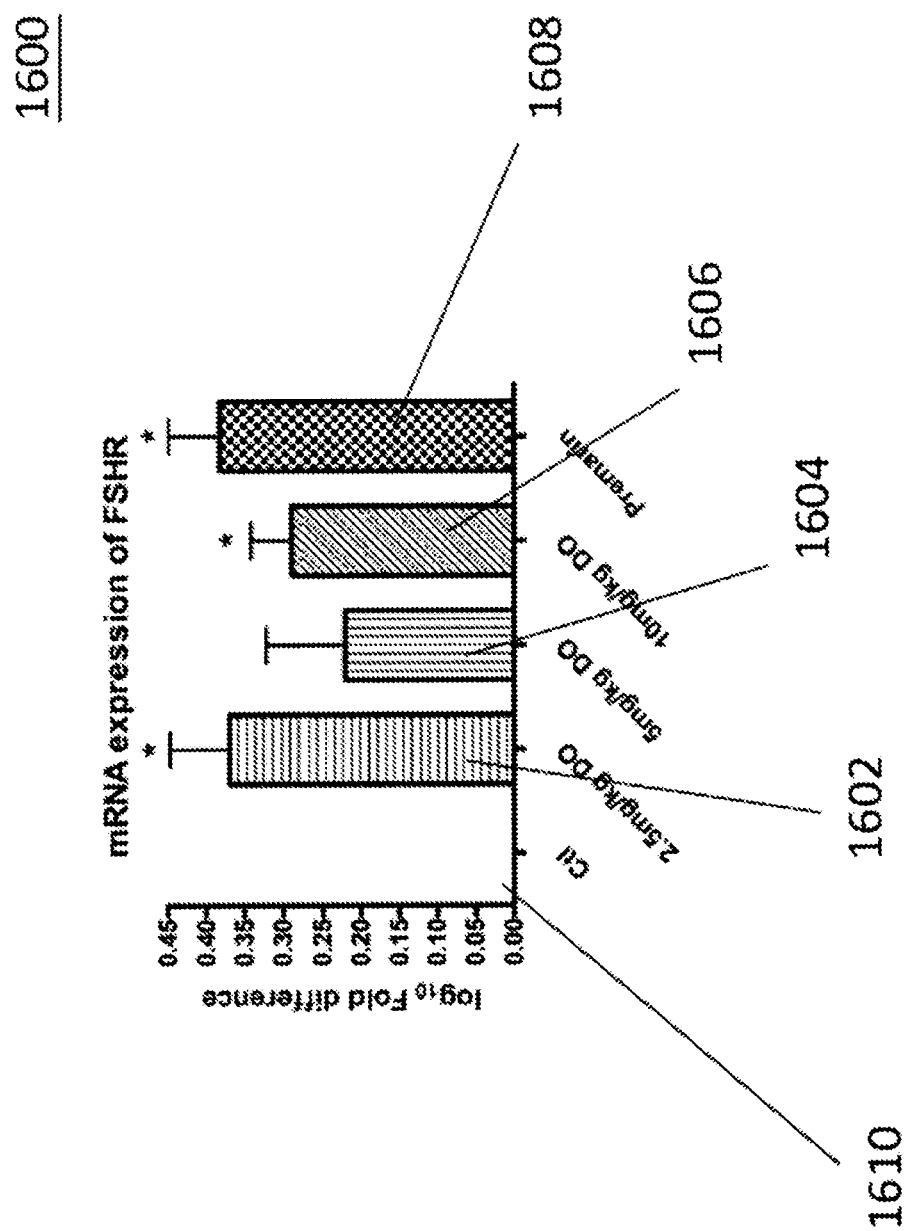
FIG. 16 is a graph showing mRNA expression of FSHR in ovaries from Sprague-Dawley rats after a 6-week treatment with DOI peptide. Results are expressed as means±SEM, n=6. * $p<0.05$, $p<0.01$, *$p<0.001$ compared with control group by One Way ANOVA followed by Dunnett's Multiple Comparison Test. Ctl: old control group receiving intraperitoneal injections of PBS; Premarin: positive control group treated with Premarin (12.4 mg/kg) by oral administration; DOI group: DOI treated group receiving daily intraperitoneal injections of DOI at 2.5 mg/kg, 5 mg/kg and 10 mg/kg, respectively.
Figure 38:
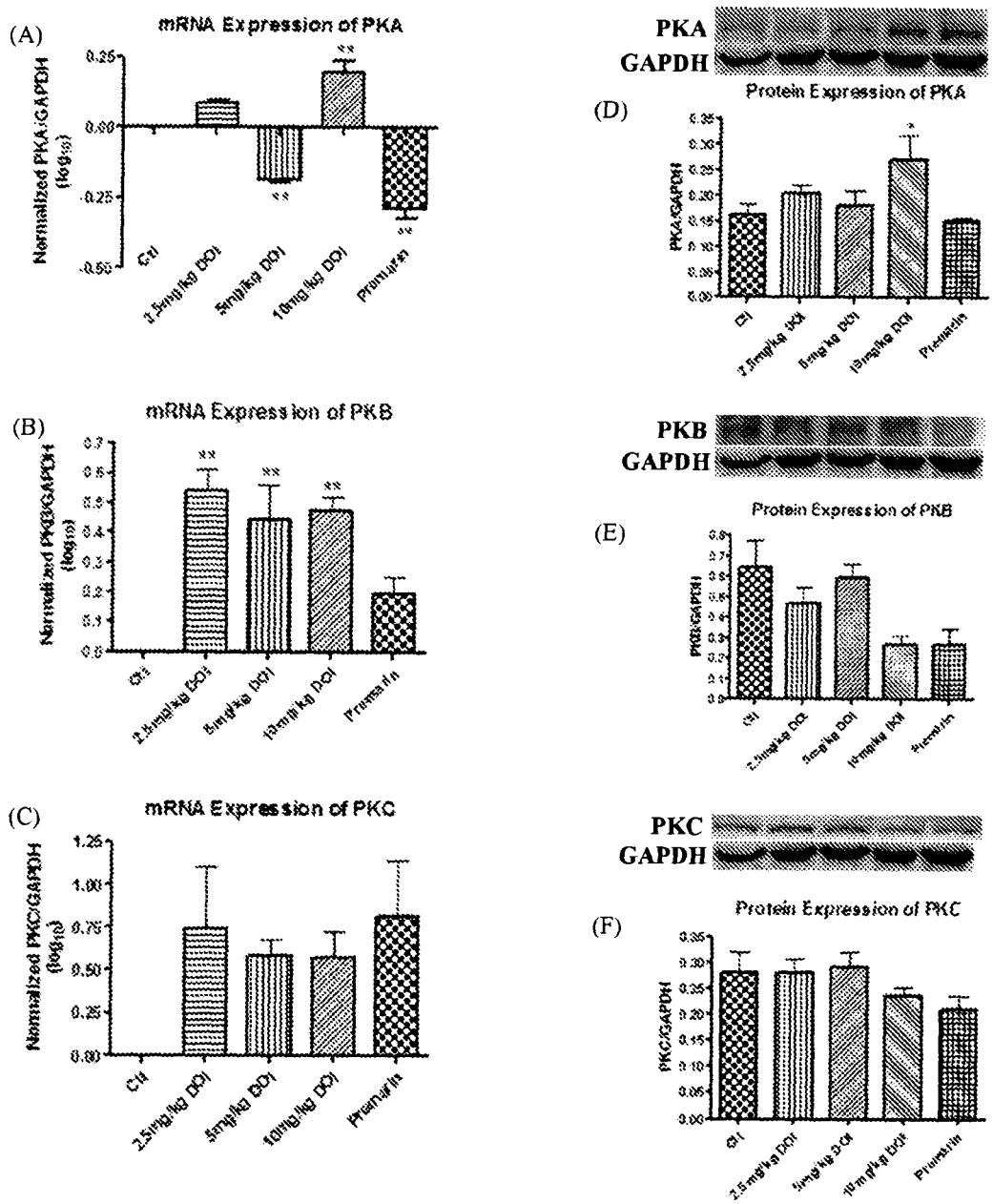
FIG. 38 shows the mRNA expression of (A) PKA, (B) PKB, (C) PKC; and the protein expression of (D) PKA, (E) PKB, (F) PKC by western blot (with graphical quantitation of protein expression relative to GAPDH loading control of respective western blots) in ovaries of Sprague-Dawley rats after 6-week treatment with DOI. Results are expressed as means±SEM, n=3 for mRNA, n=6 for protein. * $p<0.05$, $p<0.01$, *$p<0.001$, compared with control group by one-way ANOVA and un-paired t-test, respectively.

The mRNA expression of both CYP-19 and FSHR in SD-rat ovaries was significantly increased after treatment with DOI and Premarin (FIGS. 15 and 16). In both cases, the group treated with 2.5 mg/kg DOI had the highest mRNA expression among the 3 dosages of DOI compared with the control group and the effect was not dose-dependent. The mRNA expression of both PKA and PKB in SD-rat ovaries was significantly increased after treatment with DOI (FIG. 38A-B).

Determination of the Estrogen-Related by Western Blotting Analysis In Vivo

The protein expression level of ovarian aromatase was upregulated significantly in the groups treated with 2.5 mg/kg and 5 mg/kg DOI. The protein expression level of the 10 mg/kg DOI treated group was similar to the control and that of the Premarin treated group was attenuated significantly (FIGS. 17 and 18). However, the protein expression level of aromatase in mammary gland did not show significant difference compared with the control (FIG. 34). Treatment with Premarin did not affect the protein expression level of ovarian FSHR while treatment with DOI at 2.5 mg/kg, 5 mg/kg and 10 mg/kg enhanced the expression significantly. The protein expression level of PKA was upregulated significantly in the groups treated with 10 mg/kg DOI (FIG. 38D).

Measurement of Bone Mineral Density and Micro-Architecture by Micro-CT Scanning

Figure 39:
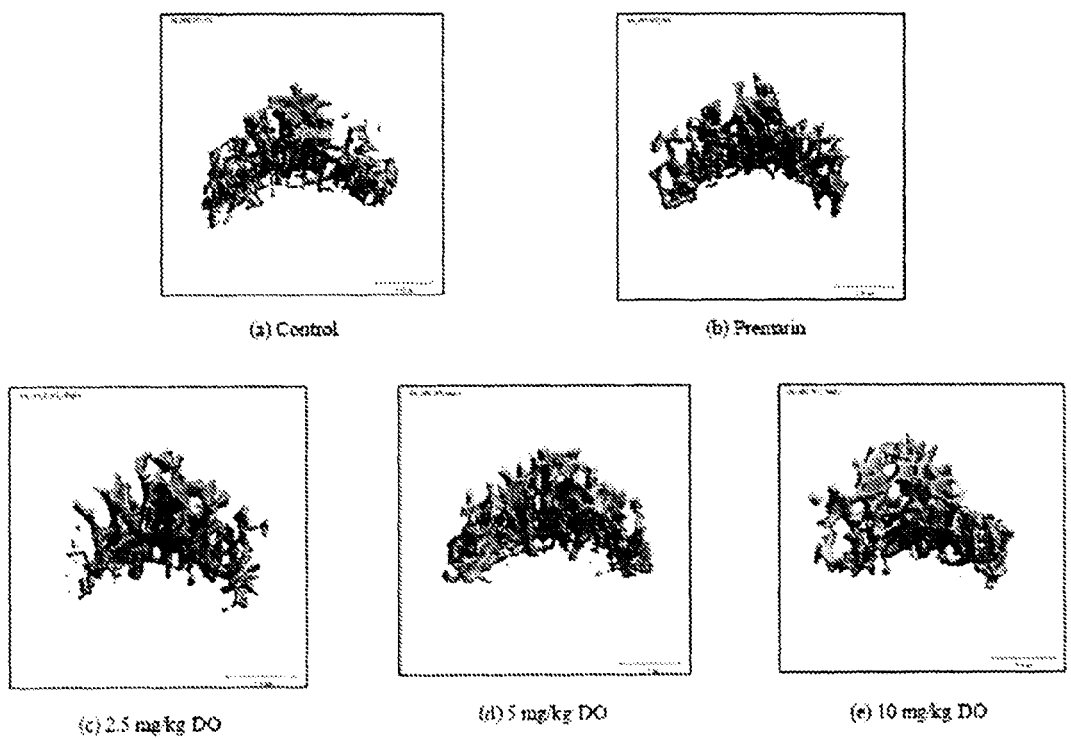
FIG. 39 shows volume rendered images of L2 vertebrae in 16-18 month-old SD female rats with (a) no treatment (control), (b) premarin administration, and rats administered each of (c) 2.5 mg/kg DO, (d) 5 mg/kg DO, (e) 10 mg/kg DO (image presented with BV/TV closest to the group mean value).

Volume rendered images at L2 vertebrae in 18-month-old SD female rats receiving different dosages of DOI are presented in FIG. 39. All DOI-treated groups demonstrated a rise in the apparent bone mineral density of vertebra L2 compared with the control group. The apparent bone mineral density significantly augmented following treatment with DOI at the dosages of 2.5 mg/kg and 5 mg/kg (FIG. 22). Treatment with DOI, but not Premarin, had a tendency to increase the bone volume fraction of vertebra L2. DOI at the dosage of 2.5 mg/kg significantly elevated the bone volume fraction compared with the control group (FIG. 23). The trabecular number of vertebra L2 showed a slight increase after the treatments, nevertheless the increase was not significant compared with the control group (FIG. 24). Treatment with 2.5 mg/kg and 5 mg/kg DOI significantly enhanced the trabecular thickness of vertebra L2 compared with the control group (FIG. 25). All the DOI-treated groups revealed a decline in the structure model index of vertebra L2 compared with the control group and the reduction was significant in the 2.5 mg/kg DOI-treated group (FIG. 26). The trabecular separation of vertebra L2 did not show significant changes after the treatments with the exception of the group treated with 5 mg/kg DOI (FIG. 27).

Detection of Protein Level of Brain Derived Neurotrophic Factor (BDNF) and TrkB gp445

Figure 29:
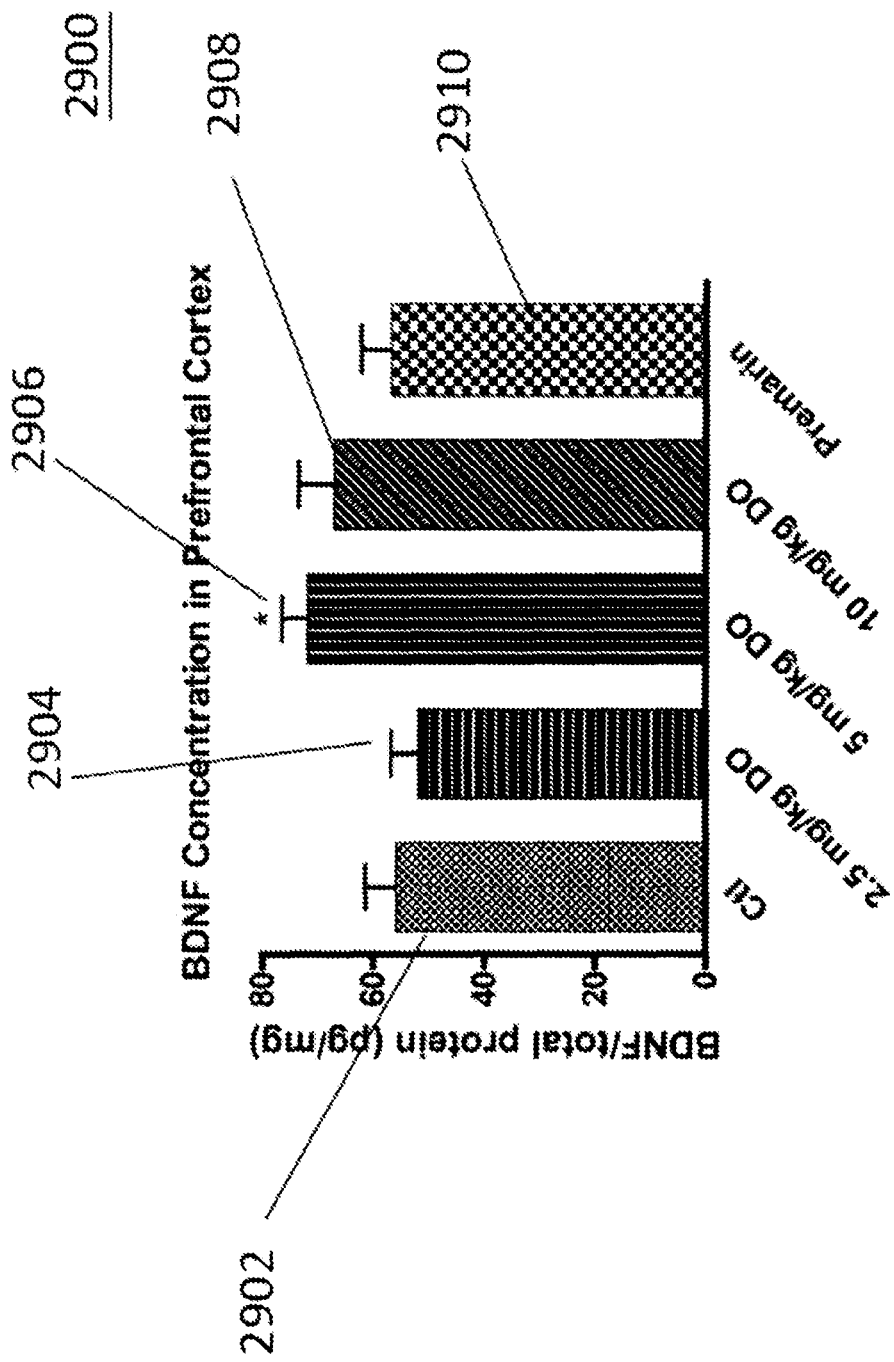
FIG. 29 is a graph showing the protein level of brain derived neurotrophic factor (BDNF) protein in the prefrontal cortex of Sprague-Dawley rats after 6-week treatment with DOI peptide. Results are expressed as means±SEM, n=6. * p<0.05, ** p<0.01 compared with control group by un-paired Nest. Ctl: old control group receiving intraperitoneal injections of PBS; Premarin: positive control group treated with Premarin (12.4 mg/kg/daily) by oral administration; DOI group: DOI treated group receiving daily intraperitoneal injections of DOI at 2.5 mg/kg, 5 mg/kg and 10 mg/kg, respectively.

The BDNF concentration in the prefrontal cortex was significantly increased after treatment with 5 mg/kg DOI (FIGS. 28 and 29). The other treatment groups did not bring about significant changes. The DOI (2.5 mg/kg)-, DOI (5 mg/kg)- and Premarin-treated groups showed significant increase in the expression of TrkB gp145 receptor (FIG. 30).

DISCUSSION

The chemical compositions and pharmacology of *Dioscorea* species have been extensively studied. In the present invention, a protein, designated as DOI, with a molecular weight of 32.5 kDa as measured by size-exclusion column chromatography, was firstly characterized from *Dioscorea opposita* Thunb. The high purity of isolated DOI is revealed and visualized a single band in 15% SDS-PAGE after silver-staining (FIG. 5A-B). After Blast analysis of N-terminal sequence of DOI in NCBI, its high E-value (>10$^{-3}$) indicates that the N-terminal sequence belongs to a novel protein. Results obtained from Blast demonstrated that DOI is a member of the chitinase-like superfamily (Table 5). Results obtained from BLAST analysis of partial amino acid sequence of DOI revealed that DOI has high homology with the 27.9 kDa chitinase from *Dioscorea japonica* (AAB23692.1)[23] and the 31.4 kDa chitinase from *Dioscorea oppositifolia* (BAC56863.1)[24]. However, the molecular weight of isolated DOI compared with others is 33.5 kDa, as measured by mass spectrometry (FIG. 35). And the reported N-terminal sequence of isolated DOI shows differences from that of 31.4 kDa chitinase from *Dioscorea oppositifolia* (BAC56863.1)[24]. In addition, the chitinase activity of DOI was negligible in the chitinase assay using three different substrates, N9376, N8638 and N6133 (FIG. 36). These differences may be due to alternative splicing and post-translational modification.

TABLE 5

BLAST analysis of N-terminal sequence of DOI, the high E value
($>10^{-3}$) indicates that the N-terminal sequence is a novel one.

| Protein | Residue no. | | | Sequence | | Residue no. | E-value |
|---|---|---|---|---|---|---|---|
| DOI | 1 | | | GIGKITTYWGQYSDEPSLTEA | | 21 | / |
| allergen Ziz m 1 [*Ziziphus mauritiana*] AAX40948.1 | 25 | Query Sbjct | 2 25 | IGKITTYWGQY--SDEPSLTEA +G I TYWGQY +E SL EA VGGIATYWGQYTETEEGSLAEA | 21 46 | 47 | 0.028 |
| class III chitinase [*Medicago truncatula*] AAQ21404.1 | 28 | Query Sbjct | 3 28 | GKITTYWGQYSDEPSLTEA GKI YWGQ +E L EA GKISIYWGQNGNEGTLAEA | 21 46 | 46 | 0.31 |
| putative secreted hydrolase [*Pseudoalteromonas tunicata* D2] ZP 01135667.1 | 691 | Query Sbjct | 1 691 | GIGKITTYWGQ------YSDEPS GI IT YWGQ YS E S GISNITSYWGQGWWGYLYSGEAS | 17 713 | 713 | 0.43 |
| msrD protein [*Nocardia seriolae*] BAI22688.1 | 100 | Query Sbjct | 3 100 | GKITTYWGQYSD GKIT YWG YSD GKITEYWGNYSD | 14 111 | 111 | 0.6 |
| chitinase-like xylanase inhibitor protein [*Coffea arabica*] ADZ48381.1 | 4 | Query Sbjct | 5 4 | ITTYWGQYSDEPSLTEA I TYWGQ DE SL +A IATYWGQNTDEGSLEDA | 21 20 | 20 | 0.61 |
| pathogenesis-related protein 8 [*Malus x domestica*] ABC47924.1 | 29 | Query Sbjct | 5 29 | ITTYWGQYSDEPSLTEA I TYWGQ +E L EA IATYWGQNGNEGTLAEA | 21 45 | 45 | 1.7 |
| acidic class III chitinase [*Rehmannia glutinosa*] AAO47731.1 | 25 | Query Sbjct | 3 25 | GKITTYWGQYSDEPSLTE GKI YWGQ +E L E GKISIYWGQNGNEGTLAE | 20 42 | 42 | 2.4 |
| transcriptional regulator, AraC family [*Frankia* sp. EUN1f] ZP 06413816.1 | 121 | Query Sbjct | 6 121 | TTYWGQYSDE TTYW QYSDE TTYW-QYSDE | 15 129 | 129 | 3.4 |

Previously, two proteins, named dioscorin [25] and DJ [23], were isolated from *Dioscorea batatas* Decne and *Dioscorea japonica*, respectively. In addition to *Dioscorea batatas* Decne, dioscorin could also be isolated from other *Dioscorea* species, such as *Dioscorea alata* [26, 27]. Although various proteins have been isolated from yam, they show differences in molecular weight, N-terminal sequence, lectin, antioxidative, immunomodulatory, carbonic anhydrase, trypsin inhibiting, chitinase, and estrogen-stimulating activities compared with DOI (Table 6). The data collected are sufficient to enable biological characterization of DOI, and elucidate its potential pharmacological activity.

TABLE 6

Comparison of characteristics of proteins isolated from different *Dioscorea* species.
Estrogen-stimulating activity of protein derived from *Dioscorea* species has not yet been reported.

| | | Dioscorin [25, 26, 27] | |
|---|---|---|---|
| | DOI | *Dioscorea batatas* | DJ [23] |
| Species | *Dioscorea opposite* thunb | Decne/*Dioscorea alata* cv | *Dioscorea japonica* |
| Lectin activity | No | Yes | Nil |
| Antioxidative activity | Nil | Yes | Nil |
| Immunomodulatory/ immunostimulating activities | Yes | Yes | Nil |

TABLE 6-continued

Comparison of characteristics of proteins isolated from different *Dioscorea* species. Estrogen-stimulating activity of protein derived from *Dioscorea* species has not yet been reported.

| Species | DOI *Dioscorea opposite* thunb | Dioscorin [25, 26, 27] *Dioscorea batatas* Decne/*Dioscorea alata* cv | DJ [23] *Dioscorea japonica* |
|---|---|---|---|
| Carbonic anhydrase activity | Nil | Yes | Nil |
| Trypsin inhibiting activity | Nil | Yes | Nil |
| N-terminal sequence/ partial amino acid sequence | Yes (Novel, since E value of N-terminal > $10^{-3}$) | Yes | Yes |
| Chitinase activity | No | Nil | Yes |
| Estradiol-stimulating activity | Yes | Nil | Nil |
| Molecular weight | 33.5 kDa | 31 kDa (Sub-unit) | 28 kDa |

Figure 10:
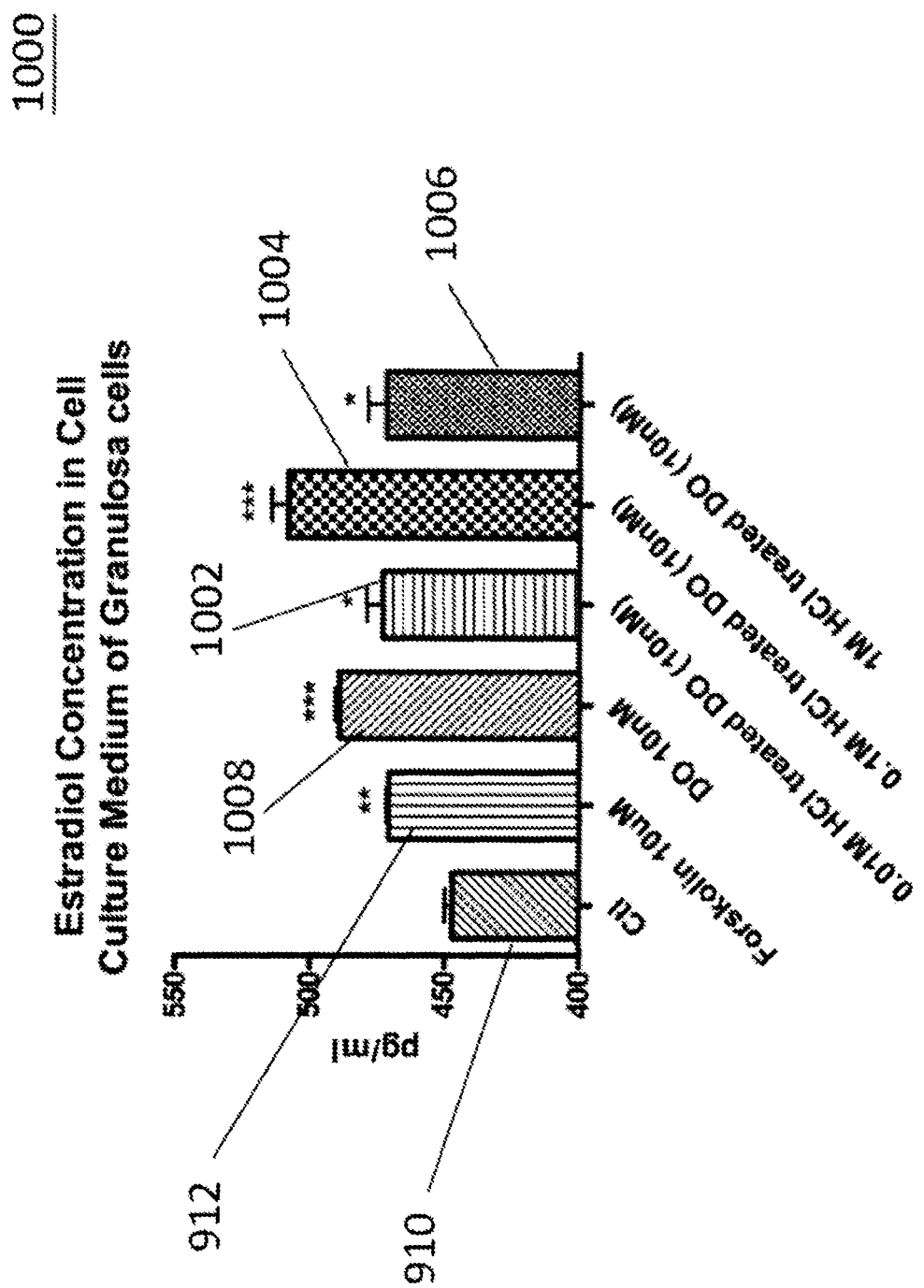
FIG. 10 is a graph showing the estrogenic activity of HCl treated DOI peptide on granulosa cells. Results are expressed as means±SEM, n=3. * $p<0.05$, $p<0.01$, * $p<0.001$ compared with control group by un-paired t-test.

The stability of a protein can be affected by enzymatic degradation, higher temperatures, clearance mechanism, acidic and alkaline condition. Nowadays, these challenges can be addressed by many formulations and technologies, such as polymer polyethylene glycol (PEG)[28]. The estrogen-stimulating activity of DOI was lost in 0.01-1M NaOH. However, DOI exerts acid-stability till 1M HCl, in which DOI can still exert estrogen-stimulating activity on ovarian granulosa cells (FIGS. 9 and 10). These findings demonstrated that the activity of DOI was stable from acidic to weakly alkaline condition (100 mM Tris pH8.0 buffer used during the purification process). Since DOI could withstand temperatures up to 80° C. and treatment with 80° C. significantly increased the activity of DO (FIG. 11), these results indicate that the activity of DOI involves an active site with a short amino acid sequence. The nature of DOI itself has the advantage for protein therapeutics, since its half-life and absorption can be prolonged and degradation under acidic condition and high temperatures retarded.

In order to study the effect of a potential drug candidate on different tissues and understand its side effects, in vitro tissue-specificity characterization is always conducted at an early stage of research and development of a potential drug candidate. Besides, as the reduction in viability of normal cells is a key index of toxicity after exposure to a toxic substance, a viability assay using MTT was used to evaluate the tissue-specificity and toxicity of DOI on various cell types, including breast cancer cell line BT-483, ovarian cancer cell line OVC429, mouse splenocytes and rat ovarian granulosa cells in this invention. Data obtained from the cell viability assay reveals that DOI increases the viability of mouse splenocytes and rat ovarian granulosa cells, and slightly decreases the viability of BT-483 and OVC429 cells in a dose-dependent manner (FIGS. 19, 20, 31 and 37). Therefore, estrogen-stimulating DOI isolated from edible Chinese yam does not cause any apparent toxicity in vitro. In addition, it appears to not have the side effects of hormone replacement therapy, such as promoting breast and ovarian carcinogenesis. Menopause, together with general aging, is accompanied by a decline in immune functions. Changes in the immune system during aging such as changes in immune tolerance, increase of auto-antibodies, decline in function of natural killer cells, B lymphocytes and T lymphocytes have been reported [29]. Besides, estrogen deprivation after menopause is thought to be related to an increased level of pro-inflammatory serum markers, decrease in CD4 T- and B-lymphocytes and decreased cytotoxic activity of natural killer cells [29-31]. In vitro study shows that DO stimulates the viability of mouse splenocytes (FIGS. 19, 20, 31 and 37). DOI may be beneficial in preventing the decline in in immune functions during menopause.

The gradual decline in secretion of ovarian steroids, oestradiol (E2) and progesterone (P), is a hallmark of menopausal women [32], which also represents the breakdown of normal hypothalamic-pituitary-ovarian (H-P-O) function through loss of feedback regulation of ovarian steroids. Estrogen biosynthesis is catalyzed by aromatase in ovarian granulosa cells [33]. In normal women, high circulating levels of follicle-stimulating hormone (FSH) induce estrogen secretion by activating the aromatase-encoding gene Cyp19 [34]. Along with aging and menopause, the activity of the ovarian function and steroidogenic enzyme, aromatase, are also lowered [35]. In menopausal women, although the circulating level of FSH remains high for several years, it does not induce an increase of circulating estrogen level. Ovarian granulosa cells secrete estradiol and in turn reveal the function and steroidogenesis of the ovary [36, 37] and a progressive deterioration in ovarian steroidogenesis appears to be a major factor associated with menopause [35]. Therefore, ovarian granulosa cells will be utilized as a cell model for evaluation of ovarian steroidogenesis after DOI treatment [36, 37]. The importance of the FSH pathway for granulosa cell steroidogenesis is well documented. For example, FSH increases the expression and activity of aromatase in granulosa cells resulting in increased biosynthesis of estradiol [38]. In the classically described mechanism of FSHR action, ligand binding results in activation of adenylate cyclase, increased production of cAMP, and activation of protein kinase A (PKA) and PKB[39-41], which, in turn, directly influences the expression and activity of aromatase. PKC as a negative regulator [42]. Interestingly, there is evidence suggesting that yam induces estradiol secretion in menopausal women [22]. In embodiments of the present invention, the bioactive principle of Chinese yam which elevates estradiol biosynthesis is characterized. Results obtained from in vitro study demonstrate that DOI treatment up-regulated FSHR and aromatase expression, which can in turn increase estradiol biosynthesis in ovarian granulosa cells via the FSHR-aromatase pathway (FIG. 40A-C). Results of the protein kinase inhibition assay indicate that protein kinase A, B and C are all involved, because the activity of DOI protein is abolished by inhibitors of PKA/PKB/PKC (FIG. 40D-E). FSHR antibody, which blocks its antigen's N-terminal, was used to establish a FSHR-attenuated ovarian granulosa cell model, and the results reveal that the estradiol stimulating effect of DOI is abolished in this model. This confirms that DOI promotes estradiol biosynthesis, at least, via interaction with FSHR (FIG. 40G).

A progressive deterioration in the neuroendocrine axis, including ovarian steroidogenesis, in female rats and women appears to be a major factor associated with typical reproductive aging [43-48]. Therefore, sixteen- to eighteen-month-old female SD rats with low estrogen level, employed as a selected animal model in embodiments of the present invention, can mimic reproductive failure in menopausal women, because the gradual decline of neuroendocrine function in rats is similar to human. After treatment with DOI, the body weight of SD rats did not show significant changes (data not shown). As the reduction in body weight can be a sensitive index of toxicity after the animal has been exposed to a toxic substance, this reveals that DOI does not cause any apparent toxicity in vivo. In addition, DOI increases the ovarian weight at the 10 mg/kg dosage, indicating prevention of tissue degeneration during the normal ovarian aging process. The protein DOI shows activity in increasing serum estradiol and progesterone levels in vivo after treatment for six weeks. The estradiol and progesterone levels reach the maximum at the concentration of 5 mg/kg and the levels undergo a decline at a higher concentration, 10 mg/kg (FIG. 12A-F). The dose-response curve is bell-shaped, especially for progesterone stimulation. In vivo mechanistic studies reveal that the underlying mechanism for the increase in estradiol level might be, at least, through the up-regulation of protein levels of FSHR, aromatase (FIGS. 15, 16, 17, 18, and 34) and PKA (FIG. 38D). Therefore, one possible pathway of DOI action might be via the pathway involving FSHR, PKA, and aromatase, which is the classical pathway for steroidogenesis. Increasing aromatase expression will increase the cancer risk in breast tissue. Interestingly, data from Western blotting analysis reveals that DOI treatment up-regulates aromatase in the ovary (FIG. 17), but not in the mammary gland tissue (FIG. 34) after treatment with 2.5 mg/kg DOI, which exhibits tissue-specificity. Thus, estrogen-stimulating DOI is expected to be devoid of any side effects of hormone replacement therapy, including evoking breast and ovarian carcinogenesis. Osteoporosis is one of the major menopausal symptoms, which is characterized by reduced bone mass and microarchitectural deterioration of the skeleton, resulting in an increased risk of fractures. Estrogen deficiency is known to be an important contributing factor in the pathogenesis of osteoporosis. The loss of ovarian hormones (estrogen and progesterone) during menopause is one of the major risk factors for osteoporosis, which causes increased bone resorption and decreased bone formation [49, 50]. Bone remodeling increases substantially in the years after menopause and remains elevated in older osteoporotic patients. Bones status as such contributes to the increase in age-related skeletal fragility in women [51]. It has been shown that trabecular bone mineral density, trabecular bone volume fraction, trabecular thickness and trabecular number all decrease with age [52]. Also, a lower bone mass is primarily characterized by a smaller plate-to-rod ratio [53]. All these changes would weaken bone strength and increase the risk of osteoporotic fracture. The trabecular material bone mineral density at L2 mid-vertebral body has clinically been used for assessment of osteoporosis [54], thus it has been used to evaluate the anti-osteoporotic effect of DOI. In embodiments of the present invention, DOI demonstrates beneficial effect on the bone mineral density and micro-architecture in vivo using high resolution microCT. Treatment with DOI results in increased bone mineral density, bone volume fraction, trabecular number, trabecular thickness, and decreased structure model index and trabecular separation of the vertebra L2 (FIGS. 22-27). These bone density and micro-architecture changes favor an enhancement of bone strength [55, 56]. The decrease in structure model index indicates an increase in the ratio of plate shape to rod shape trabeculae. The latter trabecular structure is dominant in osteoporosis [57]. The increase in plate shape trabeculae found in the present invention shows that the bone may become less porous as reflected in the parallel decrease in trabecular separation. These data suggest that the Dioscorea Opposita Tunb enables an anti-osteoporotic effect on the trabecular bone in vivo. Due to the effect of DOI on estradiol and progesterone biosynthesis, DOI can be provided as a therapeutic agent for menopausal osteoporosis.

Besides osteoporosis, cognitive decline is a common phenomenon experienced by menopausal women [58]. A recent study demonstrated that plasma BDNF level can be used as a biomarker for cognitive function of aging women [59] and it has been found to decrease significantly in aged human subjects [60]. Administration of exogenous BDNF was found to offset some physiologic or pathologic age-associated changes in the central nervous system [61]. BDNF is widely expressed in the brain and belongs to neurotrophin family which is a group of small, basic, secreted proteins that aid in the survival, maintenance and plasticity of specific neuronal populations. Among the various parts of the brain, the prefrontal cortex is important for cognitive function [62, 63]. In embodiments of the present invention, treatment with DO increases the protein expression level of BDNF both in the prefrontal cortex and hippocampus as well as its receptor, TrkB gp145 in the prefrontal cortex (FIGS. 28-30). This suggests it is beneficial to the neuronal population in the prefrontal cortex and hence improves cognitive function. However, the pharmacological effect might not be directly due to the protein DOI as it can not cross the blood brain barrier to reach the prefrontal cortex. The effect might be due to the increase in serum estradiol level, as estradiol is believed to be neuroprotective and can increase expression of BDNF [64, 65].

What is claimed is:

1. A method for increasing level of estradiol, estrogen, and/or progesterone in a female subject, comprising:
   administering, to a female subject with an estrogen level lower than that of a normal female population with normal reproductive function, an effective amount of a composition comprising a polypeptide selected from the group consisting of:
   an isolated or substantially pure polypeptide obtainable from *Dioscorea* sp., wherein the polypeptide has an apparent molecular weight of about 32.5 kDA by chromatography, wherein the first twenty-one consecutive amino acids at the N-terminal of the polypeptide consists of SEQ ID NO: 1.

2. The method of claim 1, wherein the subject is a human at menopause, perimenopause, or postmenopause period.

3. The method of claim 1, wherein the subject has a progesterone level lower than that of a normal female population with normal reproductive function.

4. The method of claim 1, wherein the subject has menopausal syndrome.

5. The method of claim 1, wherein the subject has osteoporosis, and the administration of the composition treats osteoporosis.

6. The method of claim 1, wherein the composition is isolated aqueous extract of *Dioscorea Opposita*.

7. A method for treating a female subject having a condition associated with low estrogen level, comprising administering, to a female subject with an estrogen level lower than that of a normal female population with normal reproductive function, an effective amount of a composition comprising an isolated or substantially pure polypeptide obtainable from *Dioscorea* sp., wherein the polypeptide has an apparent molecular weight of about 32.5 kDA by chromatography, wherein the first twenty-one consecutive amino acids at the N-terminal of the polypeptide consists of SEQ ID NO:1;
   wherein the administration achieves at least one therapeutic effect selected from:
   a) increasing serum level of estradiol, estrogen, and/or progesterone;
   b) increasing the expression levels of aromatase CYP-19 and/or follicle-stimulating hormone receptor (FSHR);
   c) increasing the level of brain derived neurotrophic factor (BDNF) and/or TrkB receptor in hippocampus and prefrontal cortex;
   d) treating osteoporosis;
   e) improving cognitive function; and
   f) stimulating a splenic mitosis response.

8. The method of claim 7, wherein the subject is a human at menopause, perimenopause, or postmenopause period.

9. The method of claim 7, wherein the subject has menopausal syndrome.

* * * * *

SEQUENCE LISTING

<160> NUMBER OF SEQ ID NOS: 12

<210> SEQ ID NO 1
<211> LENGTH: 21
<212> TYPE: PRT
<213> ORGANISM: Dioscorea oppositifolia

<400> SEQUENCE: 1

Gly Ile Gly Lys Ile Thr Thr Tyr Trp Gly Gln Tyr Ser Asp Glu Pro
1               5                   10                  15

```
Ser Leu Thr Glu Ala
            20
```

```
<210> SEQ ID NO 2
<211> LENGTH: 24
<212> TYPE: DNA
<213> ORGANISM: Artificial Sequence
<220> FEATURE:
<223> OTHER INFORMATION: sequence is synthesized

<400> SEQUENCE: 2
gagagttcat gagagtctgg atca                                          24

<210> SEQ ID NO 3
<211> LENGTH: 23
<212> TYPE: DNA
<213> ORGANISM: Artificial Sequence
<220> FEATURE:
<223> OTHER INFORMATION: sequence is synthesized

<400> SEQUENCE: 3
gatatagttg ctgtgcttca tca                                           23

<210> SEQ ID NO 4
<211> LENGTH: 22
<212> TYPE: DNA
<213> ORGANISM: Artificial Sequence
<220> FEATURE:
<223> OTHER INFORMATION: sequence is synthesized

<400> SEQUENCE: 4
gaaaggatca tttgctggat tt                                            22

<210> SEQ ID NO 5
<211> LENGTH: 24
<212> TYPE: DNA
<213> ORGANISM: Artificial Sequence
<220> FEATURE:
<223> OTHER INFORMATION: sequence is synthesized

<400> SEQUENCE: 5
cttccaagac atcattctga gaga                                          24

<210> SEQ ID NO 6
<211> LENGTH: 128
<212> TYPE: PRT
<213> ORGANISM: Artificial Sequence
<220> FEATURE:
<223> OTHER INFORMATION: sequence is synthesized

<400> SEQUENCE: 6

Lys Ser Phe Tyr Thr Arg Ser Asn Phe Leu Glu Ala Val Ser Ala Tyr
 1               5                  10                  15

Pro Gly Phe Gly Thr Lys Arg Glu Ile Ala Ala Tyr Phe Ala His Val
            20                  25                  30

Thr His Gly Pro Met Gln Leu Ser Trp Asn Tyr Asn Tyr Ile Asp Ala
        35                  40                  45

Gly Lys Glu Leu His Phe Asp Gly Leu Asn Asp Pro Asp Ile Val Gly
    50                  55                  60

Arg Asp Pro Ile Ile Ser Phe Lys Thr Ser Leu Trp Phe Trp Ile Arg
65                  70                  75                  80

Lys Gly Val Gln Tyr Val Ile Leu Asp Pro Asn Gln Gly Phe Gly Ala
                85                  90                  95
```

```
Thr Ile Arg Ile Ile Asn Gly Gly Gln Glu Cys Asp Gly His Asn Thr
            100                 105                 110
Ala Gln Met Met Ala Arg Val Gly Tyr Tyr Gln Glu Tyr Cys Ala Gln
        115                 120                 125
```

```
<210> SEQ ID NO 7
<211> LENGTH: 18
<212> TYPE: DNA
<213> ORGANISM: Artificial Sequence
<220> FEATURE:
<223> OTHER INFORMATION: sequence is synthesized

<400> SEQUENCE: 7
tggatgtgat cggggaaa                                                 18

<210> SEQ ID NO 8
<211> LENGTH: 18
<212> TYPE: DNA
<213> ORGANISM: Artificial Sequence
<220> FEATURE:
<223> OTHER INFORMATION: sequence is synthesized

<400> SEQUENCE: 8
aagctgtcgg ccttttca                                                 18

<210> SEQ ID NO 9
<211> LENGTH: 21
<212> TYPE: DNA
<213> ORGANISM: Artificial Sequence
<220> FEATURE:
<223> OTHER INFORMATION: sequence is synthesized

<400> SEQUENCE: 9
aaaactttct tcgtccacac g                                             21

<210> SEQ ID NO 10
<211> LENGTH: 21
<212> TYPE: DNA
<213> ORGANISM: Artificial Sequence
<220> FEATURE:
<223> OTHER INFORMATION: sequence is synthesized

<400> SEQUENCE: 10
ggactgctct ggtactgttg c                                             21

<210> SEQ ID NO 11
<211> LENGTH: 20
<212> TYPE: DNA
<213> ORGANISM: Artificial Sequence
<220> FEATURE:
<223> OTHER INFORMATION: sequence is synthesized

<400> SEQUENCE: 11
gcatagactg ggacctgctt                                               20

<210> SEQ ID NO 12
<211> LENGTH: 20
<212> TYPE: DNA
<213> ORGANISM: Artificial Sequence
<220> FEATURE:
<223> OTHER INFORMATION: sequence is synthesized

<400> SEQUENCE: 12
ccaggccata gtcatctgtg                                               20
```